(12) United States Patent
Bolli et al.

(10) Patent No.: US 6,596,719 B1
(45) Date of Patent: Jul. 22, 2003

(54) 6 ALKOXY-4-PYRIMIDINYL BIS-SULFONAMIDES

(75) Inventors: Martin Bolli, Allschwil (CH); Christoph Boss, Allschwil (CH); Martine Clozel, Saint-Louis (FR); Walter Fischli, Allschwil (CH)

(73) Assignee: Actelio Pharmaceuticals Ltd. (CH)

( * ) Notice: Subject to any disclaimer, the term of this patent is extended or adjusted under 35 U.S.C. 154(b) by 0 days.

(21) Appl. No.: 10/031,555
(22) PCT Filed: Aug. 16, 2000
(86) PCT No.: PCT/EP00/07999
§ 371 (c)(1), (2), (4) Date: Aug. 16, 2001
(87) PCT Pub. No.: WO01/17976
PCT Pub. Date: Mar. 15, 2001

(30) Foreign Application Priority Data

Sep. 3, 1999 (WO) ............................... PCT/EP99/06485
Feb. 15, 2000 (WO) ............................... PCT/EP00/01222

(51) Int. Cl.$^7$ ............... C07D 239/47; C07D 401/14; C07D 413/04; A61K 31/505; A61P 9/12
(52) U.S. Cl. ............... 514/235.8; 514/269; 514/274; 544/122; 544/296; 544/319; 544/320; 544/321
(58) Field of Search ................. 514/235.8, 269, 514/274; 544/122, 296, 319, 320, 321

(56) References Cited

U.S. PATENT DOCUMENTS 5,739,333 A * 4/1998 Yamada et al. ............. 544/296
5,939,446 A   8/1999 Murugesan .................. 514/380

FOREIGN PATENT DOCUMENTS

| EP | 0 713 875 A | 5/1996 |
|----|-------------|--------|
| EP | 0 743 307 A | 11/1996 |
| WO | WO 96 19459 A | 6/1996 |

* cited by examiner

Primary Examiner—Mukund Shah
Assistant Examiner—Thomas McKenzie
(74) Attorney, Agent, or Firm—Pennie & Edmonds LLP

(57) ABSTRACT

The present invention relates to novel bis-sulfonamides represented, for example, by formula I below and a pure diastereomer, a mixture of diastereomers, a diastereomeric racemate, a mixture of diastereomeric racemates and meso-forms and a pharmaceutically acceptable salt thereof, wherein $R^1$ represents aryl; aryl-lower alkyl; aryl-lower alkenyl; heteroaryl; or heteroaryl-lower alkyl; and $R^2$ represents lower alkyl; trifluoromethyl; lower alkoxy-lower alkyl; lower alkenyl; lower alkynyl; aryl; aryl-lower alkyl; aryl-lower alkenyl; heterocyclyl; heterocyclyl-lower alkyl; heteroaryl; heteroaryl-lower alkyl; cycloalkyl; or cycloalkyl-lower alkyl. The present invention also relates to a process for manufacturing those compounds, pharmaceutical compositions containing one or more of those compounds as endothelin antagonists, and a method of treating a subject having a disorder involving endothelin with the compounds of

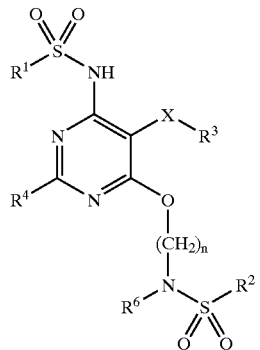

formula I the invention.

24 Claims, No Drawings

6 ALKOXY-4-PYRIMIDINYL BIS-SULFONAMIDES

The present invention relates to novel bis-sulfonamides of the general formula I and their use as active ingredients in the preparation of pharmaceutical compositions. The invention also concerns related aspects including processes for the preparation of the compounds, pharmaceutical compositions containing one or more compounds of the general formula I and especially their use as endothelin antagonists.

Endothelins (ET-1, ET-2, and ET-3) are 21-amino acid peptides produced and active in almost all tissues (Yanagisawa M et al.: Nature (1988) 332:411). Endothelins are potent vasoconstrictors and important mediators of cardiac, renal, endocrine and immune functions (McMillen M A et al.: J Am Coll Surg (1995) 180:621). They participate in bronchoconstriction and regulate neurotransmitter release, activation of inflammatory cells, fibrosis, cell proliferation and cell differentiation (Rubanyi G M et al.: Pharmacol Rev (1994) 46:328).

Two endothelin receptors have been cloned and characterized in mammals ($ET_A$, $ET_B$) (Arai H et al.: Nature (1990) 348:730; Sakurai T et al.: Nature (1990) 348:732). The $ET_A$ receptor is characterized by higher affinity for ET-1 and ET-2 than for ET-3. It is predominant in vascular smooth muscle cells and mediates vasoconstricting and proliferative responses (Ohlstein E H et al.: Drug Dev Res (1993) 29:108). In contrast, the $ET_B$ receptor has equivalent affinity for the 3 endothelin isopeptides and binds the linear form of endothelin, tetra-ala-endothelin, and sarafotoxin S6C (Ogawa Y et al.: BBRC (1991) 178:248). This receptor is located in the vascular endothelium and smooth muscles, and is also particularly abundant in lung and brain. The $ET_B$ receptor from endothelial cells mediates transient vasodilator responses to ET-1 and ET-3 through the release of nitric oxide and/or prostacyclin whereas the $ET_B$ receptor from smooth muscle cells exerts vasoconstricting actions (Sumner M J et al.: Brit J Pharmacol (1992) 107:858). $ET_A$ and $ET_B$ receptors are highly similar in structure and belong to the superfamily of G-protein coupled receptors.

A pathophysiological role has been suggested for ET-1 in view of its increased plasma and tissue levels in several disease states such as hypertension, sepsis, atherosclerosis, acute myocardial infarction, congestive heart failure, renal failure, migraine and asthma. As a consequence, endothelin receptor antagonists have been studied extensively as potential therapeutic agents. Endothelin receptor antagonists have demonstrated preclinical and/or clinical efficacy in various diseases such as cerebral vasospasm following subarachnoid hemorrhage, heart failure, pulmonary and systemic hypertension, neurogenic inflammation, renal failure and myocardial infarction.

Today, no endothelin receptor antagonist is marketed yet, several are in clinical trials. However, these molecules possess a number of weaknesses such as complex synthesis, low solubility, high molecular weight, poor pharmacokinetics, or safety problems (e.g. liver enzyme increases). Furthermore, the contribution of differential $ET_A$/$ET_B$ receptor blockade to the clinical outcome is not known. Thus, tailoring of the physicochemical and pharmacokinetic properties as well as the selectivity profile of each antagonist for a given clinical indication is mandatory. We have discovered a new class of bis-sulfonamide compounds of the structure below and found that they allow the specific tailoring described above.

The inhibitory activity of the compounds of formula I on endothelin receptors can be demonstrated using the test procedures described hereinafter:

For the Evaluation of the Potency and Efficacy of the Compounds of the General Formula I the Following Tests Were Used 1) Inhibition of Endothelin Binding to Membranes from CHO Cells Carrying Human ET Receptors:

For competition binding studies, membranes of CHO cells expressing human recombinant $ET_A$ or $ET_B$ receptors were used. Microsomal membranes from recombinant CHO cells were prepared and the binding assay made as previously described (Breu V., et al, FEBS Lett 1993; 334:210).

The assay was performed in 200 uL 50 mM Tris/HCl buffer, pH 7.4, including 25 mM $MnCl_2$, 1 mM EDTA and 0.5% (w/v) BSA in polypropylene microtiter plates. Membranes containing 0.5 ug protein were incubated for 2 h at 20° C. with 8 pM [$^{125}$I]ET-1 (4000 cpm) and increasing concentrations of unlabelled antagonists. Maximum and minimum binding were estimated in samples without and with 100 nM ET-1, respectively. After two h, the membranes were filtered on, filterplates containing GF/C filters (Unifilterplates from Canberra Packard S. A. Zürich, Switzerland). To each well, 50 uL of scintillation cocktail was added (MicroScint 20, Canberra Packard S. A. Zürich, Switzerland) and the filter plates counted in a microplate counter (TopCount, Canberra Packard S. A. Zürich, Switzerland).

All the test compounds were dissolved, diluted and added in DMSO. The assay was run in the presence of 2.5% DMSO which was found not to interfere significantly with the binding. $IC_{50}$ was calculated as the concentration of antagonist inhibiting 50% of the specific binding of ET-1. For reference compounds, the following $IC_{50}$ values were found: $ET_A$ cells: 0.075 nM (n=8) for ET-1 and 118 nM (n=8) for ET-3; $ET_B$ cells: 0.067 nM (n=8) for ET-1 and 0.092 nM (n=3) for ET-3.

The $IC_{50}$ values obtained with compounds of formula I are given in Table 1

TABLE 1

| Compound of Example | $IC_{50}$[nM] $ET_A$ | $ET_B$ |
|---|---|---|
| Example 2 | 1960 | 1790 |
| Example 5 | 5560 | 356 |
| Example 6 | 8300 | 420 |
| Example 7 | 63.6 | 15.8 |
| Example 8 | 160 | 130 |
| Example 10 | 67.2 | 193 |
| Example 11 | 5110 | 4.3 |
| Example 12 | 2120 | 73.3 |
| Example 13 | 885 | 69.2 |
| Example 14 | 518 | 451 |
| Example 15 | 1320 | 7.3 |
| Example 16 | 261 | 24.5 |
| Example 17 | 1100 | 117 |
| Example 18 | 209 | 1050 |
| Example 21 | 881 | 21.8 |
| Example 23 | 76.1 | 52.7 |
| Example 27 | 3634 | 995 |
| Example 28 | 3709 | 1043 |
| Example 29 | 1253 | 235 |
| Example 30 | 484 | 288 |
| Example 31 | 409 | 735 |
| Example 36f | 478 | 1212 |
| Example 36g | 121 | 93 |
| Example 37 | 5683 | 604 |
| Example 38 | 80 | 84 |
| Example 39 | 1048 | 81 |
| Example 40 | 76 | 87 |
| Example 41 | 4898 | 299 |
| Example 42 | 587 | 99 |
| Example 43 | 75 | 376 |

TABLE 1-continued

| Compound of Example | IC$_{50}$[nM] ET$_A$ | ET$_B$ |
|---|---|---|
| Example 44 | 119 | 323 |
| Example 45 | 251 | 336 |
| Example 46 | 140 | 103 |
| Example 49 | 1027 | 274 |
| Example 51 | 3450 | 182 |
| Example 54 | 2407 | 603 |
| Example 57 | 1625 | 208 |
| Example 58 | 724 | 447 |
| Example 59 | 103 | 189 |
| Example 60 | 1442 | 16 |
| Example 61 | 92 | 183 |
| Example 62 | 443 | 163 |
| Example 68 | 477 | 169 |
| Example 70 | 282 | 2071 |
| Example 71 | 508 | 231 |
| Example 72 | 153 | 279 |
| Example 73 | 233 | 542 |
| Example 74 | 531 | 934 |
| Example 77 | 185 | 5402 |
| Example 78 | 627 | 5458 |
| Example 79 | 37 | >10000 |
| Example 80 | 14.8 | 59.4 |
| Example 81 | 104 | 1240 |
| Example 82 | 311 | 3510 |
| Example 87 | 48.1 | 33.1 |
| Example 88 | 14.8 | 1.86 |
| Example 89 | 1591 | 101 |
| Example 90 | 86 | 4.1 |
| Example 91 | 45.5 | 103 |
| Example 92 | 82.1 | 15 |
| Example 93 | 22.2 | 3.86 |
| Example 94 | 77.3 | 18.6 |

2) Inhibition of Endothelin-induced Contractions on Isolated Rat Aortic Rings (ET$_A$ Receptors) and Rat Tracheal Rings (ET$_B$ Receptors)

The functional inhibitory potency of the endothelin antagonists was assessed by their inhibition of the contraction induced by endothelin-1 on rat aortic rings (ET$_A$ receptors) and of the contraction induced by sarafotoxin S6c on rat tracheal rings (ET$_B$ receptors). Adult Wistar rats were anesthetized and exsanguinated. The thoracic aorta or trachea were excised, dissected and cut in 3–5 mm rings. The endothelium/epithelium was removed by gentle rubbing of the intimal surface. Each ring was suspended in a 10 ml isolated organ bath filled with Krebs-Henseleit solution (in mM; NaCl 115, KCl 4.7, MgSO$_4$ 1.2, KH$_2$PO$_4$ 1.5, NaHCO$_3$ 25, CaCl$_2$ 2.5, glucose 10) kept at 37° and gassed with 95% O$_2$ and 5% CO$_2$. The rings were connected to force transducers and isometric tension was recorded (EMKA Technologies SA, Paris, France). The rings were stretched to a resting tension of 3 g (aorta) or 2 g (trachea). Cumulative doses of ET-1 (aorta) or sarafotoxin S6c (trachea) were added after a 10 min incubation with the test compound or its vehicle. The functional inhibitory potency of the test compound was assessed by calculating the concentration ratio, i.e. the shift to the right of the EC$_{50}$ induced by different concentrations of test compound. EC$_{50}$ is the concentration of endothelin needed to get a half-maximal contraction, pA$_2$ is the negative logarithm of the antagonist concentration which induces a two-fold shift in the EC$_{50}$ value.

The pA$_2$ values obtained with compounds of formula I are given in Table 2.

TABLE 2

| Compound of Example | pA$_2$ value ET$_A$ | ET$_B$ |
|---|---|---|
| Example 7 | 6.08 | 7.15 |
| Example 10 | 6.73 | 5.9 |
| Example 11 | <5 | 7.46 |
| Example 12 | 6.07 | 6.29 |
| Example 15 |  | 7.39 |
| Example 16 | <5.5 | 7.46 |
| Example 55 | 6.2 | 6.3 |
| Example 59 | 6.61 | 5.58 |
| Example 60 |  | 7.3 |
| Example 61 | 7.02 | 6.36 |
| Example 70 | 6.05 |  |
| Example 87 | 6.52 |  |
| Example 88 | 6.16 | 7.95 |

Because of their ability to inhibit the endothelin binding, the described compounds can be used for treatment of diseases which are associated with an increase in vasoconstriction, proliferation or inflammation due to endothelin. Examples of such diseases are hypertension, coronary diseases, cardiac insufficiency, renal and myocardial ischemia, renal failure, cerebral ischemia, dementia, migraine, subarachnoidal hemorrhage, Raynaud's syndrome, portal hypertension and pulmonary hypertension. They can also be used for atherosclerosis, prevention of restenosis after balloon or stent angioplasty, inflammation, stomach and duodenal ulcer, cancer, prostatic hypertrophy, erectile dysfunction, hearing loss, amaurosis, chronic bronchitis, asthma, gram negative septicemia, shock, sickle cell anemia, glomerulonephritis, renal colic, glaucoma, therapy and prophylaxis of diabetic complications, complications of vascular or cardiac surgery or after organ transplantation, complications of cyclosporin treatment, as well as other diseases presently known to be related to endothelin.

The compounds can be administered orally, rectally, parenterally, e.g. by intravenous, intramuscular, subcutaneous, intrathecal or transdermal administration or sublingually or as ophthalmic preparation or administered as aerosol. Examples of applications are capsules, tablets, orally administered suspensions or solutions, suppositories, injections, eye-drops, ointments or aerosols/nebulizers.

Preferred applications are intravenous, intramuscular, or oral administrations as well as eye drops. The dosage used depends upon the type of the specific active ingredient, the age and the requirements of the patient and the kind of application. Generally, dosages of 0.1–050 mg/kg body weight per day are considered. The preparations with compounds can contain inert or as well pharmacodynamically active excipients. Tablets or granules, for example, could contain a number of binding agents, filling excipients, carrier substances or diluents.

The present invention relates to bis-sulfonamides of the general formula I,

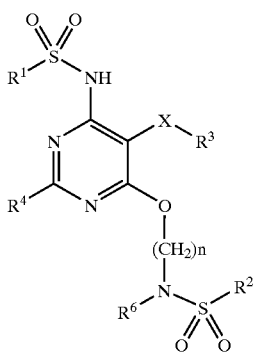

general formula I wherein
R¹ represents aryl; aryl-lower alkyl; aryl-lower alkenyl; heteroaryl; heteroaryl-lower alkyl;
R² represents lower alkyl; trifluoromethyl; lower alkoxy-lower alkyl; lower alkenyl; lower alkynyl; aryl; aryl-lower alkyl; aryl-lower alkenyl; heterocyclyl; heterocyclyl-lower alkyl; heteroaryl; heteroaryl-lower alkyl; cycloalkyl; cycloalkyl-lower alkyl;
R³ represents phenyl; mono-, di- or tri-substituted phenyl substituted with lower alkyl, lower alkenyl, lower alkynyl, lower alkyloxy, amino, lower alkylamino, amino-lower alkyl, trifluoromethyl, trifluoromethoxy, halogen, lower alkylthio, hydroxy, hydroxy-lower alkyl, cyano, carboxyl, lower alkanoyl, formyl; benzofuranyl; aryl; heteroaryl;
R⁴ represents hydrogen; halogen; trifluoromethyl; lower alkyl; lower alkyl-amino; lower alkyloxy; lower alkyl-sulfono; lower alkyl-sulfinyl; lower alkylthio; lower alkylthio-lower alkyl; hydroxy-lower alkyl; lower alkyl-oxy-lower alkyl; hydroxy-lower alkyl-oxy-lower alkyl; hydroxy-lower alkyl-amino; lower alkyl-amino-lower alkyl, amino; di-lower alkyl-amino; [N-(hydroxy-lower alkyl)-N-(lower alkyl)]-amino; aryl; aryl-amino; aryl-lower alkyl-amino; aryl-thio; aryl-lower alkyl-thio; aryloxy; aryl-lower alkyl-oxy; aryl-lower alkyl; aryl-sulfinyl; heteroaryl; heteroaryl-oxy; heteroaryl-lower alkyl-oxy; heteroaryl-amino; heteroaryl-lower alkyl-amino; heteroaryl-thio; heteroaryl-lower alkyl-thio; heteroaryl-lower alkyl; heteroaryl-sulfinyl; heterocyclyl; heterocyclyl-lower alkyl-oxy; heterocyclyl-oxy; heterocyclyl-amino; heterocyclyl-lower alkyl-amino; heterocyclyl-thio; heterocyclyl-lower alkyl-thio; heterocyclyl-lower alkyl; heterocyclyl-sulfinyl; cycloalkyl; cycloalkyl-oxy; cycloalkyl-lower alkyl-oxy; cycloalkyl-amino; cycloalkyl-lower alkyl-amino; cycloalkyl-thio; cycloalkyl-lower alkyl-thio; cycloalkyl-lower alkyl; cycloalkyl-sulfinyl;
R⁶ represents hydrogen; lower alkyl; cycloalkyl; heterocyclyl; heteroaryl; aryl; cycloalkyl-lower alkyl; heterocyclyl-lower alkyl; heteroaryl-lower alkyl; aryl-lower alkyl; lower alkoxy-lower alkyl; lower alkyl-thio-lower alkyl; lower alkyl-amino-lower alkyl; lower alkenyl; lower alkynyl;
n represents the numbers 2, 3, 4 and 5;
X represents oxygen; sulfur; NH; CH₂ or a bond;
and pure diastereomers, mixtures of diastereomers, diastereomeric racemates, mixtures of diastereomeric racemates and the meso-forms and pharmaceutically acceptable salts thereof.

In the definitions of the general formula I—if not otherwise stated—the expression lower means straight and branched chain groups with one to seven carbon atoms, preferably 1 to 4 carbon atoms. Examples of lower alkyl and lower alkoxy groups are methyl, ethyl, n-propyl, isopropyl, n-butyl, isobutyl, sec.-butyl, tert.-butyl, pentyl, hexyl, heptyl, methoxy, ethoxy, propoxy, butoxy, iso-butoxy, sec.-butoxy and tert.-butoxy. Lower alkylendioxy-groups are preferably methylen-dioxy, ethylen-dioxy, propylen-dioxy and butylen-dioxy-groups. Examples of lower alkanoyl-groups are acetyl, propanoyl and butanoyl. Lower alkenylen means e.g.vinylen, propenylen and butenylen. Lower alkenyl and lower alkynyl means groups like ethylen, propylen, butylen, 2-methyl-propenyl, and ethinylen, propinylen, butinylen, pentinylen, 2-methyl-pentinylen etc. Lower alkenyloxy means allyloxy, vinyloxy, propenyloxy and the like. The expression cycloalkyl means a saturated cyclic hydrocarbon ring with 3 to 7 carbon atoms, e.g. cyclopropyl, cyclobutyl, cyclopentyl, cyclohexyl and cycloheptyl, which may be substituted with lower alkyl, hydroxy-lower alkyl, amino-lower alkyl, lower alkoxy-lower alkyl and lower alkenylen groups. The expression heterocyclyl means saturated or unsaturated (but not aromatic) four, five-, six- or seven-membered rings containing one or two nitrogen, oxygen or sulfur atoms which may be the same or different and which rings may be substituted with lower alkyl, amino, nitro, hydroxy, lower alkoxy, e.g. piperidinyl, morpholinyl, piperazinyl, tetrahydropyranyl, dihydropyranyl, 1,4-dioxanyl, pyrrolidinyl, tetrahydrofuranyl, dihydropyrrolyl, dihydroimidazolyl, dihydropyrazolyl, pyrazolidinyl etc. and substituted derivatives of such rings with substituents as outlined above. The expression heteroaryl means six-membered aromatic rings containing one to four nitrogen atoms, benzofused six-membered aromatic rings containing one to three nitrogen atoms, five-membered aromatic rings containing one oxygen or one nitrogen or one sulfur atom, benzo-fused five-membered aromatic rings containing one oxygen or one nitrogen or one sulfur atom, five membered aromatic rings containig an oxygen and nitrogen atom and benzo fused derivatives thereof, five membred aromatic rings containing a sulfur and a nitrogen atom and benzo fused derivatives thereof, five-membered aromatic rings containing two nitrogen atoms and benzo fused derivatives thereof, five membered aromatic rings containing three nitrogen atoms and benzo fused derivatives thereof or the tetrazolyl ring e.g. furanyl, thienyl, pyrrolyl, pyridinyl, indolyl, quinolinyl, isoquinolinyl, imidazolyl, triazinyl, thiazinyl, thiazolyl, isothiazolyl, pyridazinyl, oxazolyl, isoxazolyl, etc. whereby such rings may be substituted with lower alkyl, lower alkenyl, amino, amino-lower alkyl, halogen, hydroxy, lower alkoxy, trifluoromethoxy or trifluoromethyl. The expression aryl represents unsubstituted as well as mono-, di- or tri-substituted aromatic rings with 6 to 10-carbon atoms like phenyl or naphthyl rings which may be substituted with aryl, halogen, hydroxy, lower alkyl, lower alkenyl, lower alkynyl, lower alkoxy, lower alkenyloxy, lower alkynyl-lower alkyl-oxy, lower alkenylen, lower alkylenoxy, lower alkylenoxy or lower alkylendioxy forming with the phenyl ring a five- or six-membered ring, hydroxy-lower alkyl, hydroxy-lower alkenyl, hydroxy-lower alkyl-lower alkynyl, lower alkyloxy-lower alkyl, lower alkyloxy-lower alkyloxy, trifluoromethyl, trifluoromethoxy, cycloalkyl, hydroxy-cycloalkyl, heterocyclyl, heteroaryl.

Especially preferred compounds are compounds of formula I wherein R³ represents phenyl or mono-substituted phenyl substituted with lower alkyloxy, especially methoxy, X represents oxygen and n represents the numbers 2 or 3.

A second group of especially preferred compounds of formula I are the compounds wherein $R^3$ represents phenyl or monosubstituted phenyl substituted with lower alkyl, especially methyl, or lower alkoxy, especially methoxy, X represents a bond and n represents the numbers 2 or 3.

The expression pharmaceutically acceptable salts encompasses either salts with inorganic acids or organic acids like hydrohalogenic acids, e.g. hydrochloric or hydrobromic acid; sulfuric acid, phosphoric acid, nitric acid, citric acid, formic acid, acetic acid, maleic acid, tartaric acid, methylsulfonic acid, p-toluolsulfonic acid and the like or in case the compound of formula I is acidic in nature with an inorganic base like an alkali or earth alkali base, e.g. sodium hydroxide, potassium hydroxide, calcium hydroxide etc. The compounds of the general formula I have one or more asymmetric carbon atoms and may be prepared in form of optically pure enantiomers or diastereomers, mixtures of enantiomers or diastereomers, diastereomeric racemates, mixtures of diastereomeric racemates and also in the mesoform. The present invention encompasses all these forms. Mixtures may be separated in a manner known per se, i.e. by column chromatography, thin layer chromatography, HPLC, crystallization etc.

Because of their ability to inhibit the endothelin binding, the described compounds of the general formula I and their pharmaceutically acceptable salts may be used for treatment of diseases which are associated with an increase in vasoconstriction, proliferation or inflammation due to endothelin. Examples of such diseases are hypertension, coronary diseases, cardiac insufficiency, renal and myocardial ischemia, renal failure, cerebral ischemia, dementia, migraine, subarachnoidal hemorrhage, Raynaud's syndrome, portal hypertension and pulmonary hypertension. They can also be used for atherosclerosis, prevention of restenosis after balloon or stent angioplasty, inflammation, stomach and duodenal ulcer, cancer, prostatic hypertrophy, erectile dysfunction, hearing loss, amaurosis, chronic bronchitis, asthma, gram negative septicemia, shock, sickle cell anemia, glomerulonephritis, renal colic, glaucoma, therapy and prophylaxis of diabetic complications, complications of vascular or cardiac surgery or after organ transplantation, complications of cyclosporin treatment, as well as other diseases presently known to be related to endothelin.

These compositions may be administered in enteral or oral form e.g. as tablets, dragees, gelatine capsules, emulsions, solutions or suspensions, in nasal form like sprays or rectically in form of suppositories. These compounds may also be administered in intramuscular, parenteral or intraveneous form, e.g. in form of injectable solutions.

These pharmaceutical compositions may contain the compounds of formula I as well as their, pharmaceutically acceptable salts in combination with inorganic and/or organic excipients which are usual in the pharmaceutical industry like lactose, maize or derivatives thereof, talcum, stearinic acid or salts of these materials.

For gelatine capsules vegetable oils, waxes, fats, liquid or half-liquid polyols etc. may be used. For the preparation of solutions and sirups e.g. water, polyols, saccharose, glucose etc. are used. Injectables are prepared by using e.g. water, polyols, alcohols, glycerin, vegetable oils, lecithin, liposomes etc. Suppositories are prepared by using natural or hydrogenated oils, waxes, fatty acids (fats), liquid or half-liquid polyols etc.

The compositions may contain in addition preservatives, stabilisation improving substances, viscosity improving or regulating substances, solubility improving substances, sweeteners, dyes, taste improving compounds, salts to change the osmotic pressure, buffer, anti oxidants etc.

The compounds of formula I may also be used in combination with one or more other therapeutically useful substances e.g. α- and β-blockers like Phentolamine, Phenoxybenzamine, Atenolol, Propranolol, Timolol, Metoprolol, Carteolol etc.; Vasodilators like Hydralazine, Minoxidil, Diazoxide, Flosequinan etc.; Calcium-antagonists like Diltiazem, Nicardipine, Nimodipine, Verapamil, Nifedipine etc.; ACE-inhibitors like Cilazapril, Captopril, Enalapril, Lisinopril etc.; Potassium activators like Pinacidil etc. Angiotensin II antagonists; Diuretics like Hydrochlorothiazide, Chlorothiazide, Acetolamide, Bumetanide, Furosemide, Metolazone, Chlortalidone etc.; Sympatholitics like Methyldopa, Clonidine, Guanabenz, Reserpine etc.; and other therapeutics which serve to treat high blood pressure or any cardiac disorders.

The dosage may vary within wide limits but should be adapted to the specific situation. In general the dosage given in oral form should daily be between about 3 mg and about 3 g, preferably between about 10 mg and about 1 g, especially preferred between 5 mg and 300 mg, per adult with a body weight of about 70 kg. The dosage should be administered preferably in 1 to 3 doses per day which are of equal weight. As usual children should receive lower doses which are adapted to body weight and age.

Preferred compounds are compounds of formula II

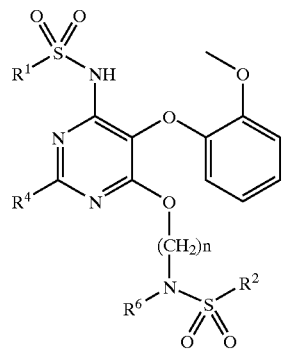

formula II wherein $R^1$, $R^2$, $R^4$, $R^6$ and n are as defined in formula I above, and pharmaceutically acceptable salts of compounds of formula II.

Especially preferred compounds among the group of compounds of formula II are those wherein $R^6$ represents hydrogen or lower alkyl.

Also preferred are compounds of formula III

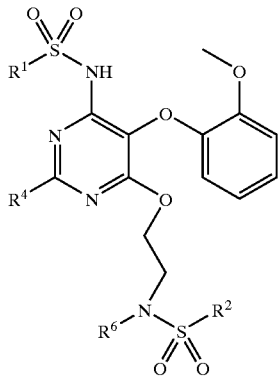

formula III wherein $R^1$, $R^2$, $R^4$ and $R^6$ are as defined in formula I above, and pharmaceutically acceptable salts of compounds of formula III.

Especially preferred compounds among the group of compounds of formula III are those wherein $R^6$ represents hydrogen or lower alkyl.

Also preferred are compounds of formula IV

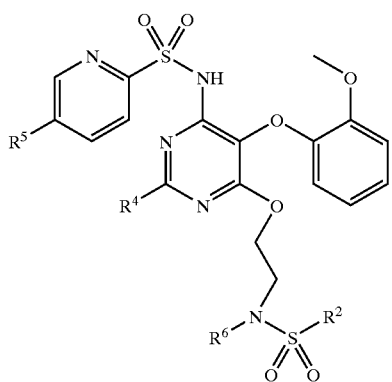

formula IV wherein $R^2$, $R^4$ and $R^6$ are as defined in formula I above and $R^5$ represents hydrogen, methyl or isopropyl, and pharmaceutically acceptable salts of compounds of formula IV.

Especially preferred compounds among the group of compounds of formula IV are those wherein $R^6$ represents hydrogen or lower alkyl.

Another preferred group of compounds are compounds of formula V

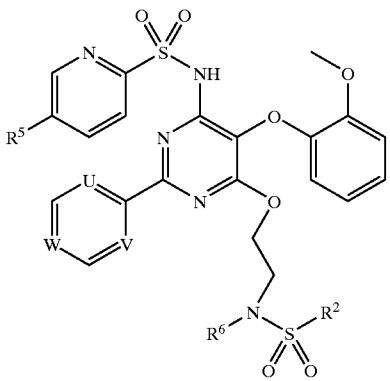

formula V wherein $R^5$ is as defined in formula IV above, $R^2$ and $R^6$ are as defined in formula I above, U and V represent nitrogen and W represents carbon, or U and V represent carbon and W represents nitrogen, and pharmaceutically acceptable salts thereof.

Especially preferred compounds among the group of compounds of formula V are those wherein $R^6$ represents hydrogen or lower alkyl.

Another preferred group of compounds are compounds of formula VI

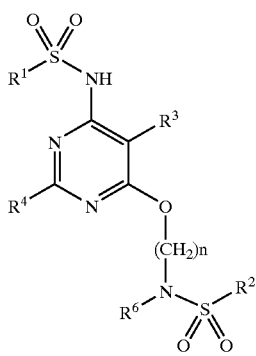

formula VI wherein $R^1$, $R^2$, $R^3$, $R^4$, $R^6$ and n are as defined in formula I above, and pharmaceutically acceptable salts of compounds of formula VI.

Especially preferred compounds among the group of compounds of formula VI are those wherein $R^6$ represents hydrogen or lower alkyl.

Another preferred group of compounds are compounds of formula VII

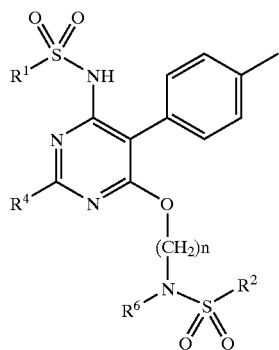

formula VII wherein $R^1$, $R^2$, $R^4$, $R^6$ and n are as defined in formula I above,
and pharmaceutically acceptable salts of compounds of formula VII.

Especially preferred compounds among the group of compounds of formula VII are those wherein $R^6$ represents hydrogen or lower alkyl.

Preferred compounds are:

p-tert.-butyl-N-[6-(ethoxy-2-(2-thiophenesulfonamido))-5-(o-methoxyphenoxy)-2-(2-pyrimidinyl)-4-pyrimidinyl]benzene-sulfonamide, 5-i.-propyl-N-[6-(ethoxy-2-(2-propanesulfonamido))-5-(o-methoxyphenoxy)2-(4-pyridyl)-4-pyrimidinyl]pyridine-2-sulfonamide, 5-i.-propyl-N-[6-(ethoxy-2-(4-methylbenzenesulfonamido))-5-(o-methoxyphenoxy)-2-(3,4,5-trimethoxyphenyl)-4-pyrimidinyl]pyridine-2-sulfonamide, 5-i.-propyl-N-[6-(ethoxy-2-(4-methylbenzenesulfonamido)5-(o-methoxyphenoxy)-2-(4-pyridyl)-4-pyrimidinyl]pyridine-2-sulfonamide, 5-i.-propyl-N-[6-(ethoxy-2-benzenesulfonamido)-5-(o-methoxyphenoxy)-2-(4-pyridyl)-4-pyrimidinyl]pyridine-2-sulfonamide, 5-i.-propyl-N-[6-(ethoxy-2-thiophenesulfonamido)-5-(o-methoxyphenoxy)-2-(3,4,5-trimethoxyphenyl)-4-pyrimidinyl]pyridine-2-sulfonamide, 5-i.-propyl-N-[6-(ethoxy-2-(1-propanesulfonamido))-5-(o-methoxyphenoxy)-2-(3,4,5-trimethoxyphenyl)-4-pyrimidinyl]pyridine-2-sulfonamide, p-tert.-butyl-N-[6-(ethoxy-2-(1-butanesulfonamido))-5-(o-methoxyphenoxy)-2-(2-pyrimidinyl)-4-pyrimidinyl]benzene-sulfonamide, 5-i.-propyl-N-[6-(ethoxy-2-p-toluenesulfonamido)-5-(o-methoxyphenoxy)-2-methyl-4-pyrimidinyl]pyridine-2-sulfonamide, 5-i.-propyl-N-[6-(ethoxy-2-methanesulfonamido)-5-(o-methoxyphenoxy)-2-methyl4-pyrimidinyl]pyridine-2-sulfonamide, 4-tert.-butyl-N-[6-(2-ethanesulfonylamino-ethoxy)-2-methanesulfonyl-5-(o-methoxyphenoxy-pyrimidin-4-yl]-benzenesulfonamide, 5-i-propyl-N-[6-chloro-5-(o-methoxyphenoxy)-2-cyclopropyl-pyrimidin-4-yl]-pyridine-2-sulfonamide, 5-i-propyl-N-[6-(2-(4-methylbenzene)-sulfonylamino-ethoxy)-5-(o-methoxyphenoxy)-2-cyclopropyl-pyrimidin-4-yl]-pyridine-2-sulfonamide, 4-tert.-butyl-N-[6-(2-(2-propane)-sulfonylamino-ethoxy)-5-(o-methoxyphenoxy)-2-cyclopropyl-pyrimidin-4-yl]-benzene-sulfonamide, 5-isopropyl-N-[6-(2-(2-thiophensulfonyl)-amino-ethoxy)-5-(o-methoxyphenoxy)-2-(N-morpholino)-4-pyrimidinyl]-2-pyridine sulfonamide, 5-i-propyl-N-[6-(2-ethanesulfonylamino-ethoxy)-5-(o-methoxyphenoxy)-2-cyclopropyl-pyrimidin-4-yl]-pyridine-2-sulfonamide, 5-isopropyl-N-[6-(2-propanesulfonylamino-ethoxy)-5-(o-methoxyphenoxy)-2-(N-morpholino)-4-pyrimidinyl]-2-pyridine sulfonamide, 5-methyl-N-[6-(2-(1-propanesulfonylamino)-ethoxy)-5-(o-methoxyphenoxy)-2-(N-morpholino)-4-pyrimidinyl]-2-pyridine sulfonamide, 5-isopropyl-N-[6-(2-(4-methylbenzenesulfonylamino)-ethoxy)-5-(o-methoxyphenoxy)-2-(N-morpholino)-4-pyrimidinyl]-2-pyridine sulfonamide, and pharmaceutically acceptable salts thereof.

Particularly preferred compounds are p-tert.-butyl-N-[6-(ethoxy-2-(2-thiophenesulfonamido))-5-(o-methoxyphenoxy)-2-(2-pyrimidinyl)-4-pyrimidinyl]benzene-sulfonamide, 5-i.-propyl-N-[6-(ethoxy-2-(4-methylbenzenesulfonamido))-5-(o-methoxyphenoxy)-2-(3,4,5-trimethoxyphenyl)-4-pyrimidinyl]pyridine-2-sulfonamide, 5-i.-propyl-N-[6-(ethoxy-2-thiophenesulfonamido)-5-(o-methoxyphenoxy)-2-(3,4,5-trimethoxyphenyl)-4-pyrimidinyl]pyridine-2-sulfonamide, 5-isopropyl-N-[6-(2-(4-methylbenzenesulfonylamino)-ethoxy)-5-(o-methoxyphenoxy)-2-(N-morpholino)-4-pyrimidinyl]-2-pyridine sulfonamide, 5-isopropyl-N-[6-(2-(ethanesulfonylamino)-ethoxy)-5-(o-methoxyphenoxy)-2-(N-morpholino)-4-pyrimidinyl]-2-pyridine sulfonamide 5-isopropyl-N-[6-(2-(ethanesulfonylamino)-ethoxy)-5-(o-methoxyphenoxy)-2-(N-morpholino)-4-pyrimidinyl]-2-pyridine sulfonamide 4-tert.-butyl-N-[6-(3-(ethanesulfonylamino)-propoxy)5-(o-methoxyphenoxy)-2-pyrimidinyl-4-pyrimidinyl]-benzene-sulfonamide 4-tert.-butyl-N-[6-(3-(2-thiophenesulfonylamino)-propoxy)-5-(o-methoxyphenoxy)-2-pyrimidinyl-4-pyrimidinyl]-benzene-sulfonamide 4-tert.-butyl-N-[6-(3-(ethanesulfonylamino)-propoxy)-5-(o-methoxyphenoxy)-2-cyclopropyl-4-pyrimidinyl]-benzene-sulfonamide 4-tert.-butyl-N-[6-(3-(2-thiophenesulfonylamino)-propoxy)-5-(o-methoxyphenoxy)-2-cyclopropyl-4-pyrimidinyl]-benzene-sulfonamide 5-i.-propyl-N-[6-(3-(propanesulfonylamino)-propoxy)-5-(o-methoxyphenoxy)-2-cyclopropyl-4-pyrimidinyl]-pyridine-2-sulfonamide 5-i.-propyl-N-[6-(3-(2-thiophenesulfonylamino)-propoxy)-5-(o-methoxyphenoxy)-2-cyclopropyl-4-pyrimidinyl]-pyridine-2-sulfonamide 5-i.-propyl-N-[6-(3-(p-toluenesulfonylamino)-propoxy)5-(o-methoxyphenoxy)-2-cyclopropyl-4-pyrimidinyl]-pyridine-2-sulfonamide and pharmaceutically acceptable salts thereof.

The invention also relates to a process for the manufacture of compounds of the general formula I:

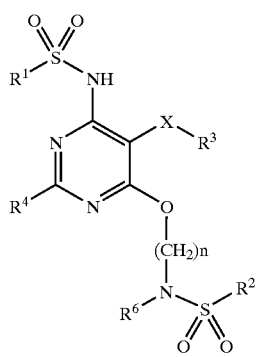

general formula I wherein $R^1$, $R^2$, $R^4$, $R^6$, X and n have the meaning given in formula I above,
which process comprises
a) for obtaining compounds wherein $R^6$ represents hydrogen, reacting a compound of formula VIII

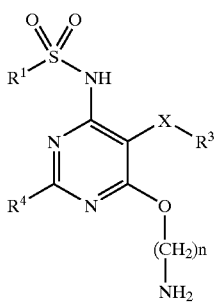

formula VIII wherein $R^1$, $R^3$, $R^4$, X and n have the meaning given in formula I above,
with a compound of the formula Cl—$SO_2$—$R^2$, wherein $R^2$ has the meaning given in formula I above, or
b) by reacting a compound of formula IX

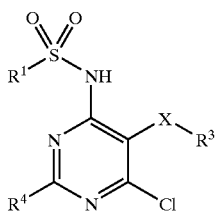

formula IX wherein $R^1$, $R^3$, $R^4$ and X have the meaning given in formula I above, with a compound of formula X

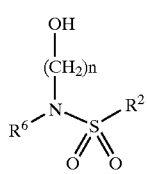

formula X wherein $R^2$, $R^6$ and n have the meaning given in formula I above,
and, as the case may be, resolving a compound with one or more optically active carbon atoms into pure enantiomers or diastereomers, mixtures of enantiomers or diastereomers, diastereomeric racemates, or into the meso-form in a manner known per se.

and, if desired, converting a compound of formula I obtained into a pharmaceutically acceptable salt in a manner known per se.

The above process may be described in more detail as follows:

The compounds of the general formula I of the present invention wherein $R^6$ represents hydrogen, are prepared according to the general sequence of reactions outlined in Scheme 1 below, wherein $R^1$, $R^2$, $R^3$, $R^4$ and n are as defined in formula I above. For simplicity and clarity reasons Scheme I only describes part of the synthetic possibilities which lead to compounds of formula I. The literature references given in brackets [ ] are set forth at the end of this paragraph. The amidines 2 were synthesized applying standard methodology [1] by reaction of the appropriate nitrile 1 either with sodium methylate in methanol followed by addition of ammonium chloride or by reaction with lithium hexamethyldisilazane followed by addidion of hydrochloric acid in i-propanol. The 2-substituted malonic esters 4 were prepared accoring to published procedures [1] by reacting dimethylchloromalonate (3) with the appropriate alcohol 5 in acetone and potassium carbonate as base. The compounds 4 were dissolved in methanol and sodium methylate was added and stirring was continued for about 30 min followed by the addition of an amidine derivative 2. Stirring at ambient temperature was continued for another 8 h. After acidic work up the 4,6-dihydroxypyrimidines 6 could be isolated in yields of 70 to 90% [2]. Compounds 6 or the tautomeric form thereof were transformed into the dichloroderivatives 7 with phosphorous oxychloride at elevated temperatures (60–120° C.) in yields of 40 to 75% [3]. In some cases better yields were obtained by addition of $PCl_5$ or benzyl-triethylammoniumchloride. The dichlorides 7 were reacted with an excess of the appropriate sulfonamide potassium salt 9 (prepared according to standard methodology from the sulfochlorides 8) in DMSO at room temperature to give the pyrimidines 10 in yields of 70 to 90% either after recrystallization from ethyl acetate/diethylether or chromatography over silica gel with ethyl acetate/heptane. The pyrimidine derivatives 10 are the central intermediates which can be transformed to the desired final products by two different pathways. Depending on the nature of $R^1$, $R^3$ and $R^4$ the suitable reaction sequence is chosen. The first possibility to transform 10 into the final products 13 is by reaction with the 1-hydroxy-ω-sulfonamido-alkyl-compounds 12 (prepared from the appropriate 1,ω-aminoalcohol 11 and the sulfochlorides 15 at room temperature in THF) in THF/DMSO=15/1 and potassium tert.-butylate as base at elevated temperatures (60 to 120° C. in yields of 40 to 80%. The second reaction sequence starts with the introduction of the oxy-alkyl-amino side chain by reaction of 10 with the appropriate 1,ω-aminoalcohol 11 in THF/DMF=1/1 and sodium hydride as base to give compounds 14 in yields of 50 to 70% after recrystallization. The alkylamino functionality of 14 was then reacted by standard methodology [4] with the desired sulfochlorides 15 in methylene chloride and Hünig's base to give the target bis-sulfonamides 13 in yields of 40 to 75% after recrystallization from mixtures of methanol/acetonitrile and/or diethyl ether.

Compounds of general formula I wherein $R^1$, $R^2$, $R^3$, $R^4$, X and n are as defined in general formula I above and wherein $R^6$ is as defined in general formula I above but does not represent hydrogen, can be prepared according to Scheme 2. For simplicity and clarity reasons, Scheme 2 only describes part of the synthetic possibilities which lead to compounds of formula I. Compounds 16, prepared according to the description given in Scheme 1 and [5], [6] are reacted with compounds 18 under the same reaction conditions given for the synthesis of compounds 13 to give compounds 19 (which correspond to compounds of general formula I). Compounds 18 are obtained by reacting the aminoalcohol derivatives 17 with the sulfochlorides 15 under the conditions described in Scheme 1. Compounds 17 are either commercially available or can be prepared by standard procedures (reductive amination, alkylation etc) from aminoalcohols or from the hydroxy protected aminoalcohols containing a primary amino group.

[1] W. Göhring, J. Schildknecht, M. Federspiel; *Chimia,* 1996, 50, 538–543

[2] W. Neidhart, V. Breu, D. Bur, K. Burri, M. Clozel, G. Hirth, M. Müller, H. P. Wessel, H. Ramuz; *Chimia,* 1996, 50, 519–524 and references cited there.

[3] W. Neidhart, V. Breu, K. Burri, M. Clozel, G. Hirth, U. Klinkhammer, T. Giller, H. Ramuz; *Bioorg. Med. Chem. Lett.,* 1997, 7, 2223–2228. R. A. Nugent, S. T. Schlachter, M. J. Murphy, G. J. Cleek, T. J. Poel, D. G. Whishka, D. R. Graber, Y. Yagi, B. J. Keiser, R. A. Olmsted, L. A. Kopta, S. M. Swaney, S. M. Poppe, J. Morris, W. G. Tarpley R. C. Thomas; *J. Med. Chem.,* 1998, 41, 3793–3803.

[4] J. March; *Advanced Organic Chemistry,* 4$^{th}$ Ed., 1994, p. 499 and references cited there.

[5] EP 0 743 307 A1; EP 0 658 548 B1; EP 0 959 072 A1 (Tanabe Seiyaku)

[6] EP 0 633 259 B1; EP 0 526 708 A1; WO 96/19459 (F. Hofmann-LaRoche)

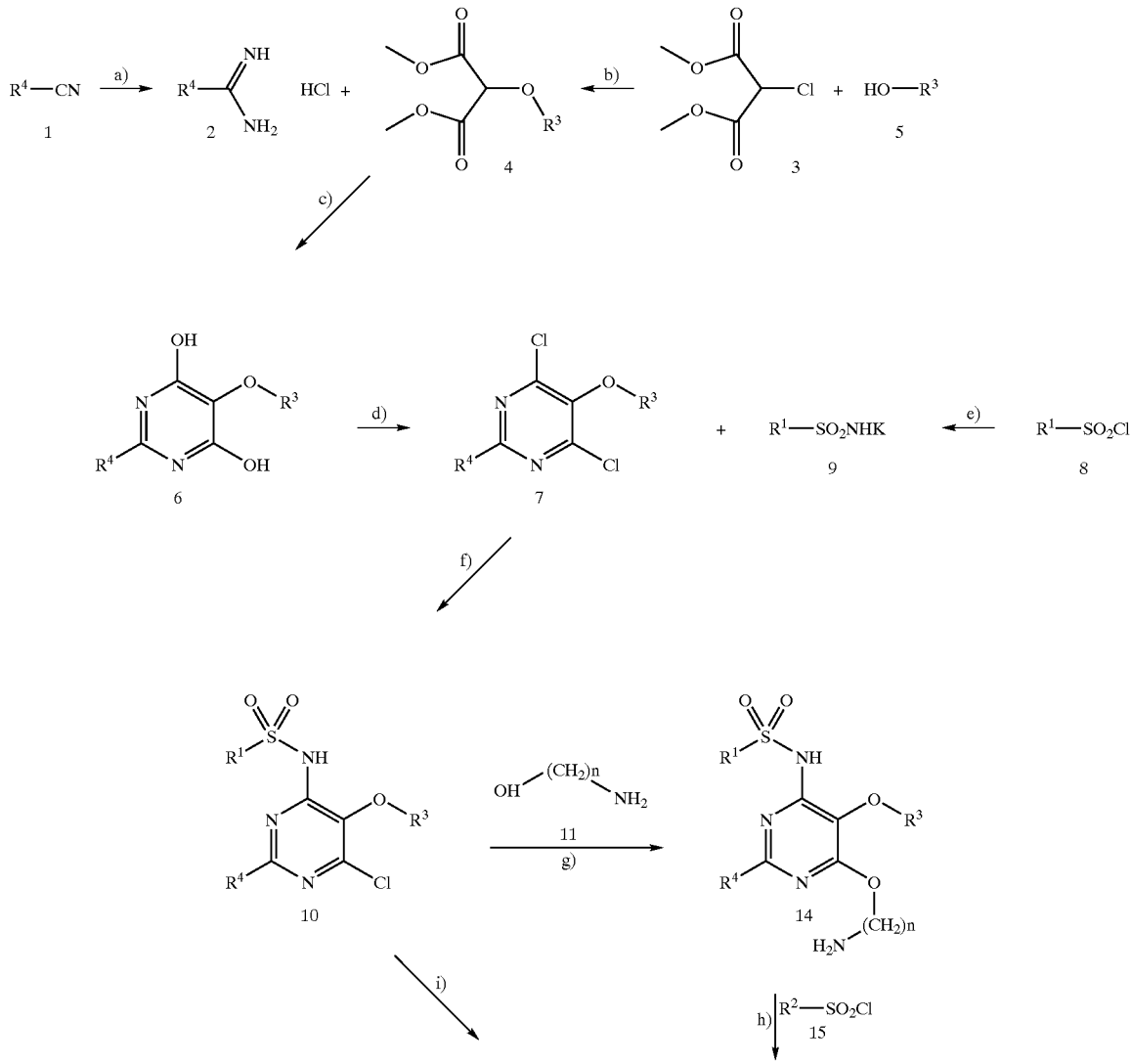

Scheme 1: Preparation of the Bis-sulfonamides

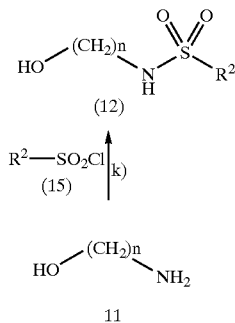

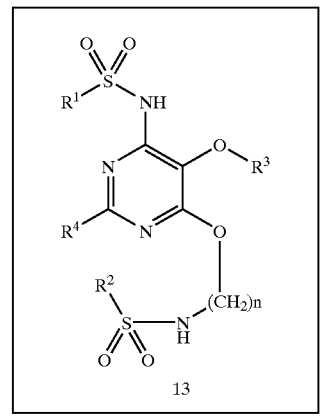

a) NaOMe, MeOH then NH₄Cl or LiN(Si(CH₃)₃)₂ then HCl/i-PrOH; b) K₂CO₃, acetone; c) NaOMe, MeOH; d) POCl₃; e) NH₃/THF then KOtBu, MeOH; f) DMSO; g) NaH, THF, DMF; h) CH₂Cl₂, Hünigs base; i) KOtBu, THF, DMSO; k) THF.

Scheme 2: Preparation of the Bissulfonamides

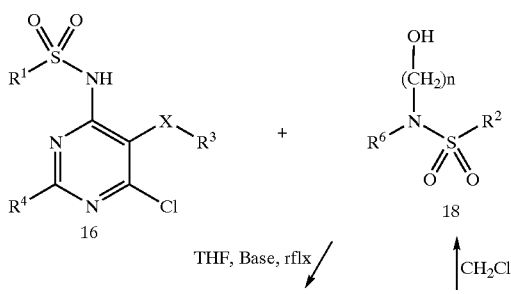

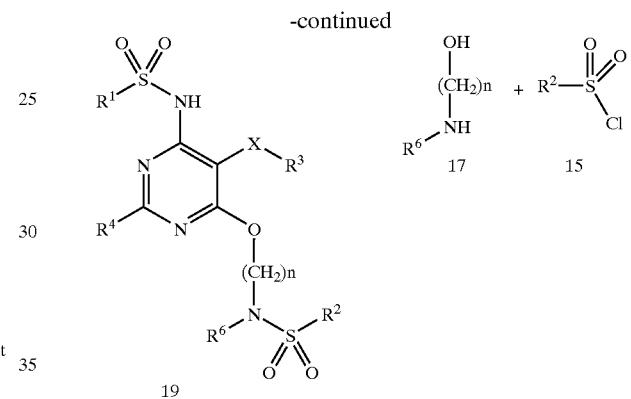

According to the procedures described in [5] and for Schemes 1 and 2 compounds of the general formula I can also be prepared as displayed in Scheme 3 below wherein $R^1, R^2, R^3, R^4, R^6$, X and n are as defined in general formula I:

Scheme 3: Preparation of the Bis-Sulfonamides

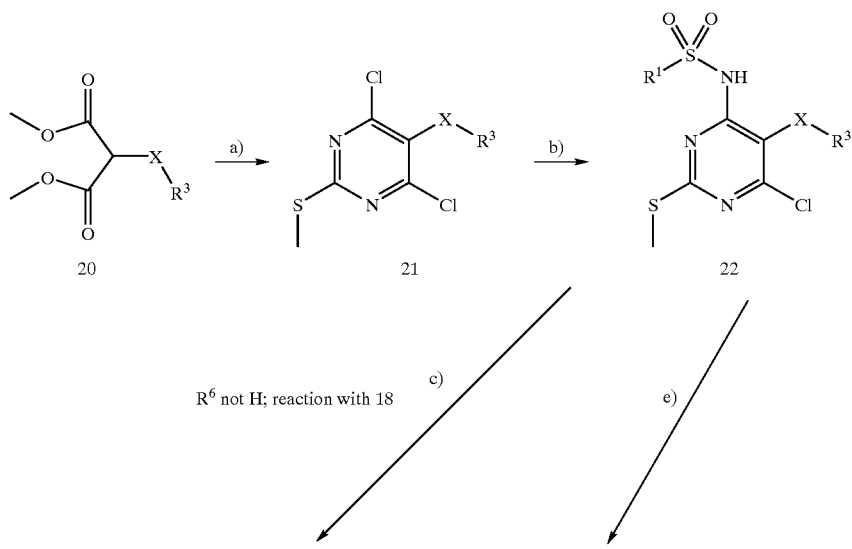

-continued

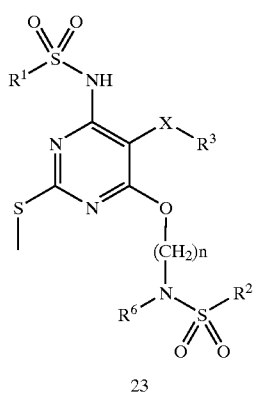

23

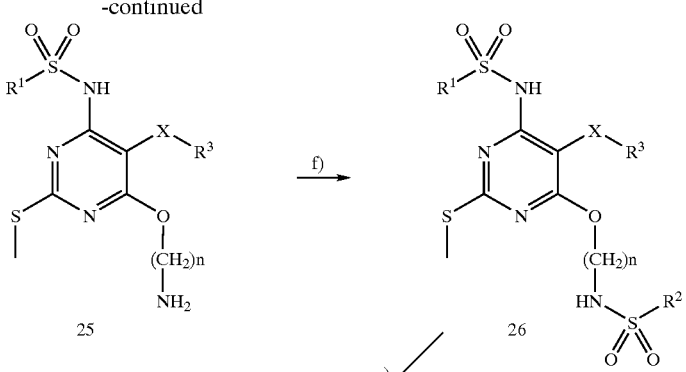

25  26

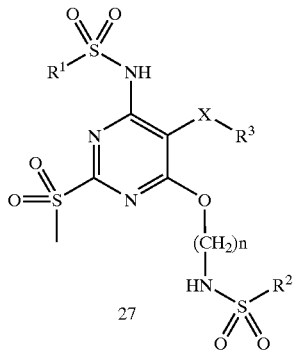

27

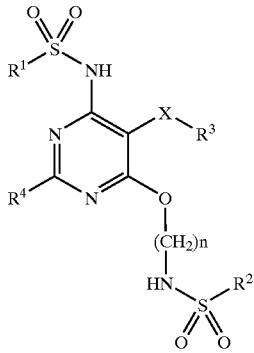

27

24 a) i) thiourea, NaOMe, MeOH, rt; ii) MeI, DMSO, rt; iii) POCl₃, dimethylaniline, 100–120° C.; b) R¹—SO₂—NHK, DMSO, rt c) 18, KOtBu, THF, rflx; d) MCPBA, DCM, rt; ii) for the substitution of the sulfono group see [5]; e) HO—(CH₂)n—NH₂, NaH, THF/DMF, 0° C. to rt; f) R²—SO₂—Cl, base, DCM, rt; g) MCPBA, DCM, rt; h) for the substitution of the sulfono group see [5].

a) i) thiourea, NaOMe, MeOH, rt; ii) MeI, DMSO, rt; iii) POCl₃, dimethylaniline, 100–120° C.; b) R¹—SO₂—NHK, DMSO, rt; c) 18, KOtBu, THF, rflx; d) MCPBA, DCM, rt; ii) for the substitution of the sulfono group see [5]; e) HO—(CH₂)n—NH₂, NaH, THF/DMF, 0° C. to rt; f) R²—SO₂—Cl, base, DCM, rt; g) MCPBA, DCM, rt; h) for the substitution of the sulfono group see [5].

EXAMPLES

The following examples illustrate the invention but do not at all limit the scope thereof. All temperatures are stated in ° C.

The following compounds were prepared according to the procedure described above and shown in Scheme 1. All compounds were characterized by 1H-NMR (300 MHz) and occasionally by 13C-NMR (75 MHz) (Varian Oxford, 300 MHz; chemical shifts are given in ppm relative to the solvent used; multiplicities: s=singlet, d=doublet, t=triplet; m=multiplet), by LC-MS (Waters Micromass; ZMD-platform with ESI-probe with Alliance 2790 HT; Colum: 2×30 mm, Gromsil ODS4, 3 μm, 120A; Gradient: 0–100% acetonitril in water, 6 min, with 0.05% formic acid, flow:

0.45 ml/min; $t_R$ is given in min.), by TLC (TLC-plates from Merck, Silica gel 60 $F_{254}$) and occasionally by melting point.

Example 1 a) 318 mg N-(2-Hydroxy-ethyl)-methanesulfonamide was dissolved in 15 ml THF and 673 mg potassium-tert.-butylate was added. The mixture was heated to reflux for 15 min, then cooled to room temperature and 200 mg of p-methyl-N-[6-chloro-5-(o-methoxyphenoxy)-2-(4-pyridyl)-4-pyrimidinyl]-benzene-sulfonamide followed by 1 ml of DMSO was added and the reaction mixture was heated to reflux for another 8 h. The THF was evaporated and 50 ml of water was added to the residue which was acidified to pH 4 by addition of acetic acid. The product precipitates, was filtered off and recrystallized from methanol/diethylether. 150 mg of p-methyl-N-[6-(ethoxy-2-methanesulfonamido)-5-(o-methoxyphenoxy)-2-(4-pyridyl)-4-pyrimidinyl]-benzenesulfonamide was obtained as a yellow solid. $R_f$ (EA/cyHex=3/1)=0.311; $t_R$=4.94 (LC); $M^+$=586.55 (ES+); $M^+$=584.45 (ES−)

b) To a solution of 0.23 g sodium in 40 ml methanol was added 10.62 g 4-cyanopyridine at room temperature. Stirring was continued for 6 h followed by the addition of 5.9 g ammoniumchloride and stirring was continued for another 10 h. Then 120 ml diethylether was added and the precipitate was filtered off after 30 min and washed once with 20 ml of diethylether. The product was dried under highly reduced pressure. 14.95 g 4-amidino-pyridine hydrochloride was obtained as a white powder.

c) 48 ml 2-methoxy-phenol (guajacol) was slowly added to a stirred suspension of 70.8 g potassium carbonate in 480 ml acetone followed by heating to 45° C. Then 63.2 ml dimethylchloromalonate in 50 ml acetone was added within 20 min. The reaction mixture was heated to reflux for 16 h. The solvent was evaporated under reduced pressure, the residue taken into water and extracted with dichloromethane. The combined organic layers were dried over sodium sulfate and evaporated. The oily product was crystallized from methyl-tert.-butyl-ether. 86 g dimethyl-(o-methoxyphenoxy)malonate was obtained.

d) To a stirred solution of 9.7 g sodium methylate in 100 ml methanol a solution of 21.7 g dimethyl-(o-methoxyphenoxy)malonate in 50 ml methanol was added within 15 min and stirring was continued for 30 min followed by the addition of 15.0 g 4-amidino-pyridine hydrochloride followed by stirring at room temperature for 20 h. The reaction mixture was concentrated in vacuo. The solid residue was stirred with ether. The obtained powder was filtered off and dissolved in 300 ml water. Acetic acid was added to pH=4. The precipitated product was filtered off, washed with water and dried in vacuo at 50° C. 20.1 g 5-(o-methoxyphenoxy)-4,6-dihydroxy-2-(4-pyridyl)-pyrimidine (is possibly also present as the tautomeric 5-(o-methoxyphenoxy)-2-(4-pyridyl)-tetrahydropyrimidine-4,6-dion) was obtained as a white powder.

e) 10 g of the 5-(o-methoxyphenoxy)-4,6-dihydroxy-2-(4-pyridyl)-pyrimidine, 11.2 g N-ethyldiisopropylamine, 11 g tetraethylammoniumchloride and 13.8 g phosphorous pentachloride was dissolved in 25 ml phosphorous oxychloride and heated to reflux for 3 h. The mixture was evaporated in vacuo, toluene was added and the mixture was again evaporated. The residue was taken into dichloromethane and poured onto ice/water. The layers were separated, the organic layer was washed with water, dried over sodium sulfate and evaporated. After recrystallization from acetone, 6.52 g of 5-(o-methoxyphenoxy)-4,6-dichloro-2-(4-pyridyl)-pyrimidine was obtained.

f) 25 g toluene-4-sulfonylchloride was dissolved in 300 ml THF and cooled to 0° C. followed by the addition of 31 ml of 25% aqueous ammonia. After stirring the reaction mixture at room temperature for one hour, the solvent was evaporated and the residue taken into ethyl acetate, washed twice with water, dried over sodium sulfate and evaporated. The white solid obtained was dissolved in 150 ml methanol, 15 g potassium-tert.-butylate was added and stirring continued for 30 min. The reaction mixture was evaporated and dried under highly reduced pressure. 24.9 g p-toluene-sulfonamide potassium salt was obtained as a white powder.

g) 2 g 5-(o-methoxyphenoxy)-4,6-dichloro-2-(4-pyridyl)-pyrimidine was dissolved in 30 ml dry DMSO. 2.40 g p-toluene-sulfonamide potassium salt was added and stirring continued for 20 h. The reaction mixture was poured onto 200 ml water and extracted twice with 200 ml diethylether. The combined organic layers were extracted twice with 50 ml water. The combined water layers were acidified by acetic acid to pH=4. The precipitated product was filtered off, washed with ether and dried under reduced pressure. 1.9 g p-methyl-N-[6-chloro-5-(o-methoxyphenoxy)-2-(4-pyridyl)-4-pyrimidinyl]benzene-sulfonamide was obtained as a slightly colored solid. $R_f$ (EA/Hex=1/1)=0.15.

Example 2

According to Example 1a), 200 mg p-methyl-N-[6-chloro-5-(o-methoxyphenoxy)-2-(4-pyridyl)-4-pyrimidinyl] benzene-sulfonamide (Example 1g) was reacted with 459 mg N-(2-hydroxy-ethyl)-benzenesulfonamide to give 150 mg p-methyl-N-[6-(ethoxy-2-benzenesulfonamido)-5-(o-methoxyphenoxy)-2-(4-pyridyl)-4-pyrimidinyl]benzene-sulfonamide. $R_f$ (EA/cyHex=3/1)=0.574; $t_R$=5.66 (LC); $M^+$=646.52 (ES−).

Example 3

According to Example 1a), 200 mg p-methyl-N-[6-chloro-5-(o-methoxyphenoxy)-2-(4-pyridyl)-4-pyrimidinyl] benzene-sulfonamide (Example 1g) was reacted with 490 mg N-(2-hydroxy-ethyl)-p-toluenesulfonamide to give 130 mg p-methyl-N-[6-(ethoxy-2-p-toluenesulfonamido)-5-(o-methoxyphenoxy)-2-(4-pyridyl)-4-pyrimidinyl]benzene-sulfonamide. $R_f$ (EA/cyHex=3/1)=0.529; $t_R$=5.83 (LC); $M^+$=662.69 (ES+); $M^+$=660.56 (ES−).

Example 4 a) 150 mg p-tert.-butyl-N-[6-(2-aminoethoxy)-5-(o-methoxyphenoxy)-2-(2-pyrimidinyl)-4-pyrimidinyl] benzene-sulfonamide was dissolved in 5 ml dry dichloromethane and 1 ml dry DMF. 150 mg Hünig's base and 100 mg mesylchloride was added and stirring was continued for 12 h. The solvent was evaporated and 20 ml of water was added to the residue. The product precipitated and was filtered off and washed with water. After recrystallization from methanol/diethylether 100 mg of p-tert.-butyl-N-[6-(ethoxy-2-methanesulfonamido)-5-(o-methoxyphenoxy)-2-(2-pyrimidinyl)-4-pyrimidinyl]benzene-sulfonamide as a reddish solid was obtained. $t_R$=5.39 (LC); $M^+$=627.84 (ES−).

b) 1.75 g sodium hydride (55% in mineral oil) was washed twice with dry THF. 8 ml of THF was then added and the mixture was cooled to 0° C. followed by slow addition of 8 ml of abs. ethanolamine in 8 ml of dry THF. The mixture was stirred for 1 hour at room temperature and was then slowly added to a solution of 1 g p-tert.-butyl-N-[6-chloro-5-(o-methoxyphenoxy)-2-(2-pyrimidinyl)-4-pyrimidinyl]benzene-sulfonamide in 11.5 ml dry DMF at 0° C. Stirring was continued at room temperature for 12 h. The reaction mixture was poured onto water and acidified with 25% hydrochloric acid to pH=7. A white solid precipitates; it was filtered off, washed with water and dried at 45° C. under reduced pressure. 690 mg p-tert.-butyl-N-[6-(2-aminoethoxy)-5-(o-methoxyphenoxy)-2-(2-pyrimidinyl)-4-pyrimidinyl]benzene-sulfonamide was obtained as a yellow powder. $R_f$ (EA/cyHex=3/1)=0.389.

c) p-tert.-butyl-N-[6-chloro-5-(o-methoxyphenoxy)-2-(2-pyrimidinyl)-4-pyrimidinyl]benzene-sulfonamide was prepared as disclosed in EP 0 526 708 A1 from 4,6-dichloro-5-(o-methoxyphenoxy)-2-(2-pyrimidinyl)-pyrimidine.

d) 4,6-dichloro-5-(o-methoxyphenoxy)-2-(2-pyrimidinyl)-pyrimidine was prepared as disclosed in EP 0 526 708 A1 from 4,6dihydroxy-5-(o-methoxyphenoxy)-2-(2-pyrimidinyl)-pyrimidine (which may also be present in the tautomeric form as 5-(o-methoxyphenoxy)-2-(2-pyrimidinyl) -tetrahydropyrimidine4,6-dion).

e) 4,6-dihydroxy-5-(o-methoxyphenoxy)-2-(2-pyrimidinyl)-pyrimidine [or its tautomer 5-(o-methoxyphenoxy)-2-(2-pyrimidinyl)-tetrahydropyrimidine-4,6-dion] was prepared as disclosed in EP 0 526 708 A1 from 2-amidinopyrimidine and dimethyl-(o-methoxyphenoxy)malonate.

Example 5

According to Example 4a), 150 mg p-tert.-butyl-N-[6-(2-aminoethoxy)-5-(o-methoxyphenoxy)-2-(2-pyrimidinyl)-4-pyrimidinyl]benzene-sulfonamide was reacted with 146 mg trifluoromethanesulfonylchloride to give 100 mg of p-tert.-butyl-N-[6-(ethoxy-2-trifluoromethanesulfonamido)-5-(o-methoxyphenoxy)-2-(2-pyrimidinyl)-4-pyrimidinyl] benzene-sulfonamide as a yellow solid. $t_R$=5.97 (LC); M$^+$=683.76 (ES+); M$^+$=681.83 (ES–)

Example 6

According to Example 1a), 263 mg p-tert.-butyl-N-[6-chloro-5-(o-methoxyphenoxy)-2-(2-pyrimidinyl)-4-pyrimidinyl]benzene-sulfonamide was reacted with 592 mg N-(2-hydroxy-ethyl)-p-toluenesulfonamide and 673 mg potassium tert.-butylate in THF to give 30 mg of p-tert.-butyl-N-[6-(ethoxy-2-p-toluenesulfonamido)-5-(o-methoxyphenoxy)-2-(2-pyrimidinyl)-4-pyrimidinyl] benzene-sulfonamide as a white solid. $t_R$=5.67 (LC); M$^+$=705.71 (ES+); M$^+$=703.81 (ES–)

Example 7

According to Example 1a), 526 mg p-tert.-butyl-N-[6-chloro-5-(o-methoxyphenoxy)-2-(2-pyrimidinyl)-4-pyrimidinyl]benzene-sulfonamide was reacted with 1.1 g N-(2-hydroxy-ethyl)-2-thiophenesulfonamide and 660 mg potassium tert.-butylate in THF to give 210 mg of p-tert.-butyl-N-[6-(ethoxy-2-(2-thiophenesulfonamido))-5-(o-methoxyphenoxy)-2-(2-pyrimidinyl)-4-pyrimidinyl] benzene-sulfonamide as a white solid. $t_R$=5.50 (LC); M$^+$=697.64 (ES+); M$^+$=695.69 (ES–)

Example 8

According to Example 4a), 90 mg p-tert.-butyl-N-[6-(2-aminoethoxy)-5-(o-methoxyphenoxy)-2-(2-pyrimidinyl)-4-pyrimidinyl]benzene-sulfonamide was reacted with 63 mg ethanesulfonylchloride to give 60 mg of p-tert.-butyl-N-[6-(ethoxy-2-ethanesulfonamido)-5-(o-methoxyphenoxy)-2-(2-pyrimidinyl)-4-pyrimidinyl]benzene-sulfonamide as a slightly yellow solid. $t_R$=5.14 (LC); M$^+$=641.85 (ES–)

Example 9

According to Example 4a), 70 mg p-tert.-butyl-N-[6-(2-aminoethoxy)-5-(o-methoxyphenoxy)-2-(2-pyrimidinyl)-4-pyrimidinyl]benzene-sulfonamide was reacted with 80 mg p-methoxybenzenesulfonylchloride to give 50 mg of p-tert.-butyl-N-[6-(ethoxy-2-p-methoxybenzenesulfonamido)-5-(o-methoxyphenoxy)-2-(2-pyrimidinyl)-4-pyrimidinyl] benzene-sulfonamide as a white solid. $t_R$=5.57 (LC); M$^+$=719.89 (ES–)

Example 10 a) According to Example 1a), 256 mg 5-i.-propyl-N-[6-chloro-5-(o-methoxyphenoxy)-2-(4-pyridyl)-4-pyrimidinyl]pyridine-2-sulfonamide was reacted with 460 mg N-(2-Hydroxy-ethyl)-2-propanesulfonamide and 673 mg potassium tert.-butylate in THF to give 140 mg of 5-i.-propyl-N-[6-(ethoxy-2-(2-propanesulfonamido))-5-(o-methoxyphenoxy)-2-(4-pyridyl)-4-pyrimidinyl]pyridine-2-sulfonamide as a white solid. 1H-NMR (d6-DMSO): 8.61(d, 2H); 8.59(s, 1H); 8.20(d, 1H); 8.04(d, 1H); 7.75(d, 2H); 7.0(m, 2H); 6.79(m, 2H); 4.39(t, 2H); 3.90(s, 3H); 3.16(m, 2H); 3.03(m, 2H); 1.10(d, 6H); 1.04(d, 6H).

b) 5-i.-propyl-N-[6-chloro-5-(o-methoxyphenoxy)-2-(4-pyrdyl)-4-pyrimidin-yl]pyridine-2-sulfonamide and its precursors are prepared according to procedures disclosed in WO 96/19459.

Example 11

According to Example 1a), 300 mg 5-i.-propyl-N-[6-chloro-5-(o-methoxyphenoxy)-2-(3,4,5-trimethoxyphenyl)-4-pyrimidinyl]pyridine-2-sulfonamide was reacted with 592 mg N-(2-Hydroxy-ethyl)-4-methylbenzenesulfonamide and 673 mg potassium tert.-butylate in THF to give 310 mg of 5-i.-propyl-N-[6-(ethoxy-2-(4-methylbenzenesulfonamido))-5-(o-methoxyphenoxy)-2-(3,4,5-trimethoxyphenyl)-4-pyrimidinyl]pyridine-2-sulfonamide as a white solid. $t_R$=5.33 (LC); M$^+$=780.80 (ES+).

Example 12

According to Example 1a), 256 mg 5-i.-propyl-N-[6-chloro-5-(o-methoxyphenoxy)-2-(4-pyridyl)-4-pyrimidinyl]pyridine-2-sulfonamide was reacted with 592 mg N-(2-hydroxy-ethyl)-4-methylbenzenesulfonamide and 673 mg potassium tert.-butylate in THF to give 220 mg of 5-i.-propyl-N-[6-(ethoxy-2-(4-methylbenzenesulfonamido))-5-(o-methoxyphenoxy)-2-(4-pyridyl)-4-pyrimidinyl]pyridine-2-sulfonamide as a white solid. $t_R$=4.96 (LC); M$^+$=689.77 (ES–); M$^+$=691.68 (ES+).

Example 13

According to Example 1a), 256 mg 5-i.-propyl-N-[6-chloro-5-(o-methoxyphenoxy)-2-(2-pyridyl)-4-pyrimidinyl]pyridine-2-sulfonamide was reacted with 553 mg N-(2-hydroxy-ethyl)benzenesulfonamide and 673 mg potassium tert.-butylate in THF to give 260 mg of 5-i.-propyl-N-[6-(ethoxy-2-benzenesulfonamido)-5-(o-methoxyphenoxy)-2-(4-pyridyl)-4-pyrimidinyl]pyridine-2-sulfonamide as a white solid. $t_R$=4.76 (LC); M$^+$=677.64 (ES+); M$^+$=675.80 (ES–).

Example 14

According to Example 1a), 256 mg 5-i.-propyl-N-[6-chloro-5-(o-methoxyphenoxy)-2-(4-pyridyl)-4-pyrimidinyl]

pyridine-2-sulfonamide was reacted with 383 mg N-(2-hydroxy-ethyl)-methanesulfonamide and 673 mg potassium tert.-butylate in THF to give 110 mg of 5-i.-propyl-N-[6-(ethoxy-2-methanesulfonamido)-5-(o-methoxyphenoxy)-2-(4-pyridyl)-4-pyrimidinyl]pyridine-2-sulfonamide as a white solid. $t_R$=4.13 (LC); M$^+$=613.73 (ES−); M$^+$=615.60 (ES+).

Example 15 a) According to Example 4a), 300 mg 5-i.-propyl-N-[6-(2-aminoethoxy)-5-(o-methoxyphenoxy)-2-(3,4,5-trimethoxyphenyl)-4-pyrimidinyl]pyridine-2-sulfonamide was reacted with 132 mg 2-thiophenesulfonylchloride to give 56 mg 5-i.-propyl-N-[6-(ethoxy-2-thiophenesulfonamido)-5-(o-methoxyphenoxy)-2-(3,4,5-trimethoxyphenyl)-4-pyrimidinyl]pyridine-2-sulfonamide as a white solid. $t_R$=5.55 (LC); M$^+$=772.74 (ES+); M$^+$=770.86 (ES−).

b) 5-i.-propyl-N-[6-(2-aminoethoxy)-5-(o-methoxyphenoxy)-2-(3,4,5-trimethoxyphenyl)-4-pyrimidinyl]pyridine-2-sulfonamide is prepared according to Example 4b).

c) 5-i.-propyl-N-[6-chloro-5-(o-methoxyphenoxy)-2-(3,4,5-trimethoxyphenyl)-4-pyrimidinyl]pyridine-2-sulfonamide is prepared according to procedures disclosed in WO 96/19459 and EP 0 526 708 A1.

Example 16

According to Example 4a), 150 mg 5-i.-propyl-N-[6-(2-aminoethoxy)-5-(o-methoxyphenoxy)-2-(3,4,5-trimethoxyphenyl)-4-pyrimidinyl]pyridine-2-sulfonamide was reacted with 0.08 ml 1-propanesulfonylchloride to give 56 mg 5-i.-propyl-N-[6-(ethoxy-2-(1-propanesulfonamido))-5-(o-methoxyphenoxy)-2-(3,4,5-trimethoxyphenyl)-4-pyrimidinyl]pyridine-2-sulfonamide as a white solid. $t_R$=5.39 (LC); M$^+$=732.74 (ES+); M$^+$=730.82 (ES−).

The precursors are prepared according to Example 15b) and c).

Example 17

According to Example 4a), 100 mg p-tert.-butyl-N-[6-(2-aminoethoxy)-5-(o-methoxyphenoxy)-2-(2-pyrimidinyl)-4-pyrimidinyl]benzene-sulfonamide was reacted with 1-butanesulfonylchloride to give p-tert.-butyl-N-[6-(ethoxy-2-(1-butanesulfonamido))-5-(o-methoxyphenoxy)-2-(2-pyrimidinyl)-4-pyrimidinyl]benzene-sulfonamide as a slightly yellow solid. $t_R$=5.51 (LC); M$^+$=671.81 (ES+); M$^+$=669.90 (ES−).

The precursors are prepared according to example 15b) and c).

Example 18

According to Example 4a), 150 mg 5-i.-propyl-N-[6-(2-aminoethoxy)-5-(o-methoxyphenoxy)-2-(3,4,5-trimethoxyphenyl)-4-pyrimidinyl]pyridine-2-sulfonamide was reacted with 2-propanesulfonylchloride to give 60 mg 5-i.-propyl-N-[6-(ethoxy-2-(2-propanesulfonamido)-5-(o-methoxyphenoxy)-2-(3,4,5-trimethoxyphenyl)-4-pyrimidinyl]pyridine-2-sulfonamide as a white solid. $t_R$=5.41 (LC); M$^+$=732.84 (ES+); M$^+$=730.92 (ES−).

The precursors are prepared according to Example 15b) and c).

Example 19

According to Example 4a), 150 mg 5-i.-propyl-N-[6-(2-aminoethoxy)-5-(o-methoxyphenoxy)-2-(3,4,5-trimethoxyphenyl)-4-pyrimidinyl]pyridine-2-sulfonamide was reacted with 2-thiophenesulfonylchloride to give 65 mg 5-i.-propyl-N-[6-(ethoxy-2-(2-thiophenesulfonamido))-5-(o-methoxyphenoxy)-2-(3,4,5-trimethoxyphenyl)-4-pyrimidinyl]pyridine-2-sulfonamide as a white solid. $t_R$=5.57 (LC); M$^+$=743.68 (ES+); M$^+$=741.75 (ES−).

The precursors are prepared according to Example 15b) and c).

Example 20

According to Example 4a), 100 mg 5-i.-propyl-N-[6-(2-aminoethoxy)-5-(o-methoxyphenoxy)-2-methly-4-pyrimidinyl]pyridine-2-sulfonamide was reacted with ethanesulfonylchloride to give 40 mg 5-i.-propyl-N-[6-(ethoxy-2-ethanesulfonamido)-5-(o-methoxyphenoxy)-2-methyl-4-pyrmidinyl]pyridine-2-sulfonamide as a white solid. $t_R$=5.28 (LC); M$^+$=658.63 (ES+); M$^+$=656.70 (ES−).

The precursors are prepared according to Example 15b) and c).

Example 21

According to Example 4a), 100 mg 5-i.-propyl-N-[6-(2-aminoethoxy)-5-(o-methoxyphenoxy)-2-methly-4-pyrimidinyl]pyridine-2-sulfonamide was reacted with p-toluenesulfonylchloride to give 60 mg 5-i.-propyl-N-[6-(ethoxy-2-p-toluenesulfonamido)-5-(o-methoxyphenoxy)-2-methyl-4-pyrmidinyl]pyridine-2-sulfonamide as a white solid. $t_R$=5.26 (LC); M$^+$=628.73 (ES+); M$^+$=626.74 (ES−).

The precursors are prepared according to Example 15b) and c).

Example 22

According to Example 4a), 100 mg 5-i.-propyl-N-[6-(2-aminoethoxy)-5-(o-methoxyphenoxy)-2-methyl-4-pyrimidinyl]pyridine-2-sulfonamide was reacted with 2-thiophenesulfonylchloride to give 55 mg 5-i.-propyl-N-[6-(ethoxy-2-(2-thiophenesulfonamido))-5-(o-methoxyphenoxy)-2-methyl-4-pyrimidinyl]pyridine-2-sulfonamide as a white solid. $t_R$=5.06 (LC); M$^+$=620.57 (ES+); M$^+$=618.64 (ES−).

The precursors are prepared according to Example 15b) and c).

Example 23

According to Example 4a), 100 mg 5-i.-propyl-N-[6-(2-aminoethoxy)-5-(o-methoxyphenoxy)-2-methly-4-pyrimidinyl]pyridine-2-sulfonamide was reacted with methanesulfonylchloride to give 45 mg 5-i.-propyl-N-[6-(ethoxy-2-methanesulfonamido)-5-(o-methoxyphenoxy)-2-methyl-4-pyrimidinyl]pyridine-2-sulfonamide as a white solid. $t_R$=4.47 (LC); M$^+$=552.56 (ES+); M$^+$=550.66 (ES−).

Example 24 a) At 0° C. a solution of 14.2 g of diethyl 2-(p-tolyl)-malonate in 50 ml of methanol was slowly added to a solution of 9.4 g of sodium methylate in 300 ml of methanol. Upon completion of the addition the reaction mixture was allowed to warm up and 5.4 g of formamidine hydrochloride was added. The mixture was stirred at room temperature for 16 h. The solvent was removed under reduced pressure and the remaining residue was treated with 150 ml of 2 N hydrochloric acid. The suspension was stirred for 0.5 h. At 0–5° C., the pH was carefully adjusted to 4 using 10 N sodium hydroxide solution. The precipitate was collected, washed with cold water, isopropanol, and diethyl ether and dried under high vacuum at 65° C. to give 11.2 g of 4,6-dihydroxy-5-(p-tolyl)-pyrimidine (or a tautomer) as a white powder.

b) At room temperature 10 ml of N,N-dimethylaniline was added to a mixture of 5.1 g of 4,6-dihydroxy-5-(p-tolyl)-pyrimidine and 75 ml of POCl$_3$. The reaction mixture was stirred at 70° C. for 16 h. The excess of POCl$_3$ was distilled off and the remaining oil was treated with an ice/water mixture and extracted three times with diethyl ether. The combined organic layers was washed with 1N aqueous hydrochloric acid followed by brine, dried over MgSO$_4$ and evaporated. The remaining brown oil was crystallised from isopropanol. The pale yellow crystals was collected, washed with cold isopropanol and dried under high vacuum to furnish 4.1 g of 4,6-dichloro-5-(p-tolyl)-pyrimidine.

c) A mixture of 0.8 g of 4,6-dichloro-5-(p-tolyl)-pyrimidine and 1.68 g of 4-tert.-butylbenzene sulfonamide potassium salt in 20 ml of DMSO was stirred at room temperature for 24 h. The mixture was poured onto 200 ml of water and extracted twice with 100 ml of diethyl ether. The organic layers was extracted twice with 50 ml of water. The combined aqueous layers was acidified with conc. hydrochloric acid. The resulting fine suspension was extracted twice with ethyl acetate. The combined organic layers was dried over Na$_2$SO$_4$ and evaporated. The residue was dried under high vacuum to give 1.34 g 4-tert.-butyl-N-[6-chloro-5-(p-tolyl)-4-pyrimidinyl]-benzene sulfonamide as a white powder. LC-MS: $t_R$=5.92 min, [M+1]$^+$= 416.20, [M−1]$^−$=414.24.

d) 100 mg 4-tert.-butyl-N-[6-chloro-5-(p-tolyl)-4-pyrimidinyl]-benzene sulfonamide was dissolved in 5 ml dry THF. 162 mg of potassium-tert.-butylate and 200 mg of N-(2-hydroxyethyl)-N-methyl-ethanesulfonamide was added and the mixture was heated to reflux for 8 h then cooled to room temperature. Ethyl acetate was added and the precipitated side product was filtered off. The filtrate was concentrated in vacuo. The crude product was purified by column chromatography (silica gel; ethyl acetate) to give 45 mg of 4-tert.-butyl-N-{6-[2-(ethanesulfonyl-methyl-amino)-ethoxy]-5-p-tolyl-pyrimidin-4-yl}-benzenesulfonamide. LC-MS: $t_R$=5.58 min, [M−1]$^−$= 545.54.

Example 25

According to Example 24d) 100 mg 4-tert.-butyl-N-[6-chloro-5-(p-tolyl)-4-pyrimidinyl]-benzene sulfonamide was reacted with N-(2-hydroxyethyl)-N-methyl-toluenesulfonamide to give 14 mg 4-tert.-butyl-N-{6-[2-(toluene-sulfonyl-methyl-amino)-ethoxy]-5-p-tolyl-pyrimidin-4-yl}-benzenesulfonamide. LC-MS: $t_R$=6.18 min, [M−1]$^−$=607.54.

Example 26 a) According to Example 4b), 500 mg 4-tert.-butyl-N-[6-chloro-5-(p-tolyl)-4-pyrimidinyl]-benzene sulfonamide was reacted with 2-amino-ethanol to give 450 mg N-[6-(2-amino-ethoxy)-5-p-tolyl-pyrimidin-4-yl]4-tert.-butyl-benzenesulfonamide. LC-MS: $t_R$=3.90 min, [M−1]$^−$= 439.44.

b) According to Example 4a) with DBU instead of Hünig's base, 200 mg N-[6-(2-amino-ethoxy)-5-p-tolyl-pyrimidin-4-yl]-4-tert.-butyl-benzenesulfonamide was reacted with tosylchloride to give 147 mg 4-tert.-butyl-N-{6-[2-(toluenesulfonyl-amino)-ethoxy]-5-p-tolyl-pyrimidin-4-yl}-benzenesulfonamide. LC-MS: $t_R$=5.85 min, [M−1]$^−$=593.50.

Example 27 a) At 5° C. 12.7 g of sodium methylate was added portionwise to a solution of 18.9 g of dimethyl-2-(o-methoxyphenoxy)malonate in 450 ml of methanol. Upon completion of the addition stirring was continued at room temperature for 30 min followed by the addition of 6 g of formamidine hydrochloride. The mixture was stirred at room temperature for 72 h. Eventually, the solvent was removed under reduced pressure and the remaining residue was suspended in diethyl ether. The solid material was filtered off and dissolved in 100 ml of water. The solution was acidified with conc. hydrochloric acid. A white precipitate formed. The precipitate was collected, washed with water and dried to give 15.1 g of 5-(o-methoxyphenoxy)-4,6-dihydroxy-pyrimidine (or a tautomer) as a white powder.

b) To a solution of 7.5 g of 5-(o-methoxyphenoxy)-4,6-dihydroxy-pyrimidine in 90 ml of POCl$_3$ 24 ml of N,N-dimethylaniline was added. The mixture was heated to 160° C. and stirred for 2.5 h. Excess of POCl$_3$ was distilled off under reduced pressure. Traces of POCl$_3$ was coevaporated with toluene. The remaining oil was treated with a water:ice mixture. The mixture was acidified with 1 N hydrochloric acid and extracted twice with diethyl ether. The combined organic layers was washed twice with dilute aqueous hydrochloric acid, dried over MgSO$_4$ and evaporated. The remaining solid was washed with methanol and dried. This gave 4.75 g of 4,6-dichloro-5-(o-methoxyphenoxy)-pyrimidine as a pale yellow powder.

c) To a solution of 2 g of 4,6-dichloro-5-(o-methoxyphenoxy)-pyrimidine in 40 ml of DMSO 3.7 g of 4-tert.-butylbenzene sulfonamide potassium salt was added. The resulting solution was stirred for 20 h at room temperature. Eventually, the mixture was poured onto 400 ml of water and washed twice with 200 ml of diethyl ether. The organic layers was extracted with 200 ml of water. The combinded aqueous layers was acidified with conc. hydrochloric acid. The mixture was cooled to 0° C. and 100 ml of brine was added. The precipitate that formed was collected and dried to yield 2.7 g of 4-tert.-butyl-N-[6-chloro-5-(o-methoxyphenoxy)-4-pyrimidinyl]-benzene sulfonamide as a white powder. LC-MS: $t_R$=5.80 min, [M+1]$^+$=448.17, [M−1]$^−$=446.21.

d) According to Example 4b) 1.13 g 4-tert.-butyl-N-[6-chloro-5-(o-methoxy-phenoxy)-4-pyrimidinyl]-benzene sulfonamide was reacted with 2-amino-ethanol to give 1.08 g 4-tert.-butyl-N-[6-(2-aminoethoxy)-5-(o-methoxy-phenoxy)-4-pyrimidinyl]-benzene sulfonamide. LC-MS: $t_R$=3.81 min, [M−1]$^−$=471.41 e) According to Example 4a) 100 mg 4-tert.-butyl-N-[6-(2-aminoethoxy)-5-(o-methoxy-phenoxy)-4-pyrimidinyl]-benzene sulfonamide was reacted with 166 mg 4-bromobenzenesulfonylchloride to give 106 mg 4-tert.-butyl-N-{6-[2-(4-bromobenzenesulfonyl-amino)-ethoxy]-5-(o-methoxy-phenoxy)-pyrimidin-4-yl}-benzenesulfonamide. LC-MS: $t_R$=5.95 min, [M−1]$^−$= 691.41.

Example 28

According to Example 4a) 100 mg 4-tert.-butyl-N-[6-(2-aminoethoxy)-5-(o-methoxy-phenoxy)-4-pyrimidinyl]-benzene sulfonamide was reacted with 123 mg 4-methylbenzenesulfonylchloride to give 125 mg 4-tert.-butyl-N-{6-[2-(4-methylbenzenesulfonyl-amino)-ethoxy]-

5-(o-methoxy-phenoxy)-pydmidin-4-yl}-benzenesulfonamide. LC-MS: $t_R$=5.80 min, [M−1]⁻=625.52.

Example 29

According to Example 4a) 100 mg 4-tert.-butyl-N-[6-(2-aminoethoxy)-5-(o-methoxy-phenoxy)-4-pyrimidinyl]-benzene sulfonamide was reacted with 121 mg thiophen-2-sulfonylchloride to give 73 mg 4-tert.-butyl-N-{6-[2-(2-thiophenesulfonyl-amino)-ethoxy]-5-(o-methoxy-phenoxy)-pydmidin-4-yl}-benzenesulfonamide. LC-MS: $t_R$=5.61 min, [M−1]⁻=617.42.

Example 30

According to Example 4a) 100 mg 4-tert.-butyl-N-[6-(2-aminoethoxy)-5-(o-methoxy-phenoxy)-4-pyrimidinyl]-benzene sulfonamide was reacted with 93 mg 1-propanesulfonylchloride to give 110 mg 4-tert.-butyl-N-{6-[2-(1-propanesulfonyl-amino)-ethoxy]-5-(o-methoxy-phenoxy)-pyrimidin-4-yl}-benzenesulfonamide. LC-MS: $t_R$=5.43 min, [M−1]⁻=577.49.

Example 31

According to Example 4a) 100 mg 4-tert.-butyl-N-[6-(2-aminoethoxy)-5-(o-methoxy-phenoxy)-4-pyrimidinyl]-benzene sulfonamide was reacted with 84 mg ethanesulfonylchloride to give 98 mg 4-tert.-butyl-N-{6-[2-(ethanesulfonylamino)-ethoxy]-5-(o-methoxy-phenoxy)-pydmidin-4-yl}-benzenesulfonamide. LC-MS: $t_R$=5.25 min, [M−1]⁻=563.46.

Example 32

According to Example 4a) 100 mg 4-tert.-butyl-N-[6-(2-aminoethoxy)-5-(o-methoxy-phenoxy)-4-pyrimidinyl]-benzene sulfonamide was reacted with 74 mg methanesulfonylchloride to give 24 mg 4-tert.-butyl-N-{6-[2-(methanesulfonyl-amino)-ethoxy]-5-(o-methoxy-phenoxy)-pyrimidin-4-yl}-benzenesulfonamide. LC-MS: $t_R$=5.11 min, [M−1]⁻=549.45.

Example 33 a) 2.77 g 4,6-dichloro-2-methylthio-5-phenylpyrimidine was dissolved in 50 ml DMSO and 3.42 g 4-tert-butylbenzenesulfonamide potassium salt and 1 ml Hünig's base was added. Stirring was continued for 24 h. The mixture was poured onto 400 ml water, washed with diethylether and acidified with conc. hydrochloric acid. The product precipitated and was filtered off and dried in vacuo to give 4 g of 4-tert.-butyl-N-(6-chloro-2-methylsulfanyl-5-phenyl-pyrimidin-4-yl)-benzenesulfonamide. LC-MS: $t_R$=6.29 min, [M+1]⁺=448.17; 459.17.

b) 4.0 g 4-tert.-butyl-N-(6-chloro-2-methylsulfanyl-5-phenyl-pyrimidin-4-yl) -benzenesulfonamide was reacted with 2-aminoethanol according to Example 4b) to give 1.65 g 4-tert.-butyl-N-[6-(2-aminoethoxy)-2-methylsulfanyl-5-phenyl-pyrimidin-4-yl]-benzenesulfonamide. LC-MS: $t_R$=3.75 min, [M−1]⁻=471.38.

c) According to Example 4a) 100 mg 4-tert.-butyl-N-[6-(2-aminoethoxy)-2-methylsulfanyl-5-phenyl-pyrimidin-4-yl]-benzenesulfonamide was reacted with 123 mg toluene-4-sulfonylchloride to give 120 mg 4-tert.-butyl-N-[6-(2-(p-methylphenylsulfonyl)-amino)-ethoxy)-2-methylsulfanyl-5-phenyl-pyrimidin-4-yl]-benzenesulfonamide. LC-MS: $t_R$=6.16 min. [M−1]⁻=625.49.

Example 34

According to Example 4a) 100 mg 4-tert.-butyl-N-[6-(2-aminoethoxy)-2-methylsulfanyl-5-phenyl-pyrimidin-4-yl]-benzenesulfonamide was reacted with 121 mg thiophene-2-sulfonylchloride to give 115 mg 4-tert.-butyl-N-[6-(2-(2-thiophenesulfonyl)-amino)-ethoxy)-2-methylsulfanyl-5-phenyl-pydmidin-4-yl]-benzenesulfonamide. LC-MS: $t_R$=5.98 min, [M−1]⁻=617.39.

Example 35

According to Example 4a) 100 mg 4-tert.-butyl-N-[6-(2-aminoethoxy)-2-methylsulfanyl-5-phenyl-pyrimidin-4-yl]-benzenesulfonamide was reacted with 83 mg ethanesulfonylchloride to give 56 mg 4-tert.-butyl-N-[6-(2-(ethanesulfonyl)-amino)-ethoxy)-2-methylsulfanyl-5-phenyl-pyrimidin-4-yl]-benzenesulfonamide. LC-MS: $t_R$=5.68 min. [M−1]⁻=563.42.

Example 36 a) 12.15 g sodium methylate was dissolved in 200 ml methanol and 21.1 g dimethyl-(o-methoxyphenoxy)malonate was added. Stirring was continued for 130 min. The mixture was cooled to 10° C. and 7.6 g thiourea was added. Stirring was continued for 24 h. The solvent was evaporated in vacuo. The residue was stirred with diethyl ether. The ether layer was filtered off and the solid was dissolved in 60 ml water and acidified to pH=4 with conc. acetic acid. The precipitated product was filtered and washed with methanol and dried at 30° C. and reduced pressure to give 19.8 g 5-(o-methoxyphenoxy)-2-thioxo-dihydro-pyrimidine-4,6-dione (or a tautomere thereof.

b) 19.8 g 5-(o-methoxyphenoxy)-2-thioxo-dihydro-pyrimidine-4,6-dione was dissolved in 100 ml DMSO and 10.28 g potassium carbonate was added. After 30 min 4.36 ml methyl iodide was added in portions within 10 min. Stirring was continued for 4 h followed by the addition of 250 ml water. The solution was acidified with 25% hydrochloric acid. The precipitated product was filtered off, washed with diethylether and dried in vacuo to give 12.9 g 5-(o-methoxyphenoxy)-2-methylsulfanyl-pyrimidine-4,6-diol. LC-MS: $t_R$=3.01 min, [M−1]⁻=279.15.

c) 10 g 5-(o-methoxyphenoxy)-2-methylsulfanyl-pyrimidine-4,6-diol was dissolved in 50 ml phosphorous oxychloride and 16.7 ml N,N-dimethylaniline and heated to reflux for 3.5 h. Then toluene was added and the reaction mixture was evaporated. Then ice/water was slowly added followed by the addition of conc. hydrochloric acid. This mixture was extracted with ethylacetate and diethylether followed by filtration through activated charcoal and evaporation of the solvent. The residue was crystallized from diethylether/n-hexane to give 6.34 g 5-(o-methoxyphenoxy)-2-methylsulfanyl-4,6-dichloro-pyrimidine.

d) 5 g 5-(o-methoxyphenoxy)-2-methylsulfanyl-4,6-dichloro-pyrimidine was dissolved in 50 ml DMSO and 8.8 g tert.-butylphenylsulfonamide potassium salt was added and stirring was continued for 24 h. The mixture was poured onto 400 ml water and acidified with conc. hydrochloric acid. The precipitated product was filtered off and washed with an additional portion of water. After drying at reduced pressure 4.64 g 4-tert.-butyl-N-[6-chloro-5-(o-methoxyphenoxy)-2-methylsulfanyl-pyrimidin-4-yl]-benzenesulfonamide was obtained. LC-MS: $t_R$=6.22 min, [M−1]⁻=492.26.

e) According to the procedure described in Example 4b) 4.2 g 4-tert.-butyl-N-[6-chloro-5-(o-methoxyphenoxy)-2-methylsulfanyl-pyrimidin-4-yl]-benzenesulfonamide was transformed to 4.4 g 4-tert.-butyl-N-[6-(2-aminoethoxy)-5-(o-methoxyphenoxy)-2-methylsulfanyl-pyrimidin-4-yl]-benzenesulfonamide. LC-MS: $t_R$=4.14 min, [M−1]⁻=517.34.

f) According to the procedure described in Example 4a) 2 g of 4-tert.-butyl-N-[6-(2-aminoethoxy)-5-(o-methoxyphenoxy)-2-methylsulfanyl-pyrimidin-4-yl]-benzenesulfonamide was reacted with 0.81 g ethanesulfonylchloride to give 0.7 g 4-tert.-butyl-N-[6-(2-ethanesulfonylamino-ethoxy)-5-(o-methoxyphenoxy)-2-methylsulfanyl-pyrimidin-4-yl]-benzenesulfonamide. LC-MS: $t_R$=5.85 min, [M+1]$^+$=611.31.

g) 305 mg 4-tert.-butyl-N-[6-(2-ethanesulfonylamino-ethoxy)-5-(o-methoxyphenoxy)-2-methylsulfanyl-pyrimidin-4-yl]-benzenesulfonamide was dissolved in 2 ml dichloromethane at 0° C. followed by the addition of 271 mg m-chloroperbenzoic acid dissolved in 3 ml dichloromethane. Stirring was continued for 1 hour at 0° C. and 2 h at room temperature. Then sodium bisulfite solution was added and the organic layer was separated and washed with water, dried, concentrated and chromatographed over silicagel with ethyl acetate/n-hexane to give 250 mg 4-tert.-butyl-N-[6-(2-ethanesulfonylamino-ethoxy)-2-methanesulfonyl-5-(o-methoxyphenoxy-pyrimidin-4-yl]-benzenesulfonamide. LC-MS: $t_R$=5.17 min, [M+1]$^+$=643.32.

Example 37

According to Example 36f) 2 g of 4-tert.-butyl-N-[6-(2-aminoethoxy)-5-(o-methoxyphenoxy)-2-methylsulfanyl-pyrimidin-4-yl]-benzenesulfonamide was reacted with 1.19 g p-toluenesulfonylchloride to give 0.9 g 4-tert.-butyl-N-[6-(2-p-toluenesulfonylamino-ethoxy)-5-(o-methoxyphenoxy)-2-methylsulfanyl-pyrimidin-4-yl]-benzenesulfonamide. LC-MS: $t_R$=6.24 min, [M+1]$^+$=673.34.

Example 38 a) According to the procedure described in Example 1g) 3.3 g 4,6-dichloro-2-cyclopropyl-5-(o-methoxyphenoxy)-pyrimidine (prepared according to procedures described in Example 1) was reacted with 5-i-propyl-2-pyridyl-sulfonamide potassium salt to give 4.04 g 5-i-propyl-N-[6-chloro-5-(o-methoxyphenoxy)-2-cyclopropyl-pyrimidin-4-yl]-pyridine-2-sulfonamide. LC-MS: $t_R$=5.64 min, [M−1]$^-$=473.29.

b) According to the procedure described in Example 4b) 5-i-propyl-N-[6-chloro-5-(o-methoxyphenoxy)-2-cyclopropyl-pyrimidin-4-yl]-pyridine-2-sulfonamide was reacted with 2-aminoethanol to give 950 mg 5-i-propyl-N-[6-(2-aminoethoxy)-5-(o-methoxyphenoxy)-2-cyclopropyl-pyrimidin-4-yl]-pyridine-2-sulfonamide. LC-MS: $t_R$=3.66 min, [M−1]$^-$=498.37.

c) According to the procedure described in Example 4a), 250 mg 5-i-propyl-N-[6-(2-aminoethoxy)-5-(o-methoxyphenoxy)-2-cyclopropyl-pyrimidin-4-yl]-pyridine-2-sulfonamide was reacted with 4-methylbenzenesulfonylchloride to give 100 mg 5-i-propyl-N-[6-(2-ethanesulfonylamino-ethoxy)-5-(o-methoxyphenoxy)-2-cyclopropyl-pyrimidin-4-yl]-pyridine-2-sulfonamide. LC-MS: $t_R$=5.32 min, [M−1]$^-$=604.39.

Example 39

According to the procedure described in Example 4a), 250 mg 5-i-propyl-N-[6-(2-aminoethoxy)-5-(o-methoxyphenoxy)-2-cyclopropyl-pyrimidin-4-yl]-pyridine-2-sulfonamide was reacted with 4-methylbenzenesulfonylchloride to give 140 mg 5-i-propyl-N-[6-(2-(4-methylbenzene)-sulfonylamino-ethoxy)-5-(o-methoxyphenoxy)-2-cyclopropyl-pyrimidin-4-yl]-pyridine-2-sulfonamide. LC-MS: $t_R$=5.69 min. [M−1]$^-$=652.39.

Example 40 a) According to the procedure described in Example 1g) 3.3 g 4,6-dichloro-2-cyclopropyl-5-(o-methoxyphenoxy)-pyrimidine (prepared according to procedures described in Example 1) was reacted with 4-tert.-butylphenylsulfonamide potassium salt to give 4.22 g 4-tert.-butyl-N-[6-chloro-5-(o-methoxyphenoxy)-2-cyclopropyl-pyrimidin-4-yl]-benzene-sulfonamide. LC-MS: $t_R$=6.24 min, [M+1]$^+$=488.23.

b) According to the procedure described in Example 4b) 4-tert.-butyl-N-[6-chloro-5-(o-methoxyphenoxy)-2-cyclopropyl-pyrimidin-4-yl]-benzene-sulfonamide was reacted with 2-aminoethanol to give 1.28 g 4-tert.-butyl-N-[6-(2-aminoethoxy)-5-(o-methoxyphenoxy)-2-cyclopropyl-pyrimidin-4-yl]-benzene-sulfonamide. LC-MS: $t_R$=4.04 min, [M−1]$^-$=511.50.

c) According to the procedure described in Example 4a), 256 mg 4-tert.-butyl-N-[6-(2-aminoethoxy)-5-(o-methoxyphenoxy)-2-cyclopropyl-pyrimidin-4-yl]-benzene-sulfonamide was reacted with 2-propanesulfonylchloride to give 150 mg 4-tert.-butyl-N-[6-(2-(2-propane)-sulfonylamino-ethoxy)-5-(o-methoxyphenoxy)-2-cyclopropyl-pyrimidin-4-yl]-benzene-sulfonamide. LC-MS: $t_R$=5.88 min, [M−1]$^-$=617.36.

Example 41

According to the procedure described in Example 4a), 256 mg 4-tert.-butyl-N-[6-(2-aminoethoxy)-5-(o-methoxyphenoxy)-2-cyclopropyl-pyrimidin-4-yl]-benzene-sulfonamide was reacted with 4-methylbenzene-sulfonylchloride to give 160 mg 4-tert.-butyl-N-[6-(4-methylbenzene)-sulfonylamino-ethoxy)-5-(o-methoxyphenoxy)-2-cyclopropyl-pyrimidin-4-yl]-benzene-sulfonamide. LC-MS: $t_R$=6.25 min, [M−1]$^-$=665.37.

Example 42 a) A solution of 32.75 g of dimethyl-(o-methoxyphenoxy) malonate in 250 ml of methanol was cooled to 0° C. 20.0 g sodium methylate was added portionwise and upon completion of the addition the mixture was stirred at room temperature for 6 h. Then 25.0 g of morpholinoformamidine hydrobromide was added and stirring was continued for 72 h. The solvent of the beige suspension was evaporated and the residue was washed twice with 150 ml of diethyl ether. The remaining powder was dissolved in 200 ml of water. Upon adjusting the pH to 4 with 50 ml of acetic acid a precipitate formed. The precipitate was collected, washed with water and dried under high vacuum to yield 17.01 g of 5-(o-methoxyphenoxy)-4,6-dihydroxy-2-(N-morpholino)-pyrimidine (or a tautomer) as a slightly beige powder.

b) At 0° C. 50 ml of POCl$_3$ was carefully added to 27.5 ml of Hünig's base. To this mixture 17 g of 5-(o-methoxyphenoxy)-4,6-dihydroxy-2-(N-morpholino)-pyrimidine was added portionwise. The resulting mixture was stirred over night at 130° C. The excess of reagents was evaporated and traces of POCl$_3$ was removed by coevaporation with toluene. The black residue was treated with 50 ml of DCM and 50 ml of a water/ice mixture. After stirring for 15 min, the mixture was diluted with 400 ml of water and 400 ml of DCM. The organic layer was separated and washed with 300 ml of water. The aqueous layer was extracted with 400 ml of DCM. The combined DCM layers was dried over Na$_2$SO$_4$ and the solvent was removed to a volume of about 100 ml. The remaining solution was filtered over 50 g of silica gel eluting with DCM. The filtrate was evaporated. The resulting residue was suspended in 50 ml of diethyl ether. The solid was filtered off and dried to give 13.85 g of 4,6-dichloro-5-(o-methoxyphenoxy)-2-(N-morpholino)-pyrimidine as a white crystalline powder.

c) To a suspension of 4 g of 4,6-dichloro-5-(o-methoxyphenoxy)-2-(N-morpholino)-pyrimidine in 60 ml of DMSO was added 5.32 g of 5-isopropyl-2-pyridine sulfonamide potassium salt and 0.98 ml of Hünig's base. The mixture was stirred at 65° C. for 72 h. The dark solution was poured onto 500 ml of water and quickly filtered through celite. The filtrate was extracted with 500 ml and 250 ml of diethyl ether. The organic layers were extracted with 100 ml of water. The aqueous layers were combined, acidified with 3.5 ml of acetic acid and cooled to 0° C. The precipitate that formed was collected, washed with cold water and dried under high vacuum to furnish 4.94 g of 5-isopropyl-N-[6-chloro-5-(o-methoxyphenoxy)-2-(N-morpholino)-4-pyrimidinyl]-2-pyridine sulfonamide as a brownish powder. LC-MS: $t_R$=5.46 min, $[M+1]^+$=520.22, $[M-1]^-$=518.36.

d) According to the procedure described in Example 4b) 2 g 5-isopropyl-N-[6-chloro-5-(o-methoxyphenoxy)-2-(N-morpholino)-4-pyrimidinyl]-2-pyridine sulfonamide was reacted with 2-aminoethanol to give 750 mg 5-isopropyl-N-[6-(2-aminoethoxy)-5-(o-methoxyphenoxy)-2-(N-morpholino)-4-pyrimidinyl]-2-pyridine sulfonamide. LC-MS: $t_R$=3.45 min, $[M+1]^+$=545.58, $[M-1]^-$=543.68.

e) According to the procedure described in Example 4a) 70 mg 5-isopropyl-N-[6-(2-aminoethoxy)-5-(o-methoxyphenoxy)-2-(N-morpholino)-4-pyrimidinyl]-2-pyridine sulfonamide was reacted with thiophen-2-sulfonylchloride to give 42 mg 5-isopropyl-N-[6-(2-(2-thiophensulfonyl)-amino-ethoxy)-5-(o-methoxyphenoxy)-2-(N-morpholino)-4-pyrimidinyl]-2-pyridine sulfonamide. LC-MS: $t_R$=5.28 min, $[M+1]^+$=691.28.

Example 43

According to Example 39) 250 mg 5-i-propyl-N-[6-(2-aminoethoxy)-5-(o-methoxyphenoxy)-2-cyclopropyl-pyrimidin-4-yl]-pyridine-2-sulfonamide was reacted with ethanesulfonylchloride to give 212 mg 5-i-propyl-N-[6-(2-ethanesulfonylamino-ethoxy)-5-(o-methoxyphenoxy)-2-cyclopropyl-pyrimidin-4-yl]-pyridine-2-sulfonamide. LC-MS: $t_R$=5.18 min, $[M-1]^-$=589.93.

Example 44

According to Example 40) 256 mg 4-tert.-butyl-N-[6-(2-aminoethoxy)-5-(o-methoxyphenoxy)-2-cyclopropyl-pyrimidin-4-yl]-benzene-sulfonamide was reacted with ethanesulfonylchloride to give 120 mg 4-tert.-butyl-N-[6-(2-ethanesulfonylamino-ethoxy)-5-(o-methoxyphenoxy)-2-cyclopropyl-pyrimidin-4-yl]-benzene-sulfonamide. LC-MS: $t_R$=5.79 min. $[M-1]^-$=603.90.

Example 45

According to the procedure described in Example 4a) 70 mg 5-isopropyl-N-[6-(2-aminoethoxy)-5-(o-methoxyphenoxy)-2-(N-morpholino)-4-pyrimidinyl]-2-pyridine sulfonamide was reacted with methanesulfonylchloride to give 50 mg 5-isopropyl-N-[6-(2-methanesulfonylamino-ethoxy)-5-(o-methoxyphenoxy)-2-(N-morpholino)-4-pyrimidinyl]-2-pyridine sulfonamide. LC-MS: $t_R$=4.80 min, $[M+1]^+$=623.37.

Example 46

According to the procedure described in Example 4a) 70 mg 5-isopropyl-N-[6-(2-aminoethoxy)-5-(o-methoxyphenoxy)-2-(N-morpholino)-4-pyrimidinyl]-2-pyridine sulfonamide was reacted with 1-propanesulfonylchloride to give 56 mg 5-isopropyl-N-[6-(2-(1-propane)sulfonylamino-ethoxy)-5-(o-methoxyphenoxy)-2-(N-morpholino)-4-pyrimidinyl]-2-pyridine sulfonamide. LC-MS: $t_R$=5.11 min, $[M+1]^+$=651.32.

Example 47 a) According to the procedure described in Example 4b) 1.04 g 5-i.-propyl-N-[6-chloro-5-(o-methoxyphenoxy)-2-(4-pyridyl)-4-pyrimidinyl]pyridine-2-sulfonamide was reacted with 3-aminopropanol to give 850 mg 5i.-propyl-N-[6-(3-aminopropoxy)-5-(o-methoxyphenoxy)-2-(4-pyridyl)4-pyrimidinyl]pyridine-2-sulfonamide. LC-MS: $t_R$=3.25 min, $[M+1]^+$=551.33.

b) According to the procedure described in Example 4a) 200 mg 5-i.-propyl-N-[6-(3-aminopropoxy)-5-(o-methoxyphenoxy)-2-(4-pyridyl)-4-pyrimidinyl]-pyridine-2-sulfonamide was reacted with methanesulfonylchloride to give 130 mg 5-i.-propyl-N-[6-(3-methanesulfonylamino-propoxy)-5-(o-methoxyphenoxy)-2-(4-pyridyl)-4-pyrimidinyl]-pyridine-2-sulfonamide. LC-MS: $t_R$=4.22 min, $[M+1]^+$=629.25.

Example 48

According to the procedure described in Example 4a) 200 mg 5-i.-propyl-N-[6-(3-aminopropoxy)-5-(o-methoxyphenoxy)-2-(4-pyridyl)-4-pyrimidinyl]-pyridine-2-sulfonamide was reacted with 1-propanesulfonylchloride to give 120 mg 5-i.-propyl-N-[6-(3-(1-propane)sulfonylamino-propoxy)-5-(o-methoxyphenoxy)-2-(4-pyridyl)-4-pyrimidinyl]-pyridine-2-sulfonamide. LC-MS: $t_R$=4.55 min, $[M+1]^+$=657.35.

Example 49 a) To a stirred solution of 22.9 g sodium methylate in 250 ml methanol was added 37.5 g dimethyl-2-(o-methoxyphenoxy)malonate in portions within 15 min. Stirring was continued for 30 min. Then 15.8 g trifluoroacetamidine was added followed by stirring for 20 h at room temperature. Work up was done according to the procedure described in Example 1d) to give 29.77 g 5-(o-methoxyphenoxy)-2-trifluoromethyl-pyrimidine-4,6-dione (or its tautomeric form). LC-MS: $t_R$=3.41 min, $[M+1]^+$=303.32.

b) According to the procedure described in Example 1e) 29.77 g 5-(o-methoxyphenoxy)-2-trifluoromethyl-pyrimidine-4,6-dione (or its tautomeric form) was transformed to 23.95 g 5-(o-methoxyphenoxy)-4,6-dichloro-2-trifluoromethyl-pyrimidine. LC-MS: $t_R$=5.48 min.

c) According to the procedure described in Example 1g) 4.0 g 5-(o-methoxyphenoxy)-4,6-dichloro-2-trifluoromethyl-pyrimidine was reacted with 5-i-propyl-pyridine-2-sulfonamide potassium salt in DMSO to give 4.03 g 5-i.-propyl-N-[6-chloro-5-(o-methoxyphenoxy)-2-trifluoromethyl4-pyrimidinyl]pyridine-2-sulfonamide. LC-MS: $t_R$=5.24 min, $[M+1]^+$=503.44.

d) According to the procedure described in Example 4b) 2.0 g 5-i.-propyl-N-[6-chloro-5-(o-methoxyphenoxy)-2-trifluoromethyl-4-pyrimidinyl]pyridine-2-sulfonamide was reacted with 2-aminoethanol to give 1.14 g 5-i.-propyl-N-[6-(2-aminoethoxy)-5-(o-methoxyphenoxy)-2-trifluoromethyl-4-pyrimidinyl]pyridine-2-sulfonamide. LC-MS: $t_R$=4.87 min, $[M+1]^+$=528.41.

e) According to the procedure described in Example 4a) 100 mg 5-i.-propyl-N-[6-(2-aminoethoxy)-5-(o-methoxyphenoxy)-2-trifluoromethyl-4-pyrimidinyl]pyridine-2-sulfonamide was reacted with 1-butanesulfonylchloride to give 110 mg 5-i.-propyl-N-[6-(2-butanesulfonylamino-ethoxy)-5-(o-methoxyphenoxy)-2-trifluoromethyl-4-pyrimidinyl]pyridine-2-sulfonamide. LC-MS: $t_R$=5.41 min, $[M+1]^+$=648.49.

Example 50

According to the procedure described in Example 4a) 100 mg 5-i.-propyl-N-[6-(2-aminoethoxy)-5-(o-methoxyphenoxy)-2-trifluoromethyl-4-pyrimidinyl]pyridine-2-sulfonamide was reacted with 1-propanesulfonylchloride to give 110 mg 5-i.-propyl-N-[6-(2-(1-propane)sulfonylamino-ethoxy)-5-(o-methoxyphenoxy)-2-trifluoromethyl-4-pyrimidinyl]pyridine-2-sulfonamide. LC-MS: $t_R$=5.21 min, $[M+1]^+$=634.47.

Example 51

According to the procedure described in Example 4a) 20 mg 4-tert.-butyl-N-[6-(2-aminoethoxy)-5-(o-methoxyphenoxy)-2-(4-pyridyl)-4-pyrimidinyl]-benzene-sulfonamide was reacted with thiophene-2-sulfonylchloride to give 20 mg 4-tert.-butyl-N-[6-(2-(thiophene-2-sulfonylamino)-ethoxy)-5-(o-methoxyphenoxy)-2-(4-pyridyl)-4-pyrimidinyl]-benzene-sulfonamide. LC-MS: $t_R$=5.17 min, $[M+1]^+$=696.57.

Example 52 a) A solution of 32.75 g of dimethyl-(o-methoxyphenoxy) malonate in 250 ml of methanol was cooled to 0° C. 20.0 g sodium methylate was added portionwise and upon completion of the addition the mixture was stirred at room temperature for 6 h. Then 25.0 g of morpholinoformamidine hydrobromide was added and stirring was continued for 72 h. The solvent of the beige suspension was evaporated and the residue was washed twice with 150 ml of diethyl ether. The remaining powder was dissolved in 200 ml of water. Upon adjusting the pH to 4 with 50 ml of acetic acid a precipitate formed. The precipitate was collected, washed with water, and dried under high vacuum to yield 17.01 g of 5-(o-methoxyphenoxy)-4,6-dihydroxy-2-(N-morpholino)-pyrimidine (or a tautomer) as a slightly beige powder.

b) At 0° C. 50 ml of $POCl_3$ was carefully added to 27.5 ml of Hünig's base. To this mixture 17 g of 5-(o-methoxyphenoxy)-4,6-dihydroxy-2-(N-morpholino)-pyrimidine was added portionwise. The resulting mixture was stirred over night at 130° C. The excess of reagents was evaporated and traces of $POCl_3$ was removed by coevaporation with toluene. The black residue was treated with 50 ml of DCM and 50 ml of a water/ice mixture. After stirring for 15 min, the mixture was diluted with 400 ml of water and 400 ml of DCM. The organic layer was separated and washed with 300 ml of water. The aqueous layer was extracted with 400 ml of DCM. The combined DCM layers were dried over $Na_2SO_4$ and the solvent was removed to a volume of about 100 ml. The remaining solution was filtered through 50 g of silica gel eluting with DCM. The filtrate was evaporated. The resulting residue was suspended in 50 ml of diethyl ether. The solid was filtered off and dried to give 13.85 g of 4,6-dichloro-5-(o-methoxyphenoxy)-2-(N-morpholino)-pyrimidine as a white crystalline powder.

c) To a suspension of 4 g of 4,6-dichloro-5-(o-methoxyphenoxy)-2-(N-morpholino)-pyrimidine in 60 ml of DMSO was added 5.32 g of 5-isopropyl-2-pyridine sulfonamide potassium salt (Example 3c) and 0.98 ml of Hünig's base. The mixture was stirred at 65° C. for 72 h. The dark solution was poured onto 500 ml of water and quickly filtered through celite. The filtrate was extracted with 500 ml and 250 ml of diethyl ether. The organic layers were extracted with 100 ml of water. The aqueous layers were combined, acidified with 3.5 ml of acetic acid and cooled to 0° C. The precipitate that formed was collected, washed with cold water and dried under high vacuum to furnish 4.94 g of 5-isopropyl-N-[6-chloro-5-(o-methoxyphenoxy)-2-(N-morpholino)-4-pyrimidinyl]-2-pyridine sulfonamide as a brownish powder. LC-MS: $t_R$=5.46 min, $[M+1]^+$=520.22, $[M-1]^-$=518.36.

d) According to the procedure described in Example 1a) 260 mg 5-isopropyl-N-[6-chloro-5-(o-methoxyphenoxy)-2-(N-morpholino)-4-pyrimidinyl]-2-pyridine sulfonamide was reacted with 630 mg N-(3-hydroxy-propyl)4-methylbenzenesulfonamide in THF in the presence of potassium tert.-butylate to give 270 mg 5-isopropyl-N-[6-(3-((4-methylbenzene)-sulfonylamino)-propoxy)-5-(o-methoxyphenoxy)-2-(N-morpholino)-4-pyrimidinyl]-2-pyridine sulfonamide. LC-MS: $t_R$=5.27 min, $[M+1]^+$=713.67, $[M-1]^-$=711.71.

Example 53

According to the procedure described in Example 4a) 100 mg 5-i.-propyl-N-[6-(2-aminoethoxy)-5-(o-methoxyphenoxy)-2-trifluoromethyl-4-pyrimidinyl]pyridine-2-sulfonamide was reacted with 4-methylbenzene-sulfonylchloride to give 120 mg 5-i.-propyl-N-[6-(2-((4-methylbenzene)-sulfonylamino)-ethoxy)-5-(o-methoxyphenoxy)-2-trifluoromethyl-4-pyrimidinyl]pyridine-2-sulfonamide. LC-MS: $t_R$=5.61 min, $[M+1]^+$=682.51, $[M-1]^-$=680.50.

Example 54

According to the procedure described in Example 4a) 100 mg 5-i.-propyl-N-[6-(2-aminoethoxy)-5-(o-methoxyphenoxy)-2-trifluoromethyl-4-pyrimidinyl]pyridine-2-sulfonamide was reacted with thiophene-2-sulfonylchloride to give 125 mg 5-i.-propyl-N-[6-(2-((2-thiophene)-sulfonylamino)-ethoxy)-5-(o-methoxyphenoxy)-2-trifluoromethyl-4-pyrimidinyl]pyridine-2-sulfonamide. LC-MS: $t_R$=5.41 min, $[M+1]^+$=674.41, $[M-1]^-$=672.46.

Example 55

According to the procedure described in Example 4a) 100 mg 5-i.-propyl-N-[6-(2-aminoethoxy)-5-(o-methoxyphenoxy)-2-trifluoromethyl-4-pyrimidinyl]pyridine-2-sulfonamide was reacted with ethanesulfonylchloride to give 112 mg 5-i.-propyl-N-[6-(2-(ethanesulfonylamino)-ethoxy)-5-(o-methoxyphenoxy)-2-trifluoromethyl-4-pyrimidinyl]pyridine-2-sulfonamide. LC-MS: $t_R$=5.11 min, $[M+1]^+$=620.41, $[M-1]^-$=618.49.

Example 56

According to the procedure described in Example 4a) 100 mg 5-i.-propyl-N-[6-(2-aminoethoxy)-5-(o-methoxyphenoxy)-2-trifluoromethyl-4-pyrimidinyl]pyridine-2-sulfonamide was reacted with methanesulfonylchloride to give 110 mg 5-i.-propyl-N-[6-(2-(methanesulfonylamino)-ethoxy)-5-(o-methoxyphenoxy)-2-trifluoromethyl-4-pyrimidinyl]pyridine-2-sulfonamide. LC-MS: $t_R$=4.99 min, $[M+1]^+$=606.39, $[M-1]^-$=605.45.

Example 57 a) To a suspension of 1 g of 4,6-dichloro-5-(o-methoxyphenoxy)-2-(N-morpholino)-pyrimidine in 20 ml of DMSO was added 1.18 g of 5-methyl-2-pyridine sulfonamide potassium salt and 0.5 ml of Hünig's base. The mixture was stirred at 55° C. for 72 h. The dark solution was poured onto 500 ml of water and quickly filtered through celite. The filtrate was extracted with 500 ml and 250 ml of diethyl ether. The organic layers were extracted with 100 ml of water. The aqueous layers were combined, acidified with 3.5 ml of acetic acid and cooled to 0° C. The precipitate that formed was collected, washed with cold water and dried under high vacuum to furnish 730 mg of 5-methyl-N-[6-chloro-5-(o-methoxyphenoxy)-2-(N-morpholino)-4-pyrimidinyl]-2-pyridine sulfonamide as a brownish powder. LC-MS: $t_R$=0.70 min, $[M+1]^+$=492.43, $[M-1]^-$=490.54.

b) According to the procedure described in Example 4b) 725 mg 5-methyl-N-[6-chloro-5-(o-methoxyphenoxy)-2-(N-morpholino)-4-pyrimidinyl]-2-pyridine sulfonamide was reacted with 2-aminoethanol to give 250 mg 5-methyl-N-[6-(2-aminoethoxy)-5-(o-methoxyphenoxy)-2-(N-morpholino)-4-pyrimidinyl]-2-pyridine sulfonamide. LC-MS: $t_R$=3.14 min, $[M+1]^+$=517.54, $[M-1]^-$=515.63.

c) According to the procedure described in Example 4a) 75 mg 5-methyl-N-[6-(2-aminoethoxy)-5-(o-methoxyphenoxy)-2-(N-morpholino)-4-pyrimidinyl]-2-pyridine sulfonamide was reacted with benzenesulfonylchloride to give 85 mg 5-methyl-N-[6-(2-(benzenesulfonylamino)-ethoxy)-5-(o-methoxyphenoxy)-2-(N-morpholino)-4-pyrimidinyl]-2-pyridine sulfonamide. LC-MS: $t_R$=4.86 min, $[M+1]^+$=657.59.

Example 58

According to the procedure described in Example 4a) 75 mg 5-methyl-N-[6-(2-aminoethoxy)-5-(o-methoxyphenoxy)-2-(N-morpholino)-4-pyrimidinyl]-2-pyridine sulfonamide was reacted with thiophene-2-sulfonylchloride to give 85 mg 5-methyl-N-[6-(2-(thiophene-2-sulfonylamino)-ethoxy)-5-(o-methoxyphenoxy)-2-(N-morpholino)-4-pyrimidinyl]-2-pyridine sulfonamide. LC-MS: $t_R$=4.79 min, $[M+1]^+$=663.53.

Example 59

According to the procedure described in Example 4a) 362 mg 5-methyl-N-[6-(2-aminoethoxy)-5-(o-methoxyphenoxy)-2-(N-morpholino)-4-pyrimidinyl]-2-pyridine sulfonamide was reacted with 1-propanesulfonylchloride to give 85 mg 5-methyl-N-[6-(2-(1-propanesulfonylamino)-ethoxy)-5-(o-methoxyphenoxy)-2-(N-morpholino)-4-pyrimidinyl]-2-pyridine sulfonamide. LC-MS: $t_R$=4.55 min, $[M+1]^+$=623.55, $[M-1]^-$=621.59.

Example 60

According to the procedure described in Example 4a) 75 mg 5-isopropyl-N-[6-(2-aminoethoxy)-5-(o-methoxyphenoxy)-2-(N-morpholino)-4-pyrimidinyl]-2-pyridine sulfonamide was reacted with 4-methylbenzenesulfonylchloride to give 77 mg 5-isopropyl-N-[6-(2-(4-methylbenzenesulfonylamino)-ethoxy)-5-(o-methoxyphenoxy)-2-(N-morpholino)-4-pyrimidinyl]-2-pyridine sulfonamide. LC-MS: $t_R$=5.28 min, $[M+1]^+$=699.70, $[M-1]^-$=697.79.

Example 61

According to the procedure described in Example 4a) 75 mg 5-isopropyl-N-[6-(2-aminoethoxy)-5-(o-methoxyphenoxy)-2-(N-morpholino)-4-pyrimidinyl]-2-pyridine sulfonamide was reacted with ethanesulfonylchloride to give 67 mg 5-isopropyl-N-[6-(2-(ethanesulfonylamino)-ethoxy)-5-(o-methoxyphenoxy)-2-(N-morpholino)-4-pyrimidinyl]-2-pyridine sulfonamide. LC-MS: $t_R$=4.73 min, $[M+1]^+$=637.64, $[M-1]^-$=635.74.

Example 62 a) A solution of 10 g of dimethyl-(o-methoxyphenoxy)malonate in 80 ml dry methanol was cooled to 0° C. 6.71 g of sodium methylate was added portionwise. To the suspension was added 2.84 g of acetamidine hydrochloride and the mixture was stirred overnight at room temperature. The solvent was removed under reduced pressure and the residue was suspended in 100 ml of diethyl ether. The solid was filtered off, washed with another portion of 100 ml of diethyl ether and dissolved in 50 ml of water. The pH was adjusted to 4 by adding 25 ml of glacial acetic acid. The white precipitate that formed was filtered off, washed with water and dried to yield 5.17 g of 5-(o-methoxyphenoxy)-4,6-dihydroxy-2-methyl-pyrimidine (or a tautomer) as a white powder.

b) A solution of 10.9 g of 5-(o-methoxyphenoxy)-4,6-dihydroxy-2-methyl-pyrimidine (or a tautomer) in 150 ml of POCl$_3$ was stirred at 50° C. for 72 h. The excess of POCl$_3$ was evaporated, toluene was added to coevaporate traces of POCl$_3$. Eventually, an ice/water mixture was carefully added to the residue and the pH was adjusted to 8 using 3 N sodium hydroxide solution. The mixture was further diluted with 300 ml of water and extracted with 500 ml of DCM. The organic layer was separated, washed with 300 ml of water, dried over Na$_2$SO$_4$ and evaporated. The residue was dissolved again in DCM and filtered through a pad of silica gel eluting with DCM. The solvent was removed in vacuo. The resulting residue was dried to furnish 8.7 g of 4,6-dichloro-5-(o-methoxyphenoxy)-2-methyl-pyrimidine as a beige powder.

c) To a solution of 1.0 g of 4,6-dichloro-5-(o-methoxyphenoxy)-2-methyl-pyrimidine in 20 ml of DMSO was added 1.76 g of 4-tert.-butyl-benzene sulfonamide potassium salt. The mixture was stirred for 72 h at room temperature. The solution was diluted with 250 ml of water and extracted twice with 200 ml of diehtyl ether. The organic layers were extracted twice with water. The combined aqueous layers were acidified to pH 4 with 5 ml of acetic acid and cooled to 0° C. The precipitated product was filtered off and dried in vacuo to give 1.05 g of 4-tert.-butyl-N-[6-chloro-5-(o-methoxyphenoxy)-2-methyl-4-pyrimidinyl]-benzene sulfonamide as a pale beige powder. LC-MS: $t_R$=5.64 min, $[M+1]^+$=462.51, $[M-1]^-$=460.63.

d) According to a procedure described in Example 4b) 0.5 g 4-tert.-butyl-N-[6-chloro-5-(o-methoxyphenoxy)-2-methyl-4-pyrimidinyl]-benzene sulfonamide was reacted with 2-aminoethanol to give 560 mg 4-tert.-butyl-N-[6-(2-aminoethoxy)-5-(o-methoxyphenoxy)-2-methyl-4-pyrimidinyl]-benzene sulfonamide. LC-MS: $t_R$=3.84 min, $[M+1]^+$=487.51, $[M-1]^-$=485.54.

e) According to the procedure described in Example 4a) 103 mg 4-tert.-butyl-N-[6-(2-aminoethoxy)-5-(o-methoxyphenoxy)-2-methyl-4-pyrimidinyl]-benzene sulfonamide was reacted with thiophene-2-sulfonylchloride to give 95 mg 4-tert.-butyl-N-[6-(2-(2-thiophenesulfonylamino)-ethoxy)-5-(o-methoxyphenoxy)-2-methyl-4-pyrimidinyl]-benzene sulfonamide. LC-MS: $t_R$=5.60 min, $[M+1]^+$=633.60, $[M-1]^-$=631.70.

Example 63

According to the procedure described in Example 4a) 103 mg 4-tert.-butyl-N-[6-(2-aminoethoxy)-5-(o- methoxyphenoxy)-2-methyl-4-pyrimidinyl]-benzene sulfonamide was reacted with ethanesulfonylchloride to give 92 mg 4-tert.-butyl-N-[6-(2-(ethanesulfonylamino)-ethoxy)-5-(o-methoxyphenoxy)-2-methyl-4-pyrimidinyl]-benzene sulfonamide. LC-MS: $t_R$=5.12 min, [M+1]$^+$=579.60, [M–1]$^-$=577.72.

Example 64

According to the procedure described in Example 4a) 103 mg 4-tert.-butyl-N-[6-(2-aminoethoxy)-5-(o-methoxyphenoxy)-2-methyl-4-pyrimidinyl]-benzene sulfonamide was reacted with methanesulfonylchloride to give 105 mg 4-tert.-butyl-N-[6-(2-(methanesulfonylamino)-ethoxy)-5-(o-methoxyphenoxy)-2-methyl-4-pyrimidinyl]-benzene sulfonamide. LC-MS: $t_R$=5.12 min, [M+1]$^+$= 565.58, [M–1]$^-$=563.69.

Example 65

According to the procedure described in Example 1a) 256 mg 5-isopropyl-N-[6-chloro-5-(o-methoxyphenoxy)-2-(4-pyridyl)-4-pyrimidinyl]-2-pyridine sulfonamide was reacted with N-(3-hydroxy-propyl)-4-methylbenzenesulfonamide in THF in the presence of potassium tert.-butylate to give 280 mg 5-isopropyl-N-[6-(3-(4-methylbenzenesulfonylamino)-propoxy)-5-(o-methoxyphenoxy)-2-methyl-4-pyrimidinyl]-2-pyridine sulfonamide. LC-MS: $t_R$=4.83 min, [M+1]$^+$= 705.70, [M–1]$^-$=703.79.

Example 66 a) According to the procedure described in Example 1g) 1.00 g 5-(o-methoxyphenoxy)-4,6-dichloro-2-methyl-pyrimidine was reacted with 5-methyl-2-pyridine sulfonamide potassium salt to give 1.5 g 5-methyl-N-[6-chloro-5-(o-methoxyphenoxy)-2-methyl-4-pyrimidinyl]-2-pyridine sulfonamide. LC-MS: $t_R$=4.57 min, [M+1]$^+$=421.42, [M–1]$^-$=419.46.

b) According to the procedure described in Example 4b) 1.00 g 5-methyl-N-[6-chloro-5-(o-methoxyphenoxy)-2-methyl-4-pyrimidinyl]-2-pyridine sulfonamide was reacted with 2-aminoethanol to give 1.05 g 5-methyl-N-[6-(2-aminoethoxy)-5-(o-methoxyphenoxy)-2-methyl-4-pyrimidinyl]-2-pyridine sulfonamide. LC-MS: $t_R$=2.93 min, [M+1]$^+$=446.51, [M–1]$^-$=444.53.

c) According to the procedure described in Example 4a) 94 mg 5-methyl-N-[6-(2-aminoethoxy)-5-(o-methoxyphenoxy)-2-methyl-4-pyrimidinyl]-2-pyridine sulfonamide was reacted with 4-methylbenzenesulfonylchloride to give 82 mg 5-methyl-N-[6-(2-(4-methylbenzenesulfonylamino)-ethoxy)-5-(o-methoxyphenoxy)-2-methyl-4-pyrimidinyl]-2-pyridine sulfonamide. LC-MS: $t_R$=4.86 min, [M+1]$^+$=600.59, [M–1]$^-$= 598.55.

Example 67

According to the procedure described in Example 4a) 94 mg 5-methyl-N-[6-(2-aminoethoxy)-5-(o-methoxyphenoxy)-2-methyl-4-pyrimidinyl]-2-pyridine sulfonamide was reacted with benzenesulfonylchloride to give 67.2 mg 5-methyl-N-[6-(2-(benzenesulfonylamino)-ethoxy)-5-(o-methoxyphenoxy)-2-methyl-4-pyrimidinyl]-2-pyridine sulfonamide. LC-MS: $t_R$=4.68 min, [M+1]$^+$= 586.39, [M–1]$^-$=584.42.

Example 68

According to the procedure described in Example 4a) 129 mg 5-isopropyl-N-[6-(2-aminoethoxy)-5-(o-methoxyphenoxy)-2-(2-pyrimidinyl)-4-pyrimidinyl]-2-pyridine sulfonamide was reacted with thiophene-2-sulfonylchloride to give 105 mg 5-isopropyl-N-[6-(2-(2-thiophenesulfonylamino)-ethoxy)-5-(o-methoxyphenoxy)-2-(2-pyrimidinyl)-4-pyrimidinyl]-2-pyridine sulfonamide. LC-MS: $t_R$=5.00 min, [M+1]$^+$=684.60, [M–1]$^-$=682.70.

Example 69

According to the procedure described in Example 4a) 129 mg 5-isopropyl-N-[6-(2-aminoethoxy)-5-(o-methoxyphenoxy)-2-(2-pyrimidinyl)-4-pyrimidinyl]-2-pyridine sulfonamide was reacted with 4-methylbenzenesulfonylchloride to give 104 mg 5-isopropyl-N-[6-(2-(4-methylbenzenesulfonylamino)-ethoxy)-5-(o-methoxyphenoxy)-2-(2-pyrimidinyl)-4-pyrimidinyl]-2-pyridine sulfonamide. LC-MS: $t_R$=5.04 min, [M+1]$^+$=692.65, [M–1]$^-$=690.76.

Example 70

According to the procedure described in Example 4a) 129 mg 5isopropyl-N-[6-(2-aminoethoxy)-5-(o-methoxyphenoxy)-2-(2-pyrimidinyl)-4-pyrimidinyl]-2-pyridine sulfonamide was reacted with ethanesulfonylchloride to give 130 mg 5-isopropyl-N-[6-(2-(ethanesulfonylamino)-ethoxy)-5-(o-methoxyphenoxy)-2-(2-pyrimidinyl)-4-pyrimidinyl]-2-pyridine sulfonamide. LC-MS: $t_R$=4.54 min, [M+1]$^+$=630.59, [M–1]$^-$=628.69.

Example 71

According to the procedure described in Example 4a) 100 mg 5isopropyl-N-[6-(2-aminoethoxy)-5-(o-methoxyphenoxy)-2-(4-pyridyl)-4-pyrimidinyl]-2-pyridine sulfonamide was reacted with thiophene-2-sulfonylchloride to give 85 mg 5-isopropyl-N-[6-(2-(2-thiophenesulfonylamino)-ethoxy)-5-(o-methoxyphenoxy)-2-(2-pyridyl)-4-pyrimidinyl]-2-pyridine sulfonamide. LC-MS: $t_R$=4.78 min, [M+1]$^+$=683.61, [M–1]$^-$=681.70.

Example 72

According to the procedure described in Example 4a) 100 mg 5-isopropyl-N-[6-(2-aminoethoxy)-5-(o-methoxyphenoxy)-2-(4-pyridyl)-4-pyrimidinyl]-2-pyridine sulfonamide was reacted with 1-propanesulfonylchloride to give 76 mg 5-isopropyl-N-[6-(2-(1-propanesulfonylamino)-ethoxy)-5-(o-methoxyphenoxy)-2-(2-pyridyl)-4-pyrimidinyl]-2-pyridine sulfonamide. LC-MS: $t_R$=4.56 min, [M+1]$^+$=643.65, [M–1]$^-$=641.70.

Example 73

According to the procedure described in Example 4a) 100 mg 5-isopropyl-N-[6-(2-aminoethoxy)-5-(o-methoxyphenoxy)-2-(4-pyridyl)-4-pyrimidinyl]-2-pyridine sulfonamide was reacted with ethanesulfonylchloride to give 83 mg 5-isopropyl-N-[6-(2-(ethanesulfonylamino)-ethoxy)-5-(o-methoxyphenoxy)-2-(2-pyridyl)-4-pyrimidinyl]-2-pyridine sulfonamide. LC-MS: $t_R$=4.28 min, [M+1]$^+$=629.63, [M–1]$^-$=627.73.

Example 74

According to the procedure described in Example 4a) 100 mg 5-isopropyl-N-[6-(2-aminoethoxy)-5-(o-methoxyphenoxy)-2-(4-pyridyl)-4-pyrimidinyl]-2-pyridine sulfonamide was reacted with trifluoromethanesulfonylchloride to give 83 mg 5-isopropyl-N-[6-(2-

(trifluoromethanesulfonylamino)-ethoxy)-5-(o-methoxyphenoxy)-2-(2-pyridyl)-4-pyrimidinyl]-2-pyridine sulfonamide. LC-MS: $t_R$=5.02 min, [M+1]$^+$=669.59, [M−1]$^−$=667.68.

Example 75 a) Under argon 4 g of 4,6-dichloro-5-(o-methoxyphenoxy)-2-(4-pyridyl)-pyrimidine (Example 1b to e) was dissolved in 40 ml of dry DMF and 3.62 g of 5-methylpyridine-2-sulfonamide potassium salt followed by 2.95 ml of Hünig's base was added. The dark solution was stirred at room temperature for 22 h. A further portion of 0.75 g of 5-methylpyridine-2-sulfonamide potassium salt was added and stirring was continued for 18 h. The reaction mixture was poured onto 150 ml of 10% citric acid in water and extracted four times with 150 ml of ethyl acetate. The combined organic layers were washed with water, dried over MgSO$_4$, and evaporated. The resulting residue was suspended in 20 ml of methanol and 20 ml of acetone. The precipitate was collected, washed with methanol/diethyl ether 1/1 and dried. This furnished 4.56 g of 5-methyl-N-[6-chloro-5-(o-methoxyphenoxy)-2-(4-pyridyl)-4-pyrimidinyl]-2-pyridine sulfonamide as a beige powder. LC-MS: $t_R$=4.38 min, [M+1]$^+$=484.58, [M−1]$^−$=482.51.

b) According to the procedure described in Example 4b) 1.0 g 5-methyl-N-[6-chloro-5-(o-methoxyphenoxy)-2-(4-pyridyl)-4-pyrimidinyl]-2-pyridine sulfonamide was reacted with 2-aminoethanol to give 950 mg 5-methyl-N-[6-(2-aminoethoxy)-5-(o-methoxyphenoxy)-2-(4-pyridyl)-4-pyrimidinyl]-2-pyridine sulfonamide. LC-MS: $t_R$=3.00 min, (M+1]$^+$=509.53, [M−1]$^−$=507.57.

c) According to the procedure described in Example 4a) 107 mg 5-methyl-N-[6-(2-aminoethoxy)-5-(o-methoxyphenoxy)-2-(4-pyridyl)-4-pyrimidinyl]-2-pyridine sulfonamide was reacted with 4-methylbenzenesulfonylchloride to give 70 mg 5-methyl-N-[6-(2-(4-methylbenzenesulfonylamino)-ethoxy)-5-(o-methoxyphenoxy)-2-(4-pyridyl)-4-pyrimidinyl]-2-pyridine sulfonamide. LC-MS: $t_R$=4.55 min [M+1]$^+$663.56, [M−1]$^−$= 661.63.

Example 76

According to the procedure described in Example 4a) 107 mg 5-methyl-N-[6-(2-aminoethoxy)-5-(o-methoxyphenoxy)-2-(4-pyridyl)-4-pyrimidinyl]-2-pyridine sulfonamide was reacted with thiophene-2-sulfonylchloride to give 135 mg 5-methyl-N-[6-(2-(2-thiophenesulfonylamino)-ethoxy)-5-(o-methoxyphenoxy)-2-(4-pyridyl)-4-pyrimidinyl]-2-pyridine sulfonamide. LC-MS: $t_R$=4.33 min, [M+1]$^+$=655.46, [M−1]$^−$=653.50.

Example 77

According to the procedure described in Example 4a) 107 mg 5-methyl-N-[6-(2-aminoethoxy)-5-(o-methoxyphenoxy)-2-(4-pyridyl)-4-pyrimidinyl]-2-pyridine sulfonamide was reacted with ethanesulfonylchloride to give 100 mg 5-methyl-N-[6-(2-(ethanesulfonylamino)-ethoxy)-5-(o-methoxyphenoxy)-2-(4-pyridyl)-4-pyrimidinyl]-2-pyridine sulfonamide. LC-MS: $t_R$=3.89 min, [M+1]$^+$=601.50, [M−1]$^−$=599.53.

Example 78

According to the procedure described in Example 4a) 107 mg 5-methyl-N-[6-(2-aminoethoxy)-5-(o-methoxyphenoxy)-2-(4-pyridyl)-4-pyrimidinyl]-2-pyridine sulfonamide was reacted with methanesulfonylchloride to give 100 mg 5-methyl-N-[6-(2-(methanesulfonylamino)-ethoxy)-5-(o-methoxyphenoxy)-2-(4-pyridyl)-4-pyrimidinyl]-2-pyridine sulfonamide. LC-MS: $t_R$=3.72 min, [M+1]$^+$=587.46, [M−1]$^−$=585.50.

Example 79

According to the procedure described in Example 4a) 200 mg p-tert.-butyl-N-[6-(3-aminopropoxy)-5-(o-methoxyphenoxy)-2-cyclopropyl-4-pyrimidinyl]benzene-sulfonamide was reacted with ethanesulfonylchloride to give 220 mg p-tert.-butyl-N-[6-(3-ethansulfonylamino)-propoxy)-5-(o-methoxyphenoxy)-2-cyclopropyl-4-pyrimidinyl]benzene-sulfonamide. LC-MS: $t_R$=5.74 min, [M+1]$^+$=619.22, [M−1]$^−$=617.24.

Example 80

According to the procedure described in Example 4a) 200 mg p-tert.-butyl-N-[6-(3-aminopropoxy)-5-(o-methoxyphenoxy)-2-cyclopropyl-4-pyrimidinyl]benzene-sulfonamide was reacted with thiophene-2-sulfonylchloride to give 144 mg p-tert.-butyl-N-[6-(3-(2-thiophene-sulfonylamino)-propoxy)-5-(o-methoxyphenoxy)-2-cyclopropyl-4-pyrimidinyl]benzene-sulfonamide. LC-MS: $t_R$=6.06 min, [M+1]$^+$=673.20, [M−1]$^−$=671.24.

Example 81

100 mg 4-tert.-butyl-N-[6-(2-ethanesulfonylamino-ethoxy)-2-methanesulfonyl-5-(o-methoxyphenoxy-pyrimidin-4-yl]-benzenesulfonamide was heated to 120° C. in 0.5 ml morpholine for 6 h. The reaction mixture was poured onto water, acidified with citric acid to pH 4 and extracted with ethyl acetate. The combined organic layers were dried with magnesium sulfate and evaporated at reduced pressure to give 110 mg 4-tert.-butyl-N-[6-(2-ethanesulfonylamino-ethoxy)-2-(N-morpholino)-5-(o-methoxyphenoxy)-pyrimidin-4-yl]-benzenesulfonamide. LC-MS: $t_R$=5.43 min, [M+1]$^+$=650.35, [M−1]$^−$=648.45.

Example 82

According to the procedure described in Example 81) 76 mg 4-tert.-butyl-N-[6-(2-ethanesulfonylamino-ethoxy)-2-methanesulfonyl-5-(o-methoxyphenoxy-pyrimidin-4-yl]-benzenesulfonamide was reacted with N-methyl-piperazine to give 35 mg 4-tert.-butyl-N-[6-(2-ethanesulfonylamino-ethoxy)-2-(N-(N'-methyl)-piperazinyl)-5-(o-methoxyphenoxy)-pyrimidin-4-yl]-benzene-sulfonamide. LC-MS: $t_R$=3.87 min, [M+1]$^+$=663.38, [M−1]$^−$=661.50.

Example 83

According to the procedure described in Example 4a) 60 mg 5-i.-propyl-N-[6-(2-aminoethoxy)-5-(o-methoxyphenoxy)-2-cyclopropyl-4-pyrimidinyl]pyridine-2-sulfonamide was reacted with ethanesulfonylchloride to give 45 mg 5-i.-propyl-N-[6-(2-(ethanesulfonylamino)-ethoxy)-5-(o-methoxyphenoxy)-2-cyclopropyl-4-pyrimidinyl]pyridine-2-sulfonamide. LC-MS: $t_R$=4.67 min, [M+1]$^+$=564.28, [M−1]$^−$=562.41.

Example 84

According to the procedure described in Example 4a) 60 mg 5-i.-propyl-N-[6-(2-aminoethoxy)-5-(o-methoxyphenoxy)-2-cyclopropyl-4-pyrimidinyl]pyridine-2-sulfonamide was reacted with 1-propanesulfonylchloride to give 42 mg 5-i.-propyl-N-[6-(2-(1-propanesulfonylamino)-ethoxy)-5-(o-methoxyphenoxy)-2-cyclopropyl-4-pyrimidinyl]pyridine-2-sulfonamide. LC-MS: $t_R$=4.88 min, $[M+1]^+$=578.30, $[M-1]^-$=576.43.

Example 85

According to the procedure described in Example 4a) 60 mg 5-i.-propyl-N-[6-(2-aminoethoxy)-5-(o-methoxyphenoxy)-2-cyclopropyl-4-pyrimidinyl]pyridine-2-sulfonamide was reacted with thiophene-2-sulfonylchloride to give 48 mg 5-i.-propyl-N-[6-(2-(2-thiophenesulfonylamino)-ethoxy)-5-(o-methoxyphenoxy)-2-cyclopropyl-4-pyrimidinyl]pyridine-2-sulfonamide. LC-MS: $t_R$=5.06 min, $[M+1]^+$=618.26, $[M-1]^-$=616.39.

Example 86

According to the procedure described in Example 4a) 60 mg 5-i.-propyl-N-[6-(2-aminoethoxy)-5-(o-methoxyphenoxy)-2-cyclopropyl-4-pyrimidinyl]pyridine-2-sulfonamide was reacted with 2-propanesulfonylchloride to give 52 mg 5-i.-propyl-N-[6-(2-(2-propanesulfonylamino)-ethoxy)-5-(o-methoxyphenoxy)-2-cyclopropyl-4-pyrimidinyl]pyridine-2-sulfonamide. LC-MS: $t_R$=4.80 min, $[M+1]^+$=578.30, $[M-1]^-$=576.44.

Example 87

According to the procedure described in Example 4a) 200 mg 4-tert.-butyl-N-[6-(3-aminopropoxy)-5-(o-methoxyphenoxy)-2-cyclopropyl-4-pyrimidinyl]-benzene-sulfonamide was reacted with ethanesulfonylchloride to give 220 mg 4-tert.-butyl-N-[6-(3-(ethanesulfonylamino propoxy)-5-(o-methoxyphenoxy)-2-cyclopropyl-4-pyrimidinyl]-benzene-sulfonamide. LC-MS: $t_R$=5.74 min, $[M+1]^+$=619.22, $[M-1]^-$=617.24.

Example 88

According to the procedure described in Example 4a) 200 mg 4-tert.-butyl-N-[6-(3-aminopropoxy)-5-(o-methoxyphenoxy)-2-cyclopropyl-4-pyrimidinyl]-benzene-sulfonamide was reacted with 2-thiophenesulfonylchloride to give 144 mg 4-tert.-butyl-N-[6-(3-(2-thiophenesulfonylamino)-propoxy)-5-(o-methoxyphenoxy)-2-cyclopropyl-4-pyrimidinyl]-benzene-sulfonamide. LC-MS: $t_R$=6.06 min, $[M+1]^+$=673.20, $[M-1]^-$=671.24.

Example 89

According to the procedure described in Example 4a) 100 mg 4tert.-butyl-N-[6-(3-aminopropoxy)-5-(o-methoxyphenoxy)-2-pyrimidinyl-4-pyrimidinyl]-benzene-sulfonamide was reacted with ethanesulfonylchloride to give 33 mg 4-tert.-butyl-N-[6-(3-(ethanesulfonylamino)-propoxy)-5-(o-methoxyphenoxy)-2-pyrimidinyl-4-pyrimidinyl]-benzene-sulfonamide. LC-MS: $t_R$=5.25 min, $[M+1]^+$=657.33, $[M-1]^-$=655.45.

Example 90

According to the procedure described in Example 4a) 100 mg 4-tert.-butyl-N-[6-(3-aminopropoxy)-5-(o-methoxyphenoxy)-2-pyrimidinyl-4-pyrimidinyl]-benzene-sulfonamide was reacted with 2-thiophenesulfonylchloride to give 50 mg 4-tert.-butyl-N-[6-(3-(2-thiophenesulfonylamino)-propoxy)-5-(o-methoxyphenoxy)-2-pyrimidinyl-4-pyrimidinyl]-benzene-sulfonamide. LC-MS: $t_R$=5.63 min, $[M+1]^+$711.28, $[M-1]^-$=709.36.

Example 91

According to the procedure described in Example 4a) 195 mg 5-i.-propyl-N-[6-(3-aminopropoxy)-5-(o-methoxyphenoxy)-2-cyclopropyl-4-pyrimidinyl]-pyridine-2-sulfonamide was reacted with ethanesulfonylchloride to give 151 mg 5-i.-propyl-N-[6-(3-(ethanesulfonylamino)-propoxy)-5-(o-methoxyphenoxy)-2-cyclopropyl-4-pyrimidinyl]-pyridine-2-sulfonamide. LC-MS: $t_R$=5.13 min, $[M+1]^+$=606.37, $[M-1]^-$=604.51.

Example 92

According to the procedure described in Example 4a) 195 mg 5-i.-propyl-N-[6-(3-aminopropoxy)-5-(o-methoxyphenoxy)-2-cyclopropyl-4-pyrimidinyl]-pyridine-2-sulfonamide was reacted with propanesulfonylchloride to give 60 mg 5-i.-propyl-N-[6-(3-(propanesulfonylamino)-propoxy)-5-(o-methoxyphenoxy)-2-cyclopropyl-4-pyrimidinyl]-pyridine-2-sulfonamide. LC-MS: $t_R$=5.29 min, $[M+1]^+$=620.39, $[M-1]^-$=618.53.

Example 93

According to the procedure described in Example 4a) 195 mg 5-i.-propyl-N-[6-(3-aminopropoxy)-5-(o-methoxyphenoxy)-2-cyclopropyl-4-pyrimidinyl]-pyridine-2-sulfonamide was reacted with 2-thiophenesulfonylchloride to give 119 mg 5-i.-propyl-N-[6-(3-(2-thiophenesulfonylamino)-propoxy)-5-(o-methoxyphenoxy)-2-cyclopropyl-4-pyrimidinyl]-pyridine-2-sulfonamide. LC-MS: $t_R$=5.49 min, $[M+1]^+$=660.35, $[M-1]^-$=658.41.

Example 94

According to the procedure described in Example 4a) 195 mg 5-i.-propyl-N-[6-(3-aminopropoxy)-5-(o-methoxyphenoxy)-2-cyclopropyl-4-pyrimidinyl]-pyridine-2-sulfonamide was reacted with p-toluenesulfonylchloride to give 71 mg 5-i.-propyl-N-[6-(3-(p-toluenesulfonylamino)-propoxy)-5-(o-methoxyphenoxy)-2-cyclopropyl-4-pyrimidinyl]-pyridine-2-sulfonamide. LC-MS: $t_R$=5.64 min, $[M+1]^+$668.40, $[M-1]^-$=666.51.

Example 95

Using methods described in the above Examples, the compounds disclosed in Table 1 can be prepared:

TABLE 1
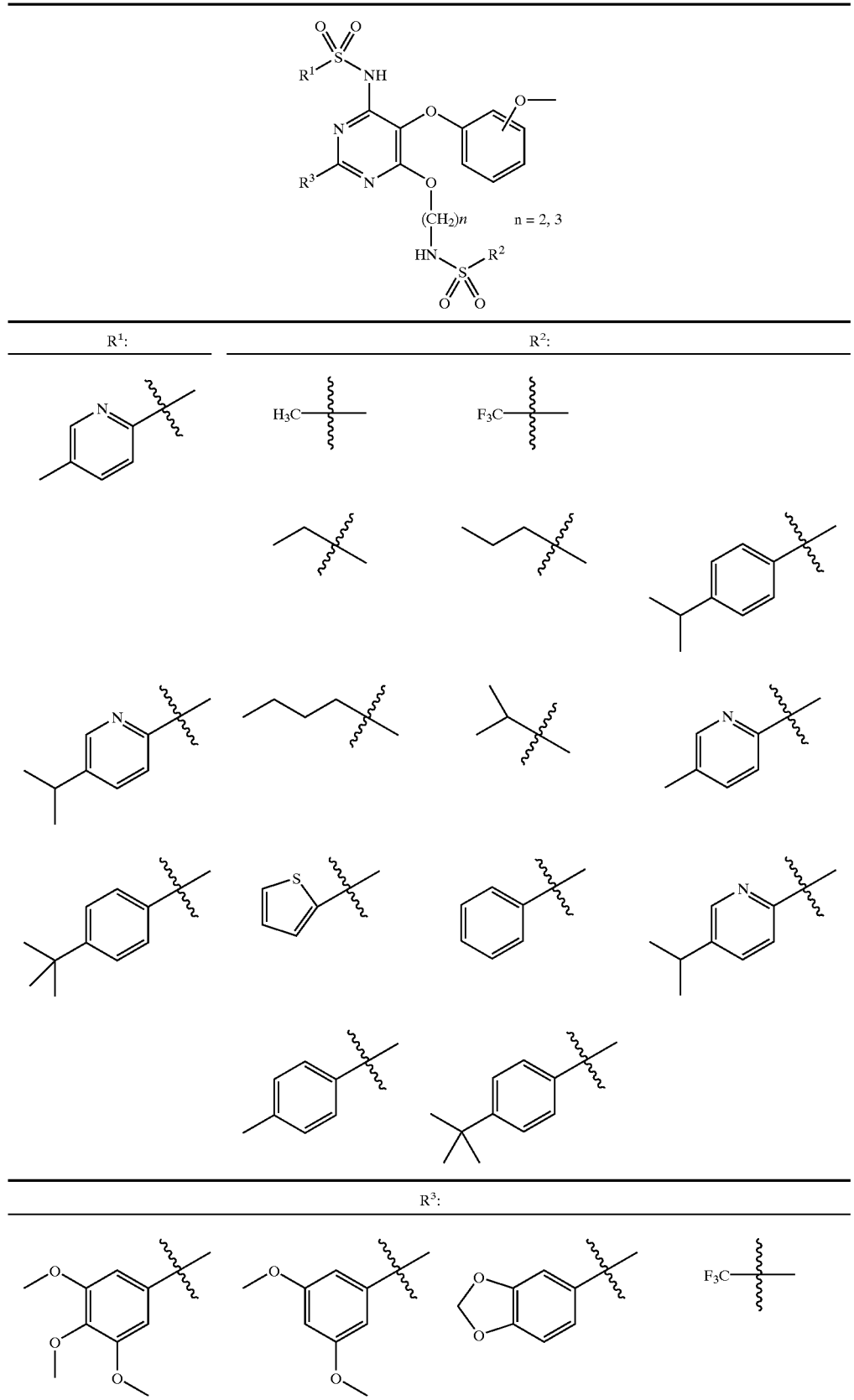

TABLE 1-continued
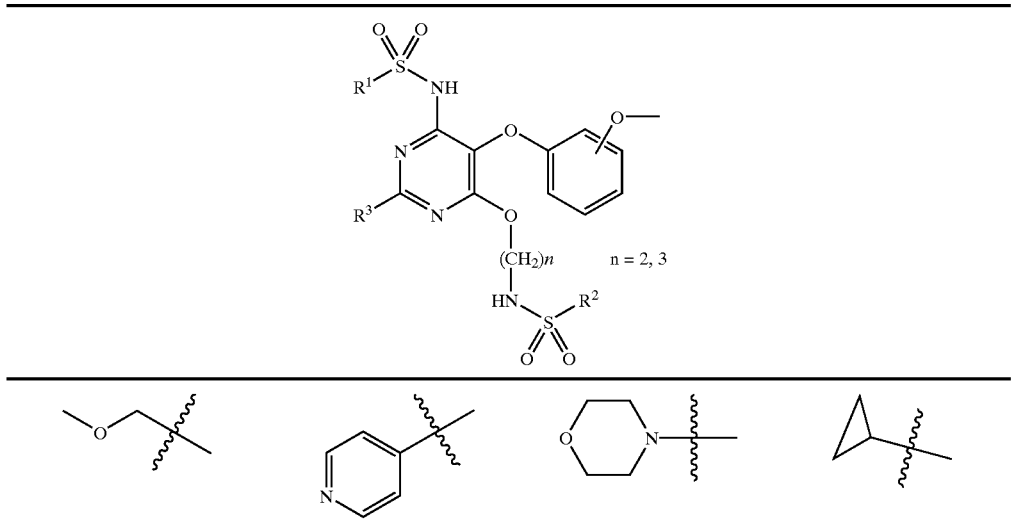
Example 96
Using methods described in the above Examples, the compounds disclosed in Table 2 can be prepared:
TABLE 2
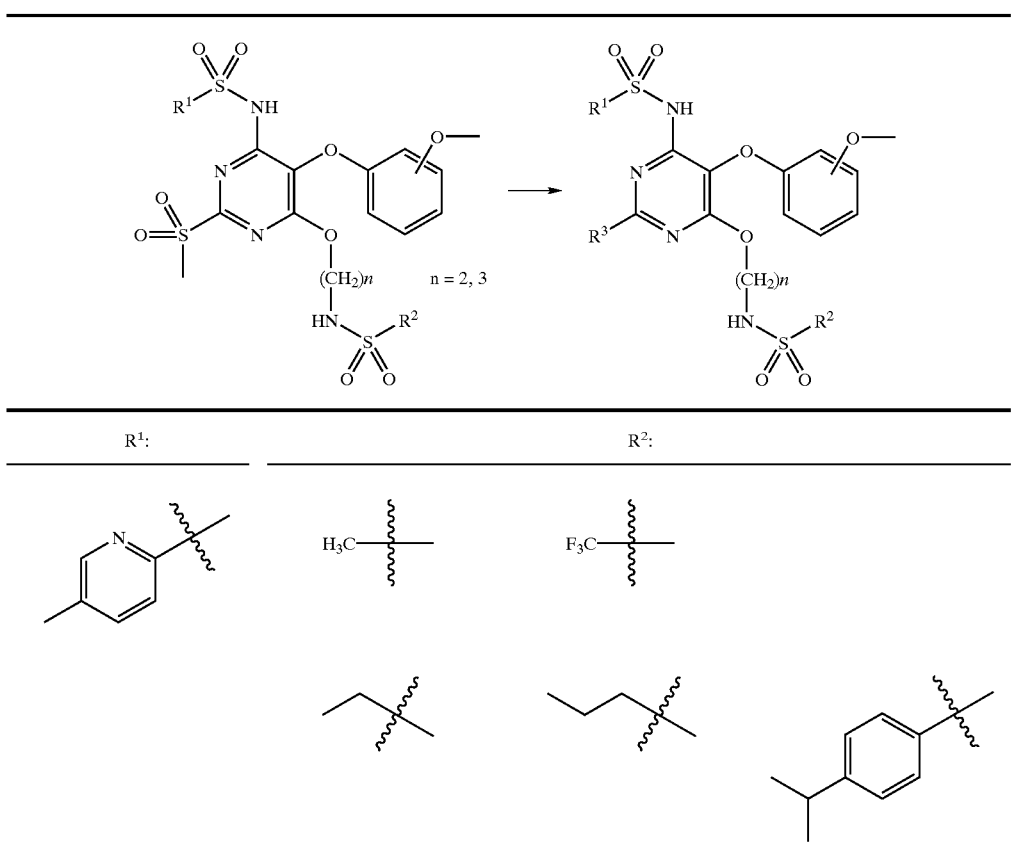

TABLE 2-continued
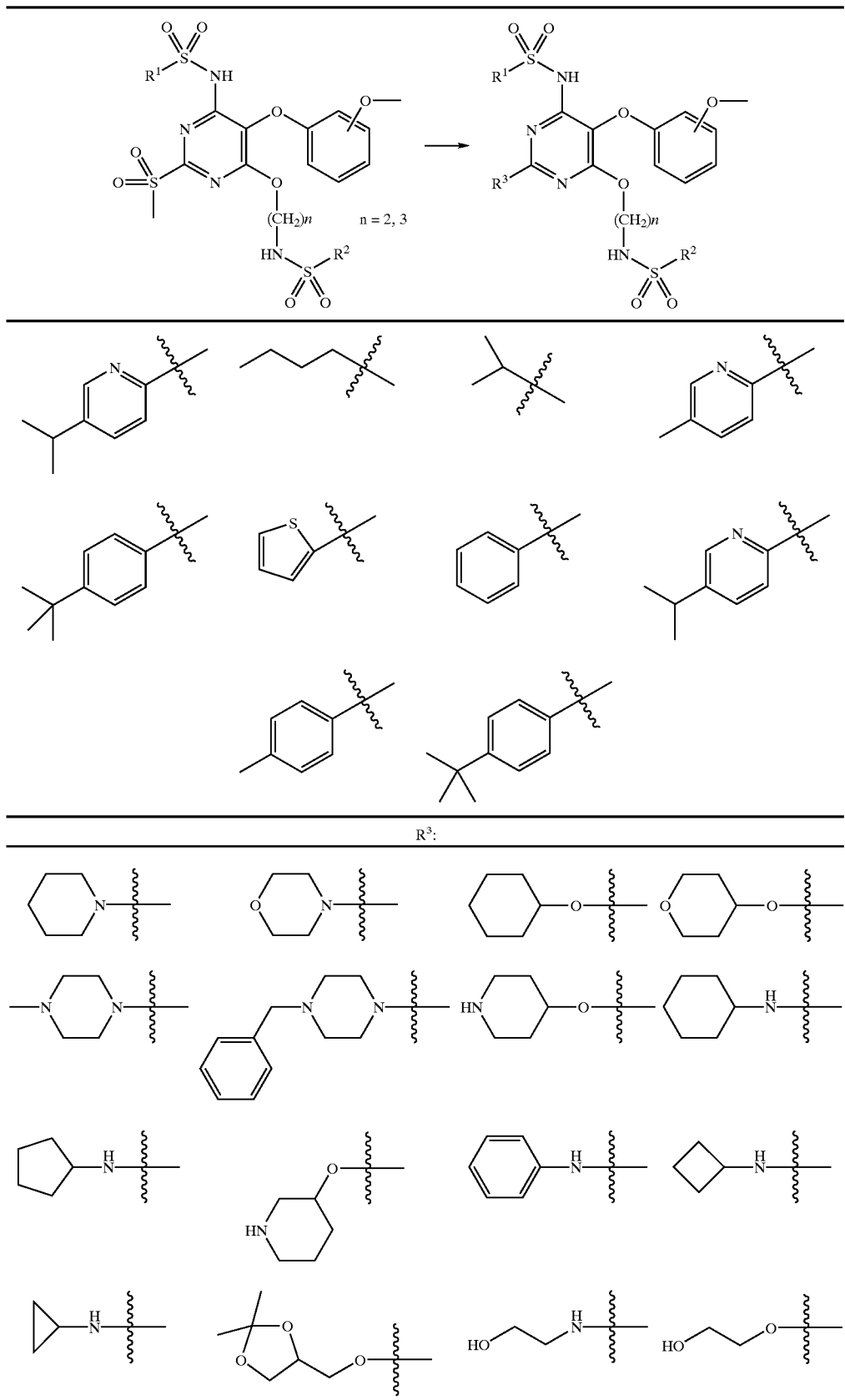

TABLE 2-continued

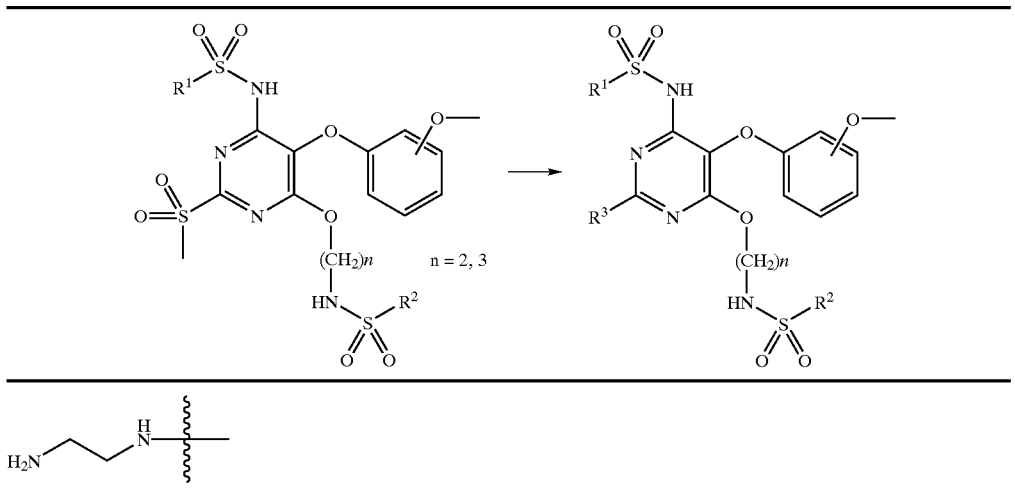

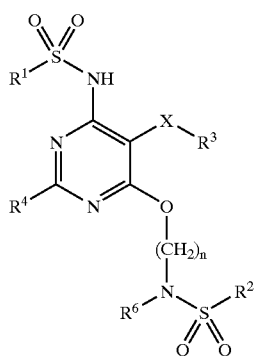

LIST OF ABBREVIATIONS

| EA | ethyl acetate |
|---|---|
| CyHex | cyclohexane |
| Hex | hexane |
| DMSO | dimethylsulfoxide |
| THF | tetrahydrofurane |
| MCPBA | m-chloroperbenzoic acid |
| DMF | dimethylformamide |
| DCM | dichloromethane |

What is claimed is:

1. A compound of formula I formula I and a pure diastereomer, a mixture of diastereomers, a diastereomeric racemate, a mixture of diastereomeric racemates and meso-forms and a pharmaceutically acceptable salt thereof,
wherein $R^1$ represents aryl; aryl-lower alkyl; aryl-lower alkenyl; heteroaryl; or heteroaryl-lower alkyl;

$R^2$ represents lower alkyl; trifluoromethyl; lower alkoxy-lower alkyl; lower alkenyl; lower alkynyl; aryl; aryl-lower alkyl; aryl-lower alkenyl; heterocyclyl; heterocyclyl-lower alkyl; heteroaryl; heteroaryl-lower alkyl; cycloalkyl; or cycloalkyl-lower alkyl;

$R^3$ represents phenyl; mono-, di- or tn-substituted phenyl substituted with lower alkyl, lower alkenyl, lower alkynyl, lower alkyloxy, amino, lower alkylamino, amino-lower alkyl, trifluoromethyl, trifluoromethoxy, halogen, lower alkylthio, hydroxy, hydroxy-lower alkyl, cyano, carboxyl, lower alkanoyl, formyl; benzofuranyl; aryl; or heteroaryl;

$R^4$ represents hydrogen; halogen; trifluoromethyl; lower alkyl; lower alkyl-amino; lower alkyloxy; lower alkyl-sulfono; lower alkyl-sulfinyl; lower alkylthio; lower alkylthio-lower alkyl; hydroxy-lower alkyl; lower alkyl-oxy-lower alkyl; hydroxy-lower alkyl-oxy-lower alkyl; hydroxy-lower alkyl-amino; lower alkyl-amino-lower alkyl; amino; di-lower alkyl-amino; [N-(hydroxy-lower alkyl)-N-(lower alkyl)]-amino; aryl; aryl-amino; aryl-lower alkyl-amino; aryl-thio; aryl-lower alkyl-thio; aryloxy; aryl-lower alkyl-oxy; aryl-lower alkyl; aryl-sulfinyl; heteroaryl; heteroaryl-oxy; heteroaryl-lower alkyl-oxy; heteroaryl-amino; heteroaryl-lower alkyl-amino; heteroaryl-thio; heteroaryl-lower alkyl-thio; heteroaryl-lower alkyl; heteroaryl-sulfinyl; heterocyclyl; heterocyclyl-lower alkyl-oxy; heterocyclyl-oxy; heterocyclyl-amino; heterocyclyl-lower alkyl-amino; heterocyclyl-thio; heterocyclyl-lower alkyl-thio; heterocyclyl-lower alkyl; heterocyclyl-sulfinyl; cycloalkyl; cycloalkyl-oxy; cycloalkyl-lower alkyl-oxy; cycloalkyl-amino; cycloalkyl-lower alkyl-amino; cycloalkyl-thio; cycloalkyl-lower alkyl-thio; cycloalkyl-lower alkyl; or cycloalkyl-sulfinyl;

$R^6$ represents hydrogen; lower alkyl; cycloalkyl; heterocyclyl; heteroaryl; aryl; cycloalkyl-lower alkyl; heterocyclyl-lower alkyl; heteroaryl-lower alkyl; aryl-lower alkyl; lower alkoxy-lower alkyl; lower alkyl-thio-lower alkyl; lower alkyl-amino-lower alkyl; lower alkenyl; or lower alkynyl;

n represents the numbers 2, 3, 4 or 5; and

X represents oxygen; sulfur; NH; $CH_2$ or a bond.

2. The compound of claim 1 and a pharmaceutically acceptable salt thereof, wherein X represents oxygen and $R^3$ represents phenyl, mono-, or di-substituted phenyl substituted with halogen, lower alkyl, lower alkylen, lower alkyloxy, amino, lower alkyl-amino, lower alkyl-thio, hydroxy, hydroxymethyl or lower alkanoyl.

3. A Compound of formula II

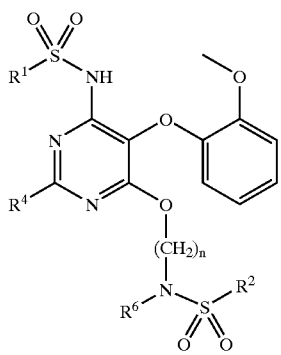

formula II and a pharmaceutically acceptable salt thereof, wherein $R^1$ represents aryl; aryl-lower alkyl; aryl-lower alkenyl; heteroaryl; or heteroaryl-lower alkyl;

$R^2$ represents lower alkyl; trifluoromethyl; lower alkoxy-lower alkyl; lower alkenyl; lower alkynyl; aryl; aryl-lower alkyl; aryl-lower alkenyl; heterocyclyl; heterocyclyl-lower alkyl; heteroaryl; heteroaryl-lower alkyl; cycloalkyl; or cycloalkyl-lower alkyl;

$R^4$ represents hydrogen; halogen; trifluoromethyl; lower alkyl; lower alkyl-amino; lower alkyloxy; lower alkyl-sulfono; lower alkyl-sulfinyl; lower alkylthio; lower alkylthio-lower alkyl; hydroxy-lower alkyl; lower alkyl-oxy-lower alkyl; hydroxy-lower alkyl-oxy-lower alkyl; hydroxy-lower alkyl-amino; lower alkyl-amino-lower alkyl; amino; di-lower alkyl-amino; [N-(hydroxy-lower alkyl)-N-(lower alkyl)]-amino; aryl; aryl-amino; aryl-lower alkyl-amino; aryl-thio; aryl-lower alkyl-thio; aryloxy; aryl-lower alkyl-oxy; aryl-lower alkyl; aryl-sulfinyl; heteroaryl; heteroaryl-oxy; heteroaryl-lower alkyl-oxy; heteroaryl-amino; heteroaryl-lower alkyl-amino; heteroaryl-thio; heteroaryl-lower alkyl-thio; heteroaryl-lower alkyl; heteroaryl-sulfinyl; heterocyclyl; heterocyclyl-lower alkyl-oxy; heterocyclyl-oxy; heterocyclyl-amino; heterocyclyl-lower alkyl-amino; heterocyclyl-thio; heterocyclyl-lower alkyl-thio; heterocyclyl-lower alkyl; heterocyclyl-sulfinyl; cycloalkyl; cycloalkyl-oxy; cycloalkyl-lower alkyl-oxy; cycloalkyl-amino; cycloalkyl-lower alkyl-amino; cycloalkyl-thio; cycloalkyl-lower alkyl-thio; cycloalkyl-lower alkyl; or cycloalkyl-sulfinyl;

$R^6$ represents hydrogen; lower alkyl; cycloalkyl; heterocyclyl; heteroaryl; aryl; cycloalkyl-lower alkyl; heterocyclyl-lower alkyl; heteroaryl-lower alkyl; aryl-lower alkyl; lower alkoxy-lower alkyl; lower alkyl-thio-lower alkyl; lower alkyl-amino-lower alkyl; lower alkenyl; or lower alkynyl; and n represents the numbers 2, 3, 4 or 5.

4. A compound of formula III

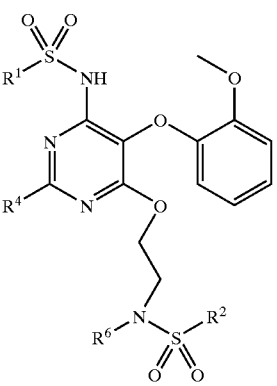

and a pharmaceutically acceptable salt thereof, wherein $R^1$ represents aryl; aryl-lower alkyl; aryl-lower alkenyl; heteroaryl; or heteroaryl-lower alkyl;

$R^2$ represents lower alkyl; trifluoromethyl; lower alkoxy-lower alkyl; lower alkenyl; lower alkynyl; aryl; aryl-lower alkyl; aryl-lower alkenyl; heterocyclyl; heterocyclyl-lower alkyl; heteroaryl; heteroaryl-lower alkyl; cycloalkyl; or cycloalkyl-lower alkyl;

$R^4$ represents hydrogen; halogen; trifluoromethyl; lower alkyl; lower alkyl-amino; lower alkyloxy; lower alkyl-sulfono; lower alkyl-sulfinyl; lower alkylthio; lower alkylthio-lower alkyl; hydroxy-lower alkyl; lower alkyl-oxy-lower alkyl; hydroxy-lower alkyl-oxy-lower alkyl; hydroxy-lower alkyl-amino; lower alkyl-amino-lower alkyl; amino; di-lower alkyl-amino; [N-(hydroxy-lower alkyl)-N-(lower alkyl)]-amino; aryl; aryl-amino; aryl-lower alkyl-amino; aryl-thio; aryl-lower alkyl-thio; aryloxy; aryl-lower alkyl-oxy; aryl-lower alkyl; aryl-sulfinyl; heteroaryl; heteroaryl-oxy; heteroaryl-lower alkyl-oxy; heteroaryl-amino; heteroaryl-lower alkyl-amino; heteroaryl-thio; heteroaryl-lower alkyl-thio; heteroaryl-lower alkyl; heteroaryl-sulfinyl; heterocyclyl; heterocyclyl-lower alkyl-oxy; heterocyclyl-oxy; heterocyclyl-amino; heterocyclyl-lower alkyl-amino; heterocyclyl-thio; heterocyclyl-lower alkyl-thio; heterocyclyl-lower alkyl; heterocyclyl-sulfinyl; cycloalkyl; cycloalkyl-oxy; cycloalkyl-lower alkyl-oxy; cycloalkyl-amino; cycloalkyl-lower alkyl-amino; cycloalkyl-thio; cycloalkyl-lower alkyl-thio; cycloalkyl-lower alkyl; or cycloalkyl-sulfinyl; and $R^6$ represents hydrogen; lower alkyl; cycloalkyl; heterocyclyl; heteroaryl; aryl; cycloalkyl-lower alkyl; heterocyclyl-lower alkyl; heteroaryl-lower alkyl; aryl-lower alkyl; lower alkoxy-lower alkyl; lower alkyl-thio-lower alkyl; lower alkyl-amino-lower alkyl; lower alkenyl; or lower alkynyl.

5. A compound of formula IV

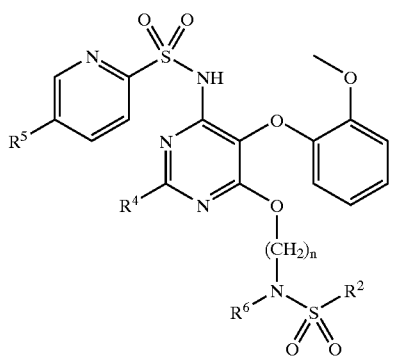

formula IV a pharmaceutically acceptable salt thereof,
wherein
- $R^2$ represents lower alkyl; trifluoromethyl; lower alkoxy-lower alkyl; lower alkenyl; lower alkynyl; aryl; aryl-lower alkyl; aryl-lower alkenyl; heterocyclyl; heterocyclyl-lower alkyl; heteroaryl; heteroaryl-lower alkyl; cycloalkyl; or cycloalkyl-lower alkyl;
- $R^4$ represents hydrogen; halogen; trifluoromethyl; lower alkyl; lower alkyl-amino; lower alkyloxy; lower alkyl-sulfono; lower alkyl-sulfinyl; lower alkylthio; lower alkylthio-lower alkyl; hydroxy-lower alkyl; lower alkyl-oxy-lower alkyl; hydroxy-lower alkyl-oxy-lower alkyl; hydroxy-lower alkyl-amino; lower alkyl-amino-lower alkyl; amino; di-lower alkyl-amino; [N-(hydroxy-lower alkyl)-N-(lower alkyl)]-amino; aryl; aryl-amino; aryl-lower alkyl-amino; aryl-thio; aryl-lower alkyl-thio; aryloxy; aryl-lower alkyl-oxy; aryl-lower alkyl; aryl-sulfinyl; heteroaryl; heteroaryl-oxy; heteroaryl-lower alkyl-oxy; heteroaryl-amino; heteroaryl-lower alkyl-amino; heteroaryl-thio; heteroaryl-lower alkyl-thio; heteroaryl-lower alkyl; heteroaryl-sulfinyl; heterocyclyl; heterocyclyl-lower alkyl-oxy; heterocyclyl-oxy; heterocyclyl-amino; heterocyclyl-lower alkyl-amino; heterocyclyl-thio; heterocyclyl-lower alkyl-thio; heterocyclyl-lower alkyl; heterocyclyl-sulfinyl; cycloalkyl; cycloalkyl-oxy; cycloalkyl-lower alkyl-oxy; cycloalkyl-amino; cycloalkyl-lower alkyl-amino; cycloalkyl-thio; cycloalkyl-lower alkyl-thio; cycloalkyl-lower alkyl; or cycloalkyl-sulfinyl;
- $R^5$ represents hydrogen, methyl or isopropyl;
- $R^6$ represents hydrogen; lower alkyl; cycloalkyl; heterocyclyl; heteroaryl; aryl; cycloalkyl-lower alkyl; heterocyclyl-lower alkyl; heteroaryl-lower alkyl; aryl-lower alkyl; lower alkoxy-lower alkyl; lower alkyl-thio-lower alkyl; lower alkyl-amino-lower alkyl; lower alkenyl; or lower alkynyl; and
- n represents the numbers 2 or 3.

6. The compound according to claim 5 and a pharmaceutically acceptable salt thereof, wherein $R^4$ represents lower alkyl, lower alkyloxy-lower alkyl or lower alkyloxy-lower alkyloxy-lower alkyl.

7. The compound according to claim 5 and a pharmaceutically acceptable salt thereof, wherein $R^4$ represents methyl.

8. The compound according to claim 5 and a pharmaceutically acceptable salt thereof, wherein $R^4$ represents cycloalkyl.

9. The compound according to claim 5 and a pharmaceutically acceptable salt thereof, wherein $R^4$ represents N-attached morpholinyl.

10. The compound according to claim 5 and a pharmaceutically acceptable salt thereof, wherein $R^4$ represents phenyl, mono-, di- or tri-substituted phenyl substituted with lower alkyl, lower alkyloxy or methylendioxy.

11. A compound of formula V

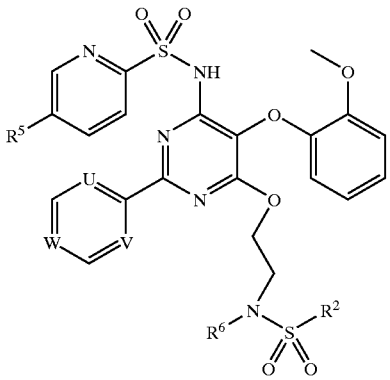

formula V and a pharmaceutically acceptable salt thereof,
wherein
- $R^2$ represents lower alkyl; trifluoromethyl; lower alkoxy-lower alkyl; lower alkenyl; lower alkynyl; aryl; aryl-lower alkyl; aryl-lower alkenyl; heterocyclyl; heterocyclyl-lower alkyl; heteroaryl; heteroaryl-lower alkyl; cycloalkyl; or cycloalkyl-lower alkyl;
- $R^5$ represents hydrogen, methyl or isopropyl;
- $R^6$ represents hydrogen; lower alkyl; cycloalkyl; heterocyclyl; heteroaryl; aryl; cycloalkyl-lower alkyl; heterocyclyl-lower alkyl; heteroaryl-lower alkyl; aryl-lower alkyl; lower alkoxy-lower alkyl; lower alkyl-thio-lower alkyl; lower alkyl-amino-lower alkyl; lower alkenyl; or lower alkynyl;
- U and V represent nitrogens, respectively; and
- W represents carbon.

12. The compound according to claim 11 and a pharmaceutically acceptable salt thereof, wherein U and V represent carbons, respectively, and W represents nitrogen.

13. A compound according to formula VI

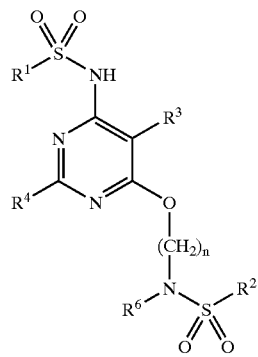

formula VI and a pharmaceutically acceptable salt thereof,
wherein
- $R^1$ represents aryl; aryl-lower alkyl; aryl-lower alkenyl; heteroaryl; or heteroaryl-lower alkyl;
- $R^2$ represents lower alkyl; trifluoromethyl; lower alkoxy-lower alkyl; lower alkenyl; lower alkynyl; aryl; aryl-lower alkyl; aryl-lower alkenyl; heterocyclyl;

heterocyclyl-lower alkyl; heteroaryl; heteroaryl-lower alkyl; cycloalkyl; or cycloalkyl-lower alkyl;

$R^3$ represents phenyl; mono-, di- or tn-substituted phenyl substituted with lower alkyl, lower alkenyl, lower alkynyl, lower alkyloxy, amino, lower alkylamino, amino-lower alkyl, trifluoromethyl, trifluoromethoxy, halogen, lower alkylthio, hydroxy, hydroxy-lower alkyl, cyano, carboxyl, lower alkanoyl, formyl; benzofuranyl; aryl; or heteroaryl;

$R^4$ represents hydrogen; halogen; trifluoromethyl; lower alkyl; lower alkyl-amino; lower alkyloxy; lower alkyl-sulfono; lower alkyl-sulfinyl; lower alkylthio; lower alkylthio-lower alkyl; hydroxy-lower alkyl; lower alkyl-oxy-lower alkyl; hydroxy-lower alkyl-oxy-lower alkyl; hydroxy-lower alkyl-amino; lower alkyl-amino-lower alkyl; amino; di-lower alkyl-amino; [N-(hydroxy-lower alkyl)-N-(lower alkyl)]-amino; aryl; aryl-amino; aryl-lower alkyl-amino; aryl-thio; aryl-lower alkyl-thio; aryloxy; aryl-lower alkyl-oxy; aryl-lower alkyl; aryl-sulfinyl; heteroaryl; heteroaryl-oxy; heteroaryl-lower alkyl-oxy; heteroaryl-amino; heteroaryl-lower alkyl-amino; heteroaryl-thio; heteroaryl-lower alkyl-thio; heteroaryl-lower alkyl; heteroaryl-sulfinyl; heterocyclyl; heterocyclyl-lower alkyl-oxy; heterocyclyl-oxy; heterocyclyl-amino; heterocyclyl-lower alkyl-amino; heterocyclyl-thio; heterocyclyl-lower alkyl-thio; heterocyclyl-lower alkyl; heterocyclyl-sulfinyl; cycloalkyl; cycloalkyl-oxy; cycloalkyl-lower alkyl-oxy; cycloalkyl-amino; cycloalkyl-lower alkyl-amino; cycloalkyl-thio; cycloalkyl-lower alkyl-thio; cycloalkyl-lower alkyl; or cycloalkyl-sulfinyl;

$R^6$ represents hydrogen; lower alkyl; cycloalkyl; heterocyclyl; heteroaryl; aryl; cycloalkyl-lower alkyl; heterocyclyl-lower alkyl; heteroaryl-lower alkyl; aryl-lower alkyl; lower alkoxy-lower alkyl; lower alkyl-thio-lower alkyl; lower alkyl-amino-lower alkyl; lower alkenyl; or lower alkynyl; and n represents the numbers 2, 3, 4 or 5.

14. A compound according to formula VII

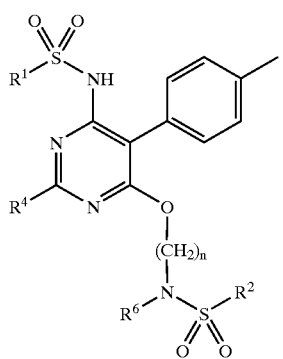

formula VII and a pharmaceutically acceptable salt thereof, wherein $R^1$ represents aryl; aryl-lower alkyl; aryl-lower alkenyl; heteroaryl; or heteroaryl-lower alkyl;

$R^2$ represents lower alkyl; trifluoromethyl; lower alkoxy-lower alkyl; lower alkenyl; lower alkynyl; aryl; aryl-lower alkyl; aryl-lower alkenyl; heterocyclyl; heterocyclyl-lower alkyl; heteroaryl; heteroaryl-lower alkyl; cycloalkyl; or cycloalkyl-lower alkyl;

$R^4$ represents hydrogen; halogen; trifluoromethyl; lower alkyl; lower alkyl-amino; lower alkyloxy; lower alkyl-sulfono; lower alkyl-sulfinyl; lower alkylthio; lower alkylthio-lower alkyl; hydroxy-lower alkyl; lower alkyl-oxy-lower alkyl; hydroxy-lower alkyl-oxy-lower alkyl; hydroxy-lower alkyl-amino; lower alkyl-amino-lower alkyl; amino; di-lower alkyl-amino; [N-(hydroxy-lower alkyl)-N-(lower alkyl)]-amino; aryl; aryl-amino; aryl-lower alkyl-amino; aryl-thio; aryl-lower alkyl-thio; aryloxy; aryl-lower alkyl-oxy; aryl-lower alkyl; aryl-sulfinyl; heteroaryl; heteroaryl-oxy; heteroaryl-lower alkyl-oxy; heteroaryl-amino; heteroaryl-lower alkyl-amino; heteroaryl-thio; heteroaryl-lower alkyl-thio; heteroaryl-lower alkyl; heteroaryl-sulfinyl; heterocyclyl; heterocyclyl-lower alkyl-oxy; heterocyclyl-oxy; heterocyclyl-amino; heterocyclyl-lower alkyl-amino; heterocyclyl-thio; heterocyclyl-lower alkyl-thio; heterocyclyl-lower alkyl; heterocyclyl-sulfinyl; cycloalkyl; cycloalkyl-oxy; cycloalkyl-lower alkyl-oxy; cycloalkyl-amino; cycloalkyl-lower alkyl-amino; cycloalkyl-thio; cycloalkyl-lower alkyl-thio; cycloalkyl-lower alkyl; or cycloalkyl-sulfinyl;

$R^6$ represents hydrogen; lower alkyl; cycloalkyl; heterocyclyl; heteroaryl; aryl; cycloalkyl-lower alkyl; heterocyclyl-lower alkyl; heteroaryl-lower alkyl; aryl-lower alkyl; lower alkoxy-lower alkyl; lower alkyl-thio-lower alkyl; lower alkyl-amino-lower alkyl; lower alkenyl; or lower alkynyl; and n represents the numbers 2, 3, 4 or 5.

15. The compound according to any one of claims 6 to 14 and a pharmaceutically acceptable salt thereof, wherein $R^2$ represents lower alkyl.

16. The compound according to any one of claims 6 to 14 and a pharmaceutically acceptable salt thereof, wherein $R^2$ represents cycloalkyl.

17. The compound according to any one of claims 6 to 14 and a pharmaceutically acceptable salt thereof, wherein $R^2$ represents phenyl, p-tolyl, 2- or 3-thienyl, 2- or 3-pyridyl, or 5-methyl-2-pyridyl.

18. The compound according to any one of claims 6 to 14 and a pharmaceutically acceptable salt thereof, wherein $R^2$ represents naphthyl, quinolyl or biphenyl.

19. The compound according to any one of claims 1 to 14, wherein the compound is selected from the group consisting of:

p-tert.-butyl-N-[6-(ethoxy-2-(2-thiophenesulfonamido))-5-(o-methoxyphenoxy)-2-(2-pyrimidinyl)-4-pyrimidinyl]benzene-sulfonamide, 5-i.-propyl-N-[6-(ethoxy-2-(2-propanesulfonamido))-5-(o-methoxyphenoxy)-2-(4-pyridyl)-4-pyrimidinyl]pyridine-2-sulfonamide, 5-i.-propyl-N-[6-(ethoxy-2-(4-methylbenzenesulfonamido))-5-(o-methoxyphenoxy)-2-(3,4,5-trimethoxyphenyl)-4-pyrimidinyl]pyridine-2-sulfonamide, 5-i.-propyl-N-[6-(ethoxy-2-(4-methylbenzenesulfonamido)-5-(o-methoxyphenoxy)-2-(4-pyridyl)-4-pyrimidinyl]pyridine-2-sulfonamide, 5-i.-propyl-N-[6-(ethoxy-2-benzenesulfonamido)-5-(o-methoxyphenoxy)-2-(4-pyridyl)-4-pyrimidinyl]pyridine-2-sulfonamide, 5-i.-propyl-N-[6-(ethoxy-2-thiophenesulfonamido)-5-(o-methoxyphenoxy)-2-(3,4,5-trimethoxyphenyl)-4-pyrimidinyl]pyridine-2-sulfonamide, 5-i.-propyl-N-[6-(ethoxy-2-(1-propanesulfonamido))-5-(o-methoxyphenoxy)-2-(3,4,5-trimethoxyphenyl)-4-pyrimidinyl]pyridine-2-sulfonamide, p-tert.-butyl-N-[6-(ethoxy-2-(1-butanesulfonamido))-5-(o-methoxyphenoxy)-2-(2-pyrimidinyl)-4-pyrimidinyl]benzene-sulfonamide, 5-i.-propyl-N-[6-(ethoxy-2-p-toluenesulfonamido)-5-(o-methoxyphenoxy)-2-methyl-4-pyrimidinyl]pyridine-2-sulfonamide, 5-i.-propyl-N-[6-(ethoxy-2-methanesulfonamido)-5-(o-methoxyphenoxy)-2-methyl-4-pyrimidinyl]pyridine-2-sulfonamide, 4-tert.-butyl-N-[6-(2-ethanesulfonylamino-ethoxy)-2-methanesulfonyl-5-(o-methoxyphenoxy-pyrimidin-4-yl]-benzenesulfonamide, 5-i-propyl-N-[6-chloro-5-(o-methoxyphenoxy)-2-cyclopropyl-pyrimidin-4-yl]-pyridine-2-sulfonamide, 5-i-propyl-N-[6-(2-(4-methylbenzene)-sulfonylamino-ethoxy)-5-(o-methoxyphenoxy)-2-cyclopropyl-pyrimidin-4-yl]-pyridine-2-sulfonamide, 4-tert.-butyl-N-[6-(2-(2-propane)-sulfonylamino-ethoxy)-5-(o-methoxyphenoxy)-2-cyclopropyl-pyrimidin-4-yl]-benzene-sulfonamide, 5-isoproyl-N-[6-(2-(2-thiophensulfonyl)-amino-ethoxy)-5-(o-methoxyphenoxy)-2-(N-morpholino)-4-pyrimidinyl]-2-pyridine sulfonamide, 5-i-propyl-N-[6-(2-ethanesulfonylamino-ethoxy)-5-(o-methoxyphenoxy)-2-cyclopropyl-pyrimidin-4-yl]-pyridine-2-sulfonamide, 5-isopropyl-N-[6-(2-propanesulfonylamino-ethoxy)-5-(o-methoxyphenoxy)-2-(N-morpholino)-4-pyrimidinyl]-2-pyridine sulfonamide, 5-methyl-N-[6-(2-(1-propanesulfonylamino)-ethoxy)-5-(o-methoxyphenoxy)-2-(N-morpholino)-4-pyrimidinyl]-2-pyridine sulfonamide, 5-isopropyl-N-[6-(2-(4-methylbenzenesulfonylamino)-ethoxy)-5-(o-methoxyphenoxy)-2-(N-morpholino)-4-pyrimidinyl]-2-pyridine sulfonamide, 5-isopropyl-N-[6-(2-(ethanesulfonylamino)-ethoxy)-5-(o-methoxyphenoxy)-2-(N-morpholino)-4-pyrimidinyl]-2-pyridine sulfonamide, p-tert.-butyl-N-(6-(ethoxy-2-(2-thiophenesulfonamido))-5-(o-methoxyphenoxy)-2-(2-pyrimidinyl)-4-pyrimidinyl] benzene-sulfonamide, 5-i.-propyl-N-[6-(ethoxy-2-(4-methylbenzenesulfonamido))-5-(o-methoxyphenoxy)-2-(3,4,5-trimethoxyphenyl)-4-pyrimidinyl]pyridine-2-sulfonamide, 5-i.-propyl-N-[6-(ethoxy-2-thiophenesulfonamido)-5-(o-methoxyphenoxy)-2-(3,4,5-trimethoxyphenyl)-4-pyrimidinyl]pyridine-2-sulfonamide, 5-isopropyl-N-[6-(2-(4-methylbenzenesulfonylamino)-ethoxy)-5-(o-methoxyphenoxy)-2-(N-morpholino)-4-pyrimidinyl]-2-pyridine sulfonamide, 5-isopropyl-N-[6-(2-(ethanesulfonylamino)-ethoxy)-5-(o-methoxyphenoxy)-2-(N-morpholino)-4-pyrimidinyl]-2-pyridine sulfonamide, 4-tert-butyl-N-[6-(3-(ethanesulfonylamino)-propoxy)-5-(o-methoxyphenoxy)-2-pyrimidinyl-4-pyrimidinyl]-benzene-sulfonamide, 4-tert.-butyl-N-[6-(3-(2-thiophenesulfonylamino)-propoxy)-5-(o-meth-oxyphenoxy)-2-pyrimidinyl-4-pyrimidinyl]-benzene-sulfonamide, 4-tert.-butyl-N-[6-(3-(ethanesulfonylamino)-propoxy)-5-(o-methoxyphenoxy)-2-cyclopropyl-4-pyrimidinyl]-benzene-sulfonamide, 4-tert.-butyl-N-[6-(3-(2-thiophenesulfonylamino)-propoxy)-5-(o-methoxyphenoxy)-2-cyclopropyl-4-pyrimidinyl]-benzene-sulfonamide, 5-i.-propyl-N-[6-(3-(propanesulfonylamino)-propoxy)-5-(o-methoxy-phenoxy)-2-cyclopropyl-4-pyrimidinyl]-pyridine-2-sulfonamide, 5-i.-propyl-N-[6-(3-(2-thiophenesulfonylamino)-propoxy)-5-(o-methoxy-phenoxy)-2-cyclopropyl-4-pyrimidinyl]-pyridine-2-sulfonamide, and 5-i.-propyl-N -[6-(3-(p-toluenesulfonylamino)-propoxy)-5-(o-methoxy-phenoxy)-2-cyclopropyl-4-pyrimidinyl]-pyridine-2-sulfonamide, and a pharmaceutically acceptable salt thereof.

20. A pharmaceutical composition comprising the compound of any one of claims 1–14 as an active ingredient and a pharmaceutically acceptable excipient and/or adjuvant.

21. A method of treating or ameliorating a disorder in a subject, wherein the disorder is hypertension, ischemia, vasospasm, angina pectoris, renal failure, dementia, migraine, subarachnoidal hemorrhage, Raynaud's syndrome, atherosclerosis, stomach ulcer, duodenal ulcer, prostatic hypertrophy, erectile dysfunction, hearing loss, amaurosis, chronic bronchitis, asthma, gram negative septicemia, shock, sickle cell anemia, glomerulonephritis, graucoma, diabetic complications, complications of transplantation, or complications of cyclosporin, and is associated with endothelin, comprising administering a therapeutically effective amount of the compound according to any one of the claims 1 to 14.

22. A method of treating or ameliorating a disorder in a subject, wherein the disorder is hypertension, ischemia, vasospasm, angina pectoris, renal failure, dementia, migraine, subarachnoidal hemorrhage, Raynaud's syndrome, atherosclerosis, stomach ulcer, duodenal ulcer, prostatic hypertrophy, erectile dysfunction, hearing loss, amaurosis, chronic bronchitis, asthma, gram negative septicemia, shock, sickle cell anemia, glomerulonephritis, graucoma, diabetic complications, complications of transplantation, or complications of cyclosporin, and is associated with endothelin, comprising administering a therapeutically effective amount of the composition according to claim 21.

23. A process for the manufacture of the compound according to any one of claims 1 to 14, which process comprises a) reacting a compound of formula VIII

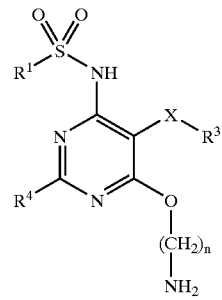

formula VIII wherein $R^1$ represents aryl; aryl-lower alkyl; aryl-lower alkenyl; heteroaryl; or heteroaryl-lower alkyl;

$R^3$ represents phenyl; mono-, di- or tn-substituted phenyl substituted with lower alkyl, lower alkenyl, lower alkynyl, lower alkyloxy, amino, lower alkylamino, amino-lower alkyl, trifluoromethyl, trifluoromethoxy, halogen, lower alkylthio, hydroxy, hydroxy-lower alkyl, cyano, carboxyl, lower alkanoyl, formyl; benzofuranyl; aryl; or heteroaryl;

$R^4$ represents hydrogen; halogen; trifluoromethyl; lower alkyl; lower alkyl-amino; lower alkyloxy; lower alkyl-sulfono; lower alkyl-sulfinyl; lower alkylthio; lower alkylthio-lower alkyl; hydroxy-lower alkyl; lower alkyl-oxy-lower alkyl; hydroxy-lower alkyl-oxy-lower alkyl; hydroxy-lower alkylamino; lower alkyl-amino-lower alkyl; amino; di-lower alkyl-amino; [N-(hydroxy-lower alkyl)-N-(lower alkyl)]-amino; aryl; aryl-amino; aryl-lower alkyl-amino; aryl-thio; aryl-lower alkyl-thio; aryloxy; aryl-lower alkyl-oxy; aryl-lower alkyl; aryl-sulfinyl; heteroaryl; heteroaryl-oxy; heteroaryl-lower alkyl-oxy; heteroaryl-amino; heteroaryl-lower alkyl-amino; heteroaryl-thio; heteroaryl-lower alkyl-thio; heteroaryl-lower alkyl; heteroaryl-sulfinyl; heterocyclyl; heterocyclyl-lower alkyl-oxy; heterocyclyl-oxy; heterocyclyl-amino; heterocyclyl-lower alkyl-amino; heterocyclyl-thio; heterocyclyl-lower alkyl-thio; heterocyclyl-lower alkyl; heterocyclyl-sulfinyl; cycloalkyl; cycloalkyl-oxy; cycloalkyl-lower alkyl-oxy; cycloalkyl-amino; cycloalkyl-lower alkyl-amino; cycloalkyl-thio; cycloalkyl-lower alkyl-thio; cycloalkyl-lower alkyl; or cycloalkyl-sulfinyl;

X represents oxygen; sulfur; NH; $CH_2$ or a bond; and n represents the numbers 2, 3, 4 or 5, with a compound of the formula $Cl-SO_2-R^2$, wherein $R^2$ represents lower alkyl; trifluoromethyl; lower alkoxy-lower alkyl; lower alkenyl; lower alkynyl; aryl; aryl-lower alkyl; aryl-lower alkenyl; heterocyclyl; heterocyclyl-lower alkyl; heteroaryl; heteroaryl-lower alkyl; cycloalkyl; or cycloalkyl-lower alkyl; or b) reacting a compound of formula IX

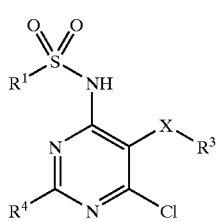

formula IX wherein
$R^1$ represents aryl; aryl-lower alkyl; aryl-lower alkenyl; heteroaryl; or heteroaryl-lower alkyl;

$R^3$ represents phenyl; mono-, di- or tri-substituted phenyl substituted with lower alkyl, lower alkenyl, lower alkynyl, lower alkyloxy, amino, lower alkylamino, amino-lower alkyl, trifluoromethyl, trifluoromethoxy, halogen, lower alkylthio, hydroxy, hydroxy-lower alkyl, cyano, carboxyl, lower alkanoyl, formyl; benzofuranyl; aryl; or heteroaryl;

$R^4$ represents hydrogen; halogen; trifluoromethyl; lower alkyl; lower alkyl-amino; lower alkyloxy; lower alkyl-sulfono; lower alkyl-sulfinyl; lower alkylthio; lower alkylthio-lower alkyl; hydroxy-lower alkyl; lower alkyl-oxy-lower alkyl; hydroxy-lower alkyl-oxy-lower alkyl; hydroxy-lower alkyl-amino; lower alkyl-amino-lower alkyl; amino; di-lower alkyl-amino; [N-(hydroxy-lower alkyl)-N-(lower alkyl)]-amino; aryl; aryl-amino; aryl-lower alkyl-amino; aryl-thio; aryl-lower alkyl-thio; aryloxy; aryl-lower alkyl-oxy; aryl-lower alkyl; aryl-sulfinyl; heteroaryl; heteroaryl-oxy; heteroaryl-lower alkyl-oxy; heteroaryl-amino; heteroaryl-lower alkyl-amino; heteroaryl-thio; heteroaryl-lower alkyl-thio; heteroaryl-lower alkyl; heteroaryl-sulfinyl; heterocyclyl; heterocyclyl-lower alkyl-oxy; heterocyclyl-oxy; heterocyclyl-amino; heterocyclyl-lower alkyl-amino; heterocyclyl-thio; heterocyclyl-lower alkyl-thio; heterocyclyl-lower alkyl; heterocyclyl-sulfinyl; cycloalkyl; cycloalkyl-oxy; cycloalkyl-lower alkyl-oxy; cycloalkyl-amino; cycloalkyl-lower alkyl-amino; cycloalkyl-thio; cycloalkyl-lower alkyl-thio; cycloalkyl-lower alkyl; or cycloalkyl-sulfinyl; and X represents oxygen; sulfur; NH; $CH_2$ or a bond, with a compound of formula X

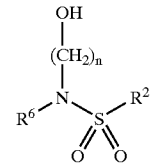

formula X wherein $R^2$ represents lower alkyl; trifluoromethyl; lower alkoxy-lower alkyl; lower alkenyl; lower alkynyl; aryl; aryl-lower alkyl; aryl-lower alkenyl; heterocyclyl; heterocyclyl-lower alkyl; heteroaryl; heteroaryl-lower alkyl; cycloalkyl; or cycloalkyl-lower alkyl;

$R^6$ represents hydrogen; lower alkyl; cycloalkyl; heterocyclyl; heteroaryl; aryl; cycloalkyl-lower alkyl; heterocyclyl-lower alkyl; heteroaryl-lower alkyl; aryl-lower alkyl; lower alkoxy-lower alkyl; lower alkyl-thio-lower alkyl; lower alkyl-amino-lower alkyl; lower alkenyl; or lower alkynyl; and n represents the numbers 2, 3, 4 or 5, and, if necessary, resolving an optically active compound into pure diastereomers, a mixture of diastereomers, diastereomeric racemates, a mixture of diastereomeric racemates and meso-forms and, if desired, converting a compound of formula I obtained into a pharmaceutically acceptable salt.

24. A process for the manufacture of the pharmaceutical composition according to claim 20, comprising mixing one or more active ingredients with the pharmaceutically acceptable excipient.

* * * * *